(12) United States Patent
Black et al.

US006842704B2

(10) Patent No.: US 6,842,704 B2
(45) Date of Patent: Jan. 11, 2005

(54) CRYSTALLINE TNF-α-CONVERTING ENZYME AND USES THEREOF

(75) Inventors: Roy A. Black, Seattle, WA (US); Raymond James Paxton, Bellevue, WA (US); Wolfram Bode, Gauting (DE); Klaus Maskos, Holzkirchen (DE); Carlos Fernandez-Catalan, Martinsried-Planegg (DE); James Ming Chen, Bedminister, NJ (US); Jeremy Ian Levin, New City, NY (US)

(73) Assignees: Immunex Corporation, Seattle, WA (US); Max-Planck-Institute for Biochemistry, Klopferspitz (DE); Wyeth, Madison, NJ (US)

(*) Notice: Subject to any disclaimer, the term of this patent is extended or adjusted under 35 U.S.C. 154(b) by 0 days.

(21) Appl. No.: 09/244,984

(22) Filed: Feb. 4, 1999

(65) Prior Publication Data

US 2002/0081692 A1 Jun. 27, 2002

Related U.S. Application Data

(60) Provisional application No. 60/117,476, filed on Jan. 27, 1999, provisional application No. 60/135,499, filed on Mar. 30, 1998, and provisional application No. 60/073,709, filed on Feb. 4, 1998.

(51) Int. Cl.[7] .............................. G06N 7/00; C12Q 1/48; C12N 9/10

(52) U.S. Cl. .............................. 702/27; 702/30; 703/1; 703/2; 435/15; 435/193

(58) Field of Search .......................... 435/7.1, 23, 69.1, 435/91.4, 91.41; 434/277, 278; 530/350; 702/27, 28, 30; 703/2

(56) References Cited

U.S. PATENT DOCUMENTS

| 5,011,912 A | 4/1991 | Hopp et al. ................ 530/387 |
| 5,594,106 A | 1/1997 | Black et al. ................ 530/331 |
| 5,702,935 A | 12/1997 | Sacchettini et al. ......... 435/193 |
| 5,830,742 A | 11/1998 | Black et al. |

FOREIGN PATENT DOCUMENTS

| EP | 0646599 A2 | 4/1995 |
| GB | 2306961 A | 5/1997 |
| WO | WO95/35367 | 12/1995 |
| WO | WO96/41624 | 12/1996 |
| WO | WO97/08300 | 3/1997 |
| WO | WO97/15588 | 5/1997 |
| WO | WO97/35538 | 10/1997 |

OTHER PUBLICATIONS

Rutenber et al. Structure of a non–peptide inhibitor coomplexed with HIV–1 protease. Journal of Biological Chemistry, vol. 268(21), pp. 15343–15346 (1993).*

Gilliland et al. Crystallization of biological macromolecules for X–ray diffraction studies. Current Opinion in Structural Biology, vol. 6, pp. 595–603 (1996).*
Cirilli et al., FEBS Letters 418: 319–322 (1997).
Decicco et al., Abstracts of Papers American Chemical Society vol. 214, No. 1–2, PP. MEDI 96 (1997).
Gomis–Ruth et al., Protein Science 7: 283–292 (1998).
Black et al., Biochemical & Biophysical Research Communications 225(2): 400–405 (1996).
Black et al., Nature 385: 729–733 (1997).
Bode et al., FEBS Letters 331 (1,2): 134–140 (1993).
Gomis–Ruth et al., The EMBO Journal 12(11): 4151–4157 (1993).
Grams et al., Eur. J. Biochem. 228: 830–841 (1995).
Kaufman, Methods in Enzymology—Gene Expression Tech., vol. 185, Chap. 42, pp. 537–566 (1990).
Lunn et al., FEBS Letters 400: 333–335 (1997).
Maskos et al., Proc. Natl. Acad. Sci. USA 95: 3408–3412 (1998).
Moss et al., Nature 385: 733–736 (1997).
Nicholls et al., GRASP: Graphical Representation and Analysis of Surface Properties (Abstract TU–POS189).
Rooke et al., Science 273: 1227–1231 (1996).
Saudek et al., Biochemistry 30: 7369–7372 (1991).
Stocker et al., Protein Science 4: 823–840 (1995).
Tang et al., Biochemistry 35: 8216–8225 (1996).
Tang et al., Biochemistry 35: 8226–8233 (1996).
Wolfsberg et al., Development Biology 180: 389–401 (1996).
Bemelmans et al., Critical Review in Immunology 16: 1–11 (1996).
DiMartino et al., Inflammation Research 46: 211–215 (1997).
Evans, J. Mol. Graphics 11: 127–128 & 134–138 (1993).
Gluzman, Cell 23: 175–182 (1981).
Gomis–Ruth et al., J. Mol. Biol. 239: 513–544 (1994).
Gomis–Ruth et al., Nature 389: 77–81 (1997).
Hopp et al., Bio/Technology 6: 1204–1210 (1988).
Jones et al., Nature 338: 225–228 (1989).
Luckow et al., Bio/Technology 6: 47–55 (1988).
Zhang et al., Proc. Natl. Acad. Sci. USA 91: 8447–8451 (1994).
Protein Engineering, Alan R. Liss, Inc., New York Table of Contents only.

* cited by examiner

Primary Examiner—Marjorie Moran
(74) Attorney, Agent, or Firm—Foley & Lardner

(57) ABSTRACT

A tumor necrosis factor-α converting enzyme (TACE) is produced, purified, and crystallized. The three-dimensional coordinates of the crystal are obtained by X-ray diffraction. The coordinates can be recorded on a computer readable medium, or are part of a video memory, where they can be used as part of a system for studying for studying TACE. The coordinates are also used in designing, screening, and developing compounds that associate with TACE.

10 Claims, 7 Drawing Sheets

(2 of 7 Drawing Sheet(s) Filed in Color)

```
ADAM_CROAD                        ......EQNL PQRYIELVVV ADRRVFMKYN .SDLNIIRTR
TACE       205 PEELVHR... .VKRRADPDP MKNTCKLLVV ADHRFYRYMG RGEESTTTNY 250
hADAM10        QEKHAINGPE LLRKRRTTSA EKNTCQLYIQ TDHLFFKYYG TRE..AVIAQ

ADAM_CROAD     VHEIVNIINE FYRSL..... ...NIRVSLT DLEIWSGQDF I......TI.
TACE       251 LIELIDRVDD IYRNTSWDNA GFKGYGIQIE QIRILKSPQE VKPGEKHYNM 300
hADAM10        ISSHVKAIDT IYQTT..DFS GIRNISFMVK RIRINTTADE KDPTNPF...

ADAM_CROAD     ......QSSSSNTLNS FGEWRERVLL TRKRHDNAQL LTAINFEGKI
TACE       301 AKSYPNEEKD AMDVKMLLEQ FSFDIAEEAS ..KVCLAHL FTYQDFDMGT 347
hADAM10        ..RFPN.... .ISVEKFLE. ..LNSEQNHD ...DYCLAYV FTDRDFDDGV

ADAM_CROAD     IGKAYTS... .....SMCNP .......... .RSSVGIVKD HSP....INL
TACE       348 LGLAYVGSPR ANSHGGVCPK AYYSPVGKKN IYLNSGLTST KNYGKTILTK 397
hADAM10        LGLAWGAP.  SGSSGGICEK SKLYSDGKKK .SLNTGIITV QNYGSHVPPK

ADAM_CROAD     LVAVTMAHEL GHNLGMEHDG K...DCLRG .......AS LCIMRPGLTP
TACE       398 EADLVTHEL GHNFGAEHDP DGLAECAPNE D......QGG KYVMYPIAVS 441
hADAM10        VSHITFAHEV GHNFGSPHDS G..TECTPGE SKNLGQKENG NYIMYARATS

ADAM_CROAD     GRS...YEFS DDSMGYYQKF LNQYKPQCIL NKP....... ..........
TACE       442 GDHENNKMFS NCSKQSIYKT IESKAQECFQ ER.SNKVCGNS RVDEGEECDP 491
hADAM10        GDKLNNNKFS LCSIRNISQV LEKKRNNCFV ESGQPICGNG MVEQGEECDC
```

FIGURE 3

CRYSTALLINE TNF-α-CONVERTING ENZYME AND USES THEREOF

INFORMATION ON RELATED APPLICATIONS

This application claims the priority benefit of U.S. provisional patent application serial No. 60/073,7,09, filed Feb. 4, 1998, U.S. provisional patent application No. 60/135,499, filed Mar. 30, 1998, and U.S. provisional patent application No. 60/117,476, filed Jan. 27, 1999.

BACKGROUND OF THE INVENTION

The cytokine tumor necrosis factor-α (TNFα) plays a role in the induction of inflammatory reactions and is known to be cytotoxic towards tumor cells. TNFα, however, also may cause severe damage to the human body when produced in excess by eventually leading to multiple organ failure and death. See Bemelmans et al., "Tumor Necrosis Factor: Function, Release and Clearance," *Crit. Rev. Immun.* 16: 1–11 (1996).

Tumor necrosis factor-α is produced by activated cells, such as mononuclear phagocytes, T-Cells, B-Cells, mast cells and NK cells. TNFα exists in two forms: a type II membrane protein having a relative molecular mass of 26 kD and a soluble 17 kD form generated from the membrane form by proteolytic cleavage. The TNFα membrane protein is synthesized as a 223 amino acid membrane-anchored precursor. The soluble TNFα is released from the membrane-bound precursor by a membrane-anchored proteinase. This proteinase was recently identified as a multi-domain metalloproteinase called TNFα-converting enzyme (TACE). See, Black et al., "A metalloproteinase disintigrin that releases tumor-necrosis factor-α from cells," Nature 385. 729–733 (1997), Moss et al., "Cloning of a disintigrin metalloproteinase that processes precursor tumor-necrosis factor-α," Nature 385: 733–736 (1997). TACE has recently been identified as a zinc endopeptidase consisting of an extracellular region comprising an N-terminal signal peptide, a pro-domain, a 263 residue catalytic domain (TCD) that is preceded by a furin cleavage site (residues 211–214), a disintegrin domain, an EFF-like domain, and a crambin-like domain, an apparent transmembrane helix and the intracellular C-terminal tail. Tumor necrosis factors converting enzyme (TACE), including a polynucleotide sequence, is described in detail in the published PCT application No. WO 96/41624, herein incorporated in the entirety by reference.

As noted above, the over-production or unregulated production of TNF-α presents serious physiological dangers. It has been implicated in various deleterious physiological diseases such as rheumatoid arthritis, cachexia and endotoxic shock. It also may eventually lead to organ failure and death. Thus, a way to control or block release of TNFα into the circulation is needed. Because of TACE's role in the conversion of TNFα, inhibition, modulation, or regulation of TACE would affect the release of TNFα into circulation. Inhibitors of metalloproteinases and structure based design thereof are described in Zask et al., "Inhibition of Matrix Metalloproteinases: Structure Based Design" *Current Pharmaceutical Design*, 2:624–661 (1996). Thus, compounds that associate with TACE, such as inhibitors, receptors or modulators will be useful to protect patients from adverse effects associated with the over-production or unregulated production of tumor necrosis factor-α.

SUMMARY OF THE INVENTION

According to one aspect of the invention, there is provided a composition comprising a polypeptide in crystalline form, wherein the polypeptide is a TNF-α-converting enzyme polypeptide. In one embodiment, the TNF-α-converting enzyme polypeptide comprises the TNF-α-converting enzyme catalytic domain. In another embodiment, the TNF-α-converting enzyme polypeptide is the expression product of a polynucleotide encoding the pro and catalytic domains of TNF-α-converting enzyme. In a further embodiment, the TNF-α-converting enzyme polypeptide is the expression product of a polynucleotide encoding the amino acid residues 1–477 of TNF-α-converting enzyme. In yet another embodiment, the polynucleotide is substituted such that amino acid residue Ser266 is changed to Ala and amino acid residue Asn542 is changed to Gln, and wherein a second polynucleotide encoding the sequence Gly-Ser-(His)$_6$ (SEQ ID NO: 2) is fused to the C-terminus.

According to another aspect of the invention, the compositions above further comprising a binding partner suitable for co-crystallization with the TNF-α-converting enzyme polypeptide. In one embodiment, the binding partner is a hydroxamate-based binding partner. In another embodiment, the binding partner is N-{D,L-2-(hydroxyaminocarbonyl)methyl-4-methylpentanoyl}-L-3-amino-2-dimethylbutanoyl-L-alanine,2-(amino)ethyl amide.

According to further embodiments, the compositions above have a crystal structure diffracting to 2.0 Å, are monoclinic, have a unit cell comprising four crystallographically independent TNF-α-converting enzyme catalytic domain (TCD) molecules, have the TCD molecules are in an asymmetric unit, and/or have monoclinic space group $P2_1$ and the cell has the constants a=61.38 Å, b=126.27 Å, c=81.27 Å, and β=107.41°.

In still another embodiment of the invention, the polypeptides above are characterized by the structure coordinates according to Table 1, or a substantial part thereof.

According to a further aspect of the invention, there is provided a method for crystallizing a TNF-α-converting enzyme polypeptide, comprising (A) mixing a solution comprising a TACE polypeptide and a binding partner with a crystallization buffer, and (B) crystallizing the mixture of step (A) by drop vapor diffusion to form a crystalline precipitate. In one embodiment, the method further comprises (C) transferring seeds from the crystalline precipitate formed by the drop vapor diffusion and a crystallization promotor into a mixture of a concentrated solution comprising a TACE polypeptide and binding partner substrate, and a crystallization buffer, and (D) crystallizing the mixture of step (C) by drop vapor diffusion to form a crystal. In another embodiment, the crystallization buffer is 0.1M Na Citrate pH 5.4, 20% w/v PEG 4000, and 20% v/v Isopropanol. In still another embodiment, the binding partner is N-{D,L-2-(hydroxyaminocarbonyl)methyl-4-methylpentanoyl}-L-3-amino-2-dimethylbutanoyl-L-alanine, 2-(amino)ethyl amide. In yet another embodiment, crystallization is at a temperature ranging from 4 to 20 degrees Celsius. In another embodiment, the solution comprising the TACE polypeptide and the inhibitor is at a concentration of about 5 mg/mL to about 12 mg/mL in a buffer. In a further embodiment, the solution comprising a TACE polypeptide and the binding partner is mixed with the crystallization buffer in a 1:1 ratio.

According to still another aspect of the invention, there is provided a tumor necrosis factor-α (TNF-α)-converting enzyme crystal made by co-crystallizing a TNF-α-converting enzyme polypeptide with a co-crystallization substrate.

According to yet another aspect of the invention, there is provided a computer-readable medium having recorded thereon x-ray crystallographic coordinate data for the catalytic domain of TNF-α converting enzyme, or a portion thereof. In one embodiment, the computer-readable medium has recorded thereon the x-ray crystallographic coordinate data set forth in Table 1, or a portion thereof. In another embodiment, the medium is selected from the group consisting of a floppy disc, a hard disc, computer tape, RAM, ROM, CD, DVD, a magnetic disk, and an optical disk. In still another embodiment, the computer-readable medium has recorded thereon machine-readable data, wherein the computer-readable medium, when used in conjunction with a machine programmed with instructions for using the data, is capable of generating image signals for depicting a graphical, three-dimensional representation of a TNF-α converting enzyme polypeptide, or portion thereof.

According to a further aspect of the invention, there is provided a system for studying a TNF-α converting enzyme polypeptide, said system comprising (a) a memory capable of storing information representing at least a portion of a TNF-α converting enzyme polypeptide, wherein said memory comprises at least one first-type storage region, including a set of spatial coordinates specifying a location in a three dimensional space, and at least one second-type storage region comprising information representing a characteristic of one of a plurality of amino acids, said second-type storage regions being logically associated with said first-type storage regions in said memory to represent a geometric arrangement of at least one characteristic of said at least a portion of said TNF-α converting enzyme peptide in said three dimensional space; (b) a processor coupled to said memory to access said first-type storage regions and said second-type storage regions, wherein the processor generates image signals for depicting a visual image representing three dimensional image of said at least one characteristic of said at least a portion of said TNF-α converting enzyme polypeptide in said three dimensional space based on data from said memory; and (c) a display coupled to said processor to receive said image signals, wherein the display depicts a visual three dimensional image of said at least one characteristic of said at least a portion of said TNF-α converting enzyme polypeptide in said three dimensional space based on said image signals. In one embodiment of the invention, the image signals include signals for depicting a visual three dimensional image of a ribbon structure of said at least a portion of said TNF-α converting enzyme polypeptide in said three dimensional space. In another embodiment of the invention, the image signals include signals for depicting a visual image of a solid model representation of said at least a portion of said TNF-α converting enzyme polypeptide in said three dimensional space. In still another embodiment of the invention, the image signals include signals for depicting a visual three dimensional image of electrostatic surface potential of said at least a portion of said TNF-α converting enzyme polypeptide in said three dimensional space. In yet another embodiment of the invention, the image signals include signals for depicting a visual three dimensional stereo image of said at least a portion of said TNF-α converting enzyme polypeptide in said three dimensional space. In a further embodiment of the invention, the system further comprises a storage device capable of storing data representing a geometric arrangement of a characteristic of a composition other than said TNF-α converting enzyme polypeptide; and an operator interface for receiving instructions from a operator; and wherein said processor is coupled to said storage device and to said operator interface and generates additional image signals for depicting said geometric arrangement of said characteristic of said composition relative to said visual three dimensional image of said at least one characteristic of said at least a portion of said TNF-α converting enzyme polypeptide on said display based on instructions from the operator interface. In one embodiment, the storage device is part of said memory. In another embodiment, the system comprises a plurality of first-type and second-type storage regions.

According to another aspect of the invention, there is provided a video memory capable of storing information for generating a visual display of at least a portion of a TNF-α converting enzyme polypeptide, said video memory comprising (a) at least one first-type storage region, each of said first-type storage regions including a set of spatial coordinates specifying a location in a three dimensional space; and (b) at least one second-type storage region, each of said second-type storage regions containing information for visually depicting a characteristic of one of a plurality of amino acids; wherein said second-type storage regions are logically associated with said first-type storage regions in said video memory to represent a geometric arrangement of at least one characteristic of said at least a portion of said TNF-α converting enzyme polypeptide in said three dimensional space. In one embodiment, the second-type storage regions are logically associated with said first-type storage regions in said video memory to represent a geometric arrangement of at least one characteristic of a catalytic domain portion of said TNF-α converting enzyme polypeptide in said three dimensional space. In another embodiment, the first-type storage regions and said second-type storage regions are regions of a semiconductor memory. In yet another embodiment, the first-type storage regions and said second-type storage regions are regions of an optical disk. In still another embodiment, the first-type storage regions and said second-type storage regions are regions of a magnetic memory. In a further embodiment, the video memory comprises a plurality of first-type and second-type storage regions.

In a still further aspect of the invention, there is provided a method of identifying a compound that associates with TNF-α-convening enzyme, comprising (A) designing an associating compound for said polypeptide that forms a bond with the TNF-α-converting enzyme catalytic domain based on x-ray diffraction coordinates of a TNF-α-converting enzyme polypeptide crystal; (B) synthesizing said compound; and (C) determining the associate capability of said compound with said TNF-α-converting enzyme. In one embodiment, the associating compound is an inhibitor, mediator, or other compound that regulates TNF-α-converting enzyme activity. In another embodiment, the associating compound is a competitive inhibitor, un-competitive inhibitor, or non-competitive inhibitor. In still another embodiment, the coordinates are the coordinates of Table 1, or a substantial part thereof. In a further embodiment, the TNF-α-converting enzyme polypeptide crystal comprises the TNF-α-converting enzyme catalytic domain. In still another embodiment, the TNF-α-converting enzyme polypeptide is the expression product of a polynucleotide encoding the pro and catalytic domains of TNF-α-converting enzyme. In yet another embodiment, the TNF-α-converting enzyme polypeptide is the expression product of a polynucleotide encoding the amino acid residues 1–477 of TNF-α-converting enzyme. In another embodiment, the polynucleotide is substituted such that amino acid residue Ser266 is changed to Ala and amino acid residue Asn542 is changed to Gln, and wherein a second polynucleotide encoding the sequence Gly-Ser-(His)₆ (SEQ ID NO: 2) is fused to the C-terminus. In a further embodiment, the TNF-α-converting enzyme polypeptide crystal is co-crystallized with a binding partner. In still another embodiment, the binding partner is a hydroxamate-based binding partner or N-{D,L-2-(hydroxyaminocarbonyl)methyl-4-methylpentanoyl}-L-3-amino-2-dimethylbutanoyl-L-alanine,2-(amino)ethyl amide. In yet other embodiments, the TNF-α-converting enzyme polypeptide crystal has a crystal structure diffracting to 2.0 Å, is monoclinic, has a unit cell comprising four crystallographically independent TNF-α-converting enzyme catalytic domain (TCD) molecules, has the TCD molecules are in an asymmetric, unit, and/or is of monoclinic space group P2₁ and the cell has the constants a=61.38 Å, b=126.27 Å, c=81.27 Å, and β=107.41°. In still another embodiment, the invention the associating compound is designed to associate with the S1' region of TNF-α-converting enzyme. In yet another embodiment, the associating compound is designed to associate with the S1'S3' pocket of TNF-α-converting enzyme. In still other embodiments of the invention, the associating compound is designed to (i) incorporate a moiety that chelates zinc, (ii) form a hydrogen bond with Leu348 or Gly349 of TNF-α-converting enzyme, (iii) introduce a non-polar group which occupies the S1' pocket of TNF-α-converting enzyme, (iv) introduce a group which lies within the channel joining S1'-S3' pockets of TNF-α-converting enzyme and which makes appropriate van der Waal contact with the channel, and/or (v) form a hydrogen bond with Leu348 or Gly349 on the backbone amide groups of TNF-α-converting enzyme.

These and other aspects of the invention will become apparent to the skilled artisan in view of the teachings contained herein.

BRIEF DESCRIPTION OF THE FIGURES

The file of this patent contains at least one drawing executed in color. Copies of this patent with color drawings are provided to the Patent and Trademark Office with payment of the necessary fee.

FIG. 1 is a ribbon diagram of the TACE catalytic domain (TCD). The chain starts on the lower left back side, runs through the structural elements sI, hAI, hA, sII, hB, hB2, sIII, IV, IVa, sIVb, sV, hC, Met-turn and hD, and ends in the upper left back. The three disulfides are shown as connections, with the sulphurs given as small spheres. The catalytic zinc (central sphere) is liganded by the three imidazoles of His405, His409 and His415, and by the hydroxyl and the carbonyl oxygen atoms of the inhibitor hydroxamic acid group. The inhibitor mimicking interaction of primed-site residues of a peptide substrate is shown in full. FIG. 1 was made using SETOR. See Evans, S. "SETOR: Hardware Lighted Three-Dimensional Solid Model Representations of Macromolecules" *J. Mol. Graph.* 11:134–138 (1993).

FIGS. 2a and 2b are solid surface representations of the catalytic domains of TACE (TCD) (FIG. 2a) and MMP-3 (FIG. 2b). The electrostatic surface potential is contoured from −15 (intense red) to 15 (intense blue) k₈T/e. Both active-site clefts run from left to right, with the catalytic zinc atoms (spheres) in the centers. In TACE, the bound inhibitor is shown in full structure, binding with its isobutyl (P1') and its Ala (P3') sidechains into the deep S1' and the novel S3' pockets. The orientation is similar to FIG. 1. FIGS. 2a and 2b were made using GRASP. Nicolls, A., Bharadwaj, R. and Houig, B., "Grasp—Graphical representation and analysis of surface properties," *Biophys.* 64, A166 (1993).

FIG. 3: FIG. 3 aligns the catalytic domain sequences of adamalysin II (ADAM_CROAD) (SEQ ID NO: 4), TACE (SEQ ID NO: 5) and human ADAM 10 (hADAM1O) (SEQ ID NO: 6), according to their topological equivalence and sequence similarity, respectively. The residue numbers are due to the generic TACE numbering. Arrows and braces represent β-strands and α-helices in TACE.

FIG. 4 is a stereo section of the final 2.0 Å electron density around the catalytic zinc (large, central sphere) superimposed with the final TACE model. Visible are the three zinc liganding imidazole rings of His405 (top), His409 (left) and His415 (bottom), the "catalytic" Glu406, and the hydroxamic acid moiety of the inhibitor. The orientation is similar to FIG. 1. FIG. 4 was made using TURBO-FRODO. See Roussel, A. & Cambilleau, C., "Turbo-Frodo in Silicon Graphics Geometry," *Partners Directory,* Silicon Graphics, Mountain View, Calif. (1989).

FIG. 5 is a superposition of the ribbon plots of the catalytic domain of TACE (light) and adamalysin (dark). Also shown is the catalytic zinc of TACE (sphere) and the three (TACE) and two (adamalysin) disulfide bridges. The orientation is similar to FIG. 1. FIG. 5 was made using GRASP.

FIG. 6 illustrates a system for studying a TNF-α converting enzyme, including a video memory storing information for generating a visual display of at least a portion of a TNF-α converting enzyme.

DETAILED DESCRIPTION OF THE INVENTION

Figure 1:
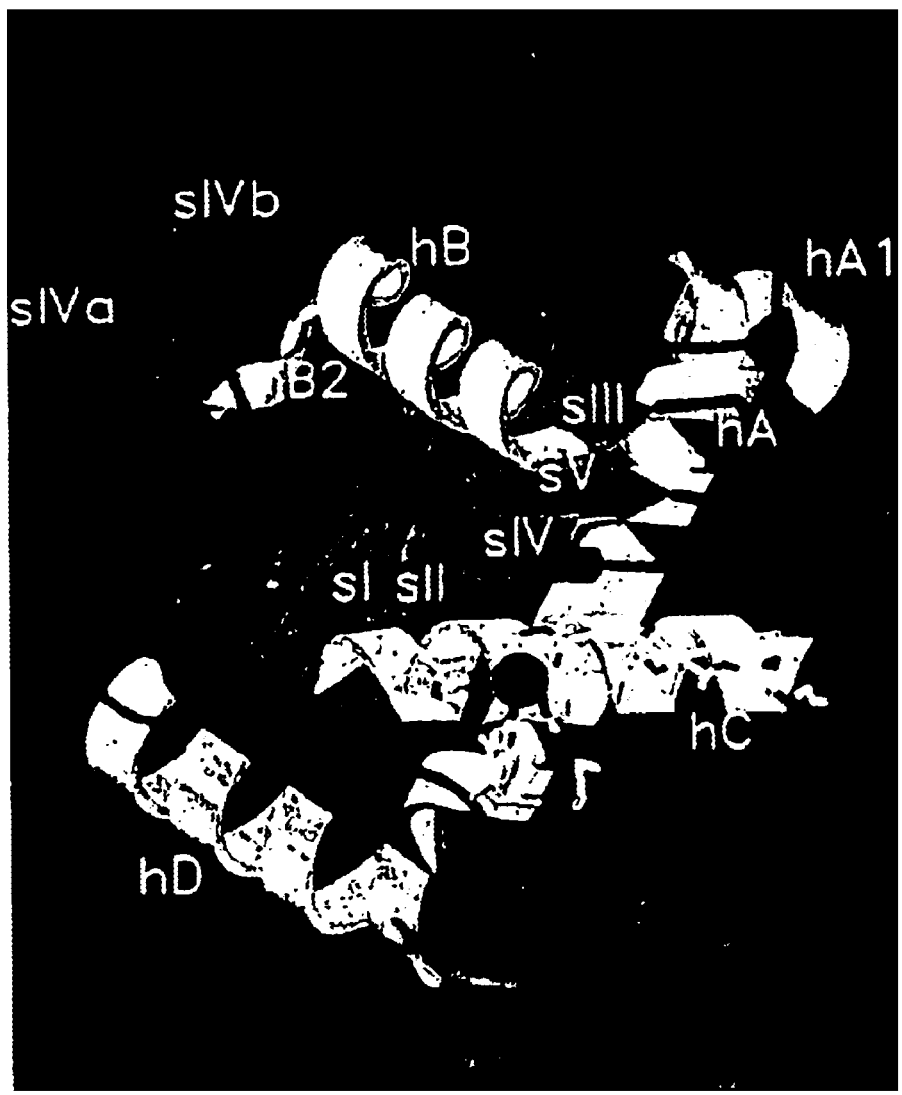
FIG. 1.

The present invention relates to a highly purified tumor necrosis factor-α converting enzyme (TACE) polypeptide, a method of producing and purifying a TACE polypeptide, a method of crystallizing a TACE polypeptide, and a TACE polypeptide crystal. The invention further relates to a X-ray diffraction method using a TACE polypeptide crystal, and to a method of obtaining the X-ray crystallographic structural coordinates of a TACE polypeptide as well as the structural coordinates themselves. Still further, the present invention relates using the structural coordinates of a TACE polypeptide to elucidate the three-dimensional structure of a TACE polypeptide and designing and developing compounds that associate with TACE. Knowledge of the three-dimensional structure and structure coordinates provided according to the invention permit the skilled person to make compounds that will interact with TACE. Such interacting compounds can be made by a variety of techniques and design criteria, including those disclosed in *Protein Engineering* (Oxender and Fox, eds.) (Alan R. Liss, Inc. 1987).

As used herein, TACE refers to a group of polypeptides that are capable of converting the 26 kD cell membrane-bound form of TNF-α into the soluble 17 kD form that comprises the C-terminal 156 residues of the TNFα protein. TACE encompasses proteins having the amino acid sequence described in PCT application No. WO 96/41624, herein incorporated in its entirety by reference, as well as any of those proteins having homology, preferably no less than 50%, more preferably at least 80% homology, still more preferably 90% homology to such sequence, at the amino acid level. Additionally, TACE further refers to the expression products of nucleotide sequences disclosed in PCT application No. WO 96/41624. TACE further encompasses the membrane-bound protein and soluble or truncated proteins comprising the extracellular portion of the protein and which retain biological activity and are capable of being secreted. Examples of such proteins are described in PCT application No. WO 96/41624.

The TACE amino acid sequence, or any part or residue thereof, can be found in Black et al., "A Metalloproteinase disintigrin that releases tumour-necrosis factor-α from cells," *Nature* 385: 729–733 (February 1997), herein incorporated in the entirety by reference. Variations in the amino acid sequence of TACE are within the present invention as well. All references to the TACE amino acid sequence contained herein refer to the sequence in Black et al., supra.

As used herein, the TACE catalytic domain (TCD) refers to the portion of a TACE polypeptide between residues 215 and 477 and including the preceding furin cleavage site (residues 211–214), or any part thereof that is capable of cleaving the peptide PLAQAVRSSS (SEQ ID NO: 1).

Expression, Isolation and Purification of TACE Polypeptides

Tumor necrosis factor-α converting enzyme (TACE) is described in the published PCT application No. WO 96/41624. The application describes isolated nucleic acids encoding TACE or portions of TACE, expression vectors comprising a cDNA encoding TACE or portions thereof, and host cells transformed or transfected with the expression vectors comprising a cDNA encoding TACE or portions of TACE. The application further describes processes for producing TACE and portions thereof, for example by culturing transfected cells engineered to express TACE, followed by purification of the recombinantly produced TACE or portion thereof. Methods of isolating, expressing, and purifying a TACE polypeptide are described in detail in published PCT application No. WO 96/41624. The entirety of PCT 96/41624 is incorporated herein by reference.

According to the invention, cDNA encoding the signal peptide, pro and catalytic domains of TACE, i.e., amino acid residues 1–477 is inserted into a suitable expression vector and expressed in a suitable cell line. The cDNA also may include other regions that facilitate expression or achieve other objects that otherwise that do not depart from the essence of the invention, such as flanking regions.

The cDNAs encoding the TACE polypeptide, or functional portions thereof, such as the TCD, may be altered by addition, substitution, deletion, or insertion. Such alterations may be made, for example, to prevent glycosolation, prevent formation of incorrect or undesired disulfide bridges, and/or enhance expression. Examples of such alterations are described in WO 96/41624 and can be carried out by the methods described therein and other conventional methods. TACE may also be conjugated. Such conjugates may comprise peptides added to facilitate purification and/or identification. Such peptides include, for example, poly-His peptides. Conjugation is described in U.S. Pat. No. 5,011,912 and Hopp et al., *Bio/Technology* 6:1204 (1988).

In one embodiment of the invention, the cDNA encodes a TNF-α converting enzyme polypeptide comprising the signal peptide, pro and catalytic domains of TACE (TCD), residues 1–477, with Ser266 changed to Ala and Asn452 changed to Gln. These substitutions are useful in preventing N-linked glycosolation. Additionally, the sequence Gly-Ser (His)$_6$ (SEQ ID NO: 2) may be added to the C-terminus. The addition of the sequence Gly-Ser(His)$_6$ (SEQ ID NO: 2) facilitates purification of the polypeptide using metal-chelate affinity resins, such as Ni-NTA resins.

Recombinant expression vectors containing the nucleotide sequence encoding TACE, or a portion thereof, may be prepared using well known methods. Suitable host cells for expression of TACE polypeptides include prokaryotic, yeast, and higher eukaryotic cells. Vectors and host cells suitable for use in the present invention are described in WO 96/41624. Further examples of suitable expression systems that can be employed to express recombinant TACE according to the present invention include mammalian or insect host cell culture expression systems, including baculovirus systems in insect cells (See Luckow and Summers, *Bio/Technology* 6:47 (1988))and mammalian cell lines such as COS-7 cells (Gluzman et al., *Cell* 23:175 (1981)). Additional examples are known in the art and include those described in WO 96/41624. In one embodiment of the invention, the TACE polypeptide is expressed in CHO cells. In this embodiment, the cells secrete a mixture of TACE polypeptide beginning with Val212 and Arg215.

In one embodiment, stable expressing cells may be selected by culturing the cells in a drug that kills those cells that do not incorporate the vector. Examples of suitable selection methods are described in, for example, Kaufman, R. J., "Selection and coamplification of heterologous genes in mammalian cells," *Methods in Enzymology*, 185:537–566 (1990).

Purification of the expressed TACE polypeptide may be carried out by any suitable means, such as those described in WO 96/41624. According to one aspect of the invention, it is preferable to obtain a TACE polypeptide that is suitable for crystallization. In obtaining a TACE polypeptide suitable for crystallization, it is important that the process for purifying the TACE polypeptide is sufficient to yield a polypeptide pure enough to properly crystallize.

A preferred method of purification starts with a suitable amount of medium from the culture of TACE-secreting cells. This medium is generally a supernate of the culture. The medium contains the TACE polypeptide to be purified. Preferably, the TACE polypeptide is recombinantly produced using DNA coding for the TACE polypeptide with the sequence altered to encode a conjugate or conjugates that facilitate purification. For example, the sequence encoding Gly-Ser-(His)$_6$ (SEQ ID NO: 2) may be added to the C-terminus to facilitate purification using metal-chelate resins.

The medium is concentrated, for example, by diafiltration. Suitable diafiltration units include a Millipore 10K cut-off, 1 ft$^2$ TFF diafiltration unit. A suitable buffer solution is then added to the concentrated medium. Any suitable buffer may be used. One such suitable buffer contains 20 mM Tris (pH 7.5) and 300 mM NaCl.

The sample is reconcentrated and diluted numerous times. For example, the sample may be reconcentrated and diluted a second time with the buffer, reconcentrated again, diluted a third time with the buffer, and reconcentrated a final time. The sample retained in the diafiltration unit is recovered by a suitable method, such as by a back-flush method. The recovered material may then be filtered through a suitable membrane. Suitable membranes include, for example, 0.45 or 0.22 micron pore-size membranes. Azide is then added. The filtered sample may then be stored overnight at a low temperature, such as about 2–9° C. After overnight storage, imidazole from a stock solution in water and ZnCl$_2$ from a stock solution in water are added to the filtered sample. The sample then is pumped over a suitable column. One suitable column, particularly when the TACE polypeptide is conjugated with the sequence Gly-Ser-(His)$_6$, is a metal-chelate resin, such as a Ni-NTA resin.

The column is washed with a buffer, such as a buffer of 20 mM Tris pH 7.5, 300 mM NaCl, 5 mM imidazole, and 5 uM ZnCl$_2$. The TACE polypeptide is then eluted with an increasing gradient of imidazole. Fractions are collected in tubes containing glycerol in water Tris pH 8. Preferably, the glycerol solution is prepared the day of the column run.

An aliquot from each fraction is spotted on a membrane which is stained with amido black to determine which fractions contain a significant amount of protein. Alternatively, a small amount, for example 5 μl, from each fraction may be used for gel analysis using Coomassie staining. The fractions with a significant amount of protein are pooled, and the pool is then concentrated with, for example, a diafiltration unit.

In some cases, aggregation of polypeptide may occur. In order to eliminate aggregates and further facilitate purification, an inhibitor of TACE, such as a hydroxamate-based inhibitor, may be added to the concentrated sample from a stock solution in water, and octylglucoside (commercially available from Boehringer Mannheim) is added from a stock solution in water. The sample is then incubated at room temperature for 15–24 hours.

Following incubation, the sample is applied to a size exclusion column. The column is first equilibrated with a suitable buffer, such as a buffer of 10 mM Tris pH 7.5, 100 mM NaCl, 10% glycerol. Suitable size exclusion columns include, for example, LKB 2135-365, packed with TSK-G3000 SWG or the like such as Superdex-200. The buffer is then pumped through the column. The highly purified TACE polypeptide can be detected by absorption at 280 nm.

A gel analysis of all fractions with significant protein is carried out to determine which fractions should be pooled. The size exclusion chromatography pool is concentrated using, for example, a diafiltration unit.

A binding partner, such as an inhibitor, may then be added to the purified sample. The binding partner is particularly useful in stabilizing the TACE polypeptide. The binding partner may be any suitable compound. Suitable binding partners include, for example, hydroxamate-based inhibitors. One suitable inhibitor is N-{D,L-2-(hydroxyaminocarbonyl)methyl-4-methylpentanoyl}-L-3-amino-2-dimethylbutanoyl-L-alanine, 2-(amino)ethyl amide. This inhibitor, as well as other inhibitors, are described in U.S. Pat. No. 5,594,106 (Black et al.), herein incorporated in its entirety by reference.

The protein complex can be stored at low temperature, for example, at about 4° C.

TACE Crystal and Methods of Crystallization of TACE Polypeptides

One aspect of the invention relates to a method of crystallizing a TACE polypeptide. A preferred method comprises co-crystallizing a TACE polypeptide with a binding partner described above. Exemplary means for obtaining the TACE polypeptide, as well as purification of the polypeptide are described above.

Crystals may be grown or formed by any suitable method, including drop vapor diffusion, batch, liquid bridge, and dialysis, and under any suitable conditions. Crystallization by drop vapor diffusion is often preferable. In addition, those of skill in the art will appreciate that the crystallization conditions may be varied. Various methods of crystallizing polypeptides are generally known in the art. See, for example, WO 95/35367, WO 97/15588, EP 646 599 A2, GB 2 306 961 A, and WO 97/08300.

In one embodiment of the invention, a DNA construct comprising TACE residues 1–477, with Ser266 changed to Ala, Asn452 changed to Gln, and the sequence Gly-Ser-(His)$_6$ (SEQ ID NO: 2) added to the C-terminus, may be expressed in CHO cells. These cells primarily secrete a processed mixture of TACE, about half beginning with Val212 and about half with Arg215. The mixture is purified as described above. The purified TACE polypeptide, with the added binding partner, is stored in a buffer as described above.

The TACE polypeptide and binding partner are co-crystallized. The TACE/binding partner solution, at a polypeptide concentration of about 5 mg/mL to about 12 mg/mL in a TACE buffer described above, is mixed with a suitable crystallization buffer and crystallized using a suitable crystallization technique, for example drop vapor diffusion. Suitable crystallization buffers, for example, include: 0.1 M Na Acetate pH 5.3, 0.2 M CaCl$_2$, 30% v/v Ethanol; 0.1 M Na Citrate pH 5.0, 40% v/v Ethanol; 0.1 M Na Citrate pH 8.7, 20% w/v PEG 4000, 20% v/v Isopropanol; and 0.1 M Na Citrate pH 5.4, 20% w/v PEG 4000, 20% v/v Isopropanol. The sample is incubated at a temperature ranging from about 4 to 20 degrees Celsius. A crystalline precipitate is formed.

Seeds from the crystalline precipitate obtained, as whole crystals or crushed crystal suspensions, are transferred, along with a suitable crystallization promoter, such as hair of rabbit, to a solution of concentrated TACE/substrate in a crystallization buffer. Crystals suitable for X-ray data collection are formed.

Another aspect of the invention relates to a TACE polypeptide crystal. One such crystal comprises a TNF-α converting enzyme catalytic domain (TCD) polypeptide co-crystallized with an inhibitor. The crystal diffracts to about 2 A and belongs to the monoclinic space group P2$_1$. The crystal's unit cell comprises four crystallographically independent TCD molecules. The TCD molecules are in an asymmetric unit and are not clustered into separate tetrameres, but are integrated into the infinite periodic structure. The crystal has the cell constants: a=61.38 Å (angstrom), b=126.27 Å, C=81.27 Å and β=107.41°.

X-Ray Diffraction

Another aspect of the invention relates to the structure of TACE, particularly the structure of the TACE catalytic domain (TCD). The structure of TACE can be determined utilizing a crystal comprising a TACE polypeptide as described above. According to the present invention, the structure of TACE, and particularly the TCD, is determined using X-ray crystallography. Any suitable X-ray diffraction method for obtaining three-dimensional structural coordinates of a polypeptide may be used. The three-dimensional structure coordinates, or any part thereof that characterizes the part of the TACE polypeptide of interest, such as the TACE catalytic domain or part thereof that is capable of cleaving the peptide PLAQAVRSSS (SEQ ID NO: 1), can be used as described herein.

Methods of Using TACE X-Ray Diffraction Coordinates

The invention also relates to use of the structure coordinates obtained from the above described X-ray diffraction studies of the TACE catalytic domain. The coordinates may be utilized, by direct analysis, with the aide of computers, or combinations thereof, to determine the structure, including secondary and tertiary structure, of the TACE catalytic domain. The TACE catalytic domain structure coordinates also may be used to develop, design, and/or screen compounds that associate with TACE. As used herein, "associate" means that the compound may bind to or interact with TACE ionically, covalently, by hydrogen bond, van der Waals interaction, salt bridges, steric interaction, hydophilic interactions and hydrophobic interaction. Moreover, the term "associate" encompasses associations with any portion of the TACE catalytic domain. For example, compounds that associate with TACE may be compounds that act as competitive inhibitors, un-competitive inhibitors, and non-competitive inhibitors. Compounds that associate with TACE also may be compounds that act as mediators or other regulatory compounds. Compounds that associate with TACE also may be compounds that isomerize to short-lived reaction intermediates in the chemical reaction of substrate with TACE. In particular, compounds designed to associate with TACE may be used therapeutically as inhibitors, mediators and other regulatory compounds.

The use of X-ray coordinates for structure determination, molecular design and selection and synthesis of compounds that associate with other polypeptides is known in the art. Published PCT application WO 95/35367 describes the use of X-ray structure coordinates to design, evaluate, synthesize and use compounds that associate with the active site of an enzyme. UK Patent Application 2306961A describes the use of X-ray coordinates in rational drug design. Published PCT application, WO 97/15588 describes the structural determination of a polypeptide using x-ray diffraction patterns as well as use of the coordinates and three-dimensional structure in finding compounds that associate with the polypeptide of interest. This invention, however, for the first time allows the use of X-ray coordinates for a TACE polypeptide for structural determination, molecular design, and selection and synthesis of compounds that associate with TACE.

In one aspect of the invention, the structure coordinates obtained by the foregoing methods may be displayed as, or converted to, a graphical representation, including three-dimensional shape representations. This may be accomplished using commercially available computer programs capable of generating graphical representations of molecules, or parts thereof, from a set of structural coordinates. Examples of computer programs capable of generating graphical representations of molecules, or parts thereof, from a set of structural coordinates are described in published PCT application WO 97/08300, incorporated in the entirety by reference.

In another aspect of the invention, the structure coordinates and structure may be compared to, or superimposed over, other similar molecules, such as other metalloproteinases. For example, the TACE structure coordinates and structure may be compared to or superimposed over the structure coordinates or structure of snake venom metalloproteinases, such as, for example, adamalysin II. The TACE structure coordinates and structure also may be compared to or superimposed over the structure coordinates or structure of matrix metalloproteinases, such as ADAM 10, including human ADAM 10. Comparison of TACE and other molecules for which a graphical structure or three-dimensional structural coordinates are available may be carried out with the aide of available software applications, such as the Molecular Similarity application of QUANTA (Molecular Simulations, Inc., Waltham, Mass.).

Compounds that associate with TACE also may be computationally evaluated and designed by screening and selecting chemical entities or fragments for their ability to associate with TACE, and specifically the TACE catalytic domain. Several methods may be used to accomplish this aspect of the invention. In one embodiment, one may visually inspect a computer-generated model of TACE, and specifically the catalytic domain, based on the structure coordinates described herein. Computer generated models of chemical entities or specific chemical moieties can then be positioned in or around the catalytic domain and evaluated based on energy minimization and molecular dynamics, using, for example, available programs such as CHARMM or AMBER. Positioning of the chemical entity or fragment can be accomplished, for example with docking software such as Quanta and Sybyl. Additionally, known and commercially available computer programs may be used in selecting chemical entities or fragments. Once suitable chemical entities or fragments are selected, they may be assembled into a single compound, such as an inhibitor, mediator, or other regulatory compound. Known and commercially available model building software may assist in assembly.

In one aspect of the invention, compounds that associate with TACE and specifically the TACE catalytic domain may be designed as a whole, rather than by assembly of specific chemical moieties or chemical entities. This embodiment may be carried out using computer programs such as LUDI (Biosym Technologies, San Diego, Calif.), LEGEND (Molecular Simulations, Burlington, Mass.), and Leap Frog (Tripos Associates, St. Louis, Mo.).

In one embodiment, a candidate compound is chosen based upon the desired sites of interaction with TACE and the candidate compound in light of the sites of interaction identified previously. Once the specific candidate compound-TACE interactions are determined, docking studies, using commercially available docking software, are performed to provide preliminary "modeled" complexes of selected candidate compound with TACE.

Constrained conformational analysis is performed using, for example, molecular dynamics (MD) to check the integrity of the modeled TACE-inhibitor complex. Once the complex reaches its most favorable conformational state, the structure as proposed by the MD study is analyzed visually to ensure that the modeled complex complies with known experimental SAR/QSAR (structure-activity relationship/quantitative structure-activity relationship) based on measured binding affinities.

Other modeling techniques also may be used in accordance with the invention. Examples of these techniques are disclosed in Cohen et al., "Molecular Modeling Software and Methods for Medicinal Chemistry," *J. Med. Chem.*, 33:883–894 (1990) and Navia et al., "The Use of Structural Information in Drug Design," *Current Opinions in Structural Biology*, 2:202–210 (1992), herein incorporated by reference in the entirety.

Compounds developed or designed to associate with TACE may be optimized or the efficiency of association can be tested using a number of methods known in the art. For example, the deformation energy and electrostatic interactions may be determined and optimized. Known and commercially available software and hardware systems may be used. Examples of such software are disclosed in WO 95/07619. Structure-based analoging for optimization of the inhibitor potency, selectivity and physical drug-like properties in an iterative manner also may be performed by one skilled in the art of drug design.

Substitutions also may be made to selected or designed compounds. These substitutions can be made to improve or modify the association properties of the compound. Such substitutions may be made, for example, in side groups or particular atoms of the compounds. Generally, one should begin with conservative substitutions that have approximately the same size, shape, charge and other characteristics of the original group or atom. Substituted compounds may be further analyzed and optimized as described above.

In a further aspect of the invention, the potential inhibitory, mediatory, regulatory, or other binding effect of a compound may be analyzed and evaluated, using, for example, commercially available computer software, prior to actual synthesis and testing of such compound. In this way, one can evaluate the probability of synthesizing and testing of inoperative compounds.

Procedures for measuring inhibition generally are known in the art and are disclosed, for example, in PCT 96/41624. Such methods include assays based on reaction with a peptide substrate.

TACE Catalytic Domain Structure

The physical features of the TCD, determined based on the X-ray diffraction data obtained using the methods described and its use in creating molecular models of the TCD, are further described, with reference to the Figures.

Figure 2A:
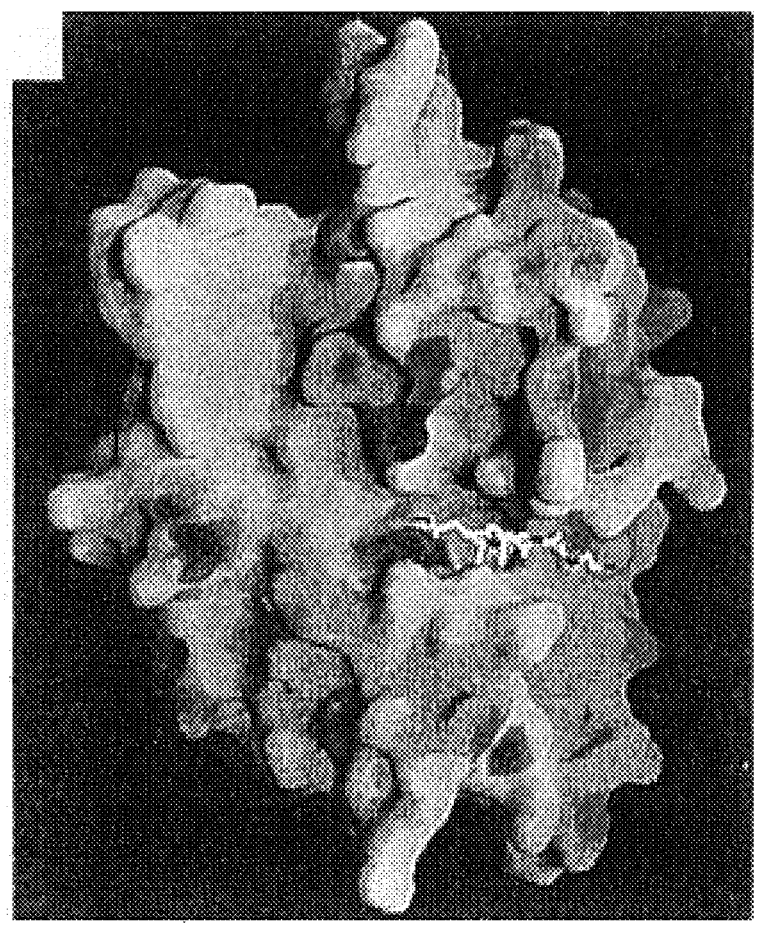
FIGS. 2a and 2b.

The domain depicted in FIG. 1 has the shape of an oblate ellipsoid, notched at its flat side to give a relatively small active-site cleft separating the small "lower" subdomain from the "upper" main molecular body (FIG. 2a). The TCD polypeptide chain starts on the molecular surface (in the lower back, FIG. 1), with the chain becoming well defined between Asp217 and Met221 (see FIG. 3). Central to the molecule is the five-stranded β-pleated sheet, with the β-strands arranged in the order (from back to front, see FIG. 1) sIII, sI, sII, sV and sIV (see FIG. 3), with sIV, the "edge" strand, running antiparallel to the others. This β-sheet is highly twisted flanked by two α-helices (hB and hB2) on its convex and two helices (hA and hC) on its concave side. The β-strands sI and sII are connected by the short α-helix hA1 and the long, α-helix hA (the obliquely running helix on the backside, FIG. 1). The β-strands sII and sIII are linked by the large "multiple-turn loop", the long "intermediate" α-helix hB and the adjacent short α-helix hB2, all of them arranged on "top" of the β-sheet thus fully shielding its central part from bulk water (FIG. 1). The multiple-turn loop is bulged out at two sites giving rise to a "spur-like" and a quite acidic protuberance, respectively (visible in FIG. 2a on top of the molecule). The sIII-sIV linker terminates in a short "bulge", before it enters the edge strand sIV. The sIV-sV connecting segment is dissected into two large "ear-like" surface-located loops, a first one nestling to the main molecular body (giving rise to the "blue" surface, center left, in FIG. 2a), and a long β-hairpin loop (sIIa-sIIb) projecting from the molecular surface (top left in FIGS. 1 and 2). A bulged-out loop links sV with the "active-site helix" hC, which is located in the center of the molecule and stops abruptly at the strictly conserved Gly412, where the chain kinks down to build the lower subdomain.

The C-terminal chain comprising the last 61 TCD residues (FIG. 3) first forms three short straight almost perpendicularly arranged segments linked by two "narrow" supertwisted loops, returns via the tight "Met-turn" Tyr433-Val434-Met435-Tyr436 back to the surface where it kinks at Pro437 to form the Pro437-Ile438-Ala439 outer "wall" of the S1' crevice, approaches in a wide loop the C-terminal α-helix hD and runs through it, and ends up on the molecular "back" surface close to the N-terminus, with the last defined residues Arg473-Ser474 fixed via hydrogen bonds to the main molecular body. Via Cys423-Cys453, the first of the two "narrow" loops is disulfide-linked with the N-terminus of helix hD, whose C-terminal end in turn is clamped to the "ear-like" sIV-sV linker peptide through Cys365-Cys469. Spatially adjacent, the third disulfide bridge of TCD, Cys225-Cys333, connects the N-terminal parts of β-strands sI and sIII. In the intact TACE molecule, four residues downstream of Ser474 would reside Cys478, which is already integral part of the compact elongated disintegrin domain (Saudek et al., "Three-dimensional structure of echistatin, the smallest active RGD protein" *Biochem.* 30, 7369–7372 (1991)). Considering Ser474 and this Cys478 as pivot points of their respective domains, the three residue linker would allow relatively unconstrained docking of the disintegrin domain to the "left" surface side of the catalytic domain.

The active-site cleft of TACE (FIG. 2a) is relatively flat on the left hand (nonprimed) side, but becomes notched towards the right. The catalytic zinc residing in its center is penta-coordinated by the three imidazole Nε2 atoms of His405, His409 and His415 (provided by the active-site helix and the following "descending" chain comprising the conserved zinc binding consensus motif HEXXHXXGXXH) (SEQ ID NO: 3), and by the carbonyl and the hydroxyl oxygen of the hydroxamic acid moiety of the inhibiter (see FIGS. 1, 2a and 4). This zinc-imidazole ensemble is based on the distal ε-methyl-sulphur moiety of the strictly conserved Met435, harbored in the Met-turn characteristic for the metzincin clan (Bode et al., "Astacins, serralysins, snake venom and matrix metalloproteinases exhibit identical zinc binding environments (HEXXHXXGXXH (SEQ ID NO: 3) and Met-turn) and topologies and should be grouped into a common family, the 'metzincins'" *FEBS Lett.* 331, 134–140 (1993); Stöcker et al., "The metzincins: Topological and sequential relations between the astacins, adamalysins, serralysins, and matrix-ins (collagenases) define a superfamily of zinc-peptidases" *Protein Sci.* 4, 823–840 (1995)). Both carboxylate oxygens of the "catalytic" Glu406 (which acts as a general base during catalysis (Grams et al., "X-ray structures of human neutrophil collagenase complexed with peptide hydroxamate and peptide thiol inhibitors: Implications for substrate binding and rational drug design" *Eur. J. Biochem.* 228,. 830–841 (1995)) squeezed between the zinc-liganding imidazole of His405 and the edge strand, are hydrogen bonded to the hydroxyl and the N—H group of the hydroxamic acid (see FIG. 4). To the right of the catalytic zinc opens the deep S1' pocket, which, besides the S1' wall-forming segment (bottom, FIGS. 1 and 2a), is bordered by the side chains of His405 and Glu406 (left), the sIV main chain and the Leu345 side chain (top), and the side chains of Val440 (back) and Ala439 (right). To the right of Ala439 opens a second (S3') pocket, which inside the molecule merges with the S1' pocket, leaving a small bridge made of the opposing side chains of Ala439 and Leu348 (FIG. 2a).

The (pseudo)peptide part of the inhibitor binds in an extended geometry to the notched right-hand side of the active-site cleft, mimicking the interaction of the primed residues of a productively bound peptide substrate (FIG. 2a). It runs antiparallel to the upper short bulge Gly346-Thr347-Leu348 and parallel to the S1' wall-forming segment Pro437-Ile438-Ala439, making two and two inter-main chain hydrogen bonds, respectively. The dominant intermolecular interactions are made by the P1' isobutyl (pseudo-leucyl) side chain of the inhibitor and the essentially hydrophobic S1' pocket, however, is large and accommodates three partially ordered solvent molecules in addition. The P2' t-butyl side chain extends away from the enzyme, but nestles to the hydrophobic canopy above formed by the enzyme's bulge. The P3' Ala side chain points into the large negatively charged S3' pocket, but is too short to make favorable contacts. The C-terminal diaminoethyl group has different conformations in the four molecules.

The P1' to P3' segment Val77-Arg78-Ser79 of a bound pro-TNFα probably binds in a similar manner, possibly under better matching with the underlying cleft surface; the preceding P3 to P1 residues Ala74-Gln75-Ala76 certainly will align antiparallel to the edge strand, with their side chains extending into the (partially charged) S3 pocket and the (negatively charged) shallow S2 depression, and projecting out of the central cleft, respectively. The primed subsites and surrounding molecular surfaces of TACE are dominated by negative charges, while the non-primed subsites are essentially hydrophobic in nature (FIG. 2a). More distant interactions may be involved in the specificity of TACE for processing pro-TNFα. The 12 residue substrate comprising the pro-TNFα cleavage site can also be split by some of the MMPs, although with less specificity and efficacy (Black et al., "Relaxed specificity of matrix metalloproteinases (MMPs) and TIMP intensity of tumor necrosis factor-α (TNF-α) production suggest the major TNF-α converting enzyme is not an MMP" *Biochem. Biophys. Res. Commun.* 225, 400–405 (1996)). Thus, the preferential processing of the (probably trimeric) (Tang et al., "Human pro-tumor necrosis factor is a homotrimer" *Biochem.* 35, 8216–8225 (1996a); Tang et al., "Length of the linking domain of human pro-tumor necrosis factor determines the cleavage processing" *Biochem.* 35, 8226–8233 (1996b)) membrane-bound pro-TNFα in vivo might in part be due to correct assembling, i.e. suitable presentation of the pro-TNFα cleavage segment to the TACE active site in a distinct distance from the anchoring membrane. Some experimental evidence (Tang et al., *Biochem.* 35, 8216–8225 (1996a); Tang et al., *Biochem.* 35, 8226–8233 (1996b)) suggests that the cleavage site might not be determined by the cleavage sequence alone, but that also the distance to the base of the compact cone formed by the associated C-terminal segments of three TNFα molecules (Jones et al., "Structure of tumor necrosis factor" *Nature* 338, 225–228 (1989)) plays a role. In a productive TACE-proTNFα complex, the base of this TNFα-trimer cone (into which the disordered N-termini run up) may be recognized by the "right" side of the TACE catalytic domain (FIG. 2a), with the about 10 residues long spacer favoring the correct placement of the proTNFα Ala76-Val77 scissile peptide bond in the active site of TACE.

Figure 5:
FIG. 5.

The polypeptide topology and in particular the surface presentation of the catalytic zinc prove the catalytic domain of TACE to be a typical metzincin. (Bode et al., "Astacins, scrralysins, snake venom and matrix metalloproteinases exhibit identical zinc binding environments (HEXXHXXGXXH (SEQ ID NO: 3) and Met-turn) and topologies and should be grouped into a common family, the 'metzincins'" *FEBS lett.* 331, 134–140 (1993); Stöcker et al., "The metzincins: Topological and sequential relations between the astacins, adamalysins, serralysins, and matrixins (collagenases) define a superfamily of zinc-peptidases" *Protein Sci.* 4, 823–840 (1995)) A superposition with the other metzincins shows, however, that its topology is most similar to that of the catalytic domain of snake venom metalloproteinases such as adamalysin II (FIG. 5). (Gomis-Rüth et al., "First structure of a snake venom metalloproteinase: prototype for matrix metalloproteinases/collagenases" *EMBO J.* 12, 4151–4157 (1993); Zhang et al., "Structural interaction of natural and synthetic inhibitors with the venom metalloproteinase, atrolysin C (form d)" *Proc. Natl. Acad. Sci. USA* 91, 8447–8451 (1994); Kumasaka et al., "Crystal structure of H2-proteinase from the venom of *Trimeresurus flavoviridis*" *J. Biochem.* 119, 49–57 (1996)) This close homology is reflected by the much better simultaneous superposition of the central sheet and the large helices, but in particularly also by a couple of structural features, which TACE shares exclusively with the adamalysins such as: the long helix hB and the preceding multiple-turn loop arranged on top of the β-sheet; the typically arranged and shaped C-terminal helix hC; and the extended C-terminus placed on the backside surface. About 175 of the 263 TACE and 201 adamalysin α-atoms are topologically equivalent (with an rms deviation of 1.3 Å, 39 of which have identical side chains (FIG. 3). These numbers are close to those obtained from a comparison of members within the different metzincin families. (Stöcker et al., supra) In addition, detailed structural features prove the close relationship of TACE to the adamalysins: a more conserved core structure; the loosely arranged N-terminus; the characteristic Asp416 (directly following the zinc binding consensus motif, FIG. 3) involved in identical intramolecular hydrogen bond interactions; the adjacent disulfide bridge Cys423-Cys453 linking the first narrow loop to the C-terminal helix hD (which TACE does not share with adamalysin II, but with the H2-proteinase from the snake venom of *T. flavoviridis*) (Kumasaka et al., supra); disulfide bridge Cys365-Cys469 connecting the sIV-sV linker with the C-terminal helix hD; a similarly shaped active-site cleft, with particularly strong similarities in the S1' pocket and other primed subsites.

The catalytic domain of TACE (TCD) also differs from adamalysin II in several respects: with 263 residues, its chain is much longer; most of the additional residues of TACE are clustered giving rise to a more projecting hA-sII turn, to the two surface protuberances of the multiple-turn loop, to the two "ears" of the sIV-sV linker, and to a more bulged-out sV-hC connector (see FIGS. 3 and 5); lack of a calcium binding site but presence of a third disulfide bridge Cys225-Cys333 in TACE, both elements serving, however, for the same function namely to clamp the N-terminal chain to strand sIII; the quite deep S3' pocket of TACE which merges with its S1' pocket; an almost inverted charge pattern in and around the primed subsites, with an absolute predominance of positive charges in adamalysin.

According to its sequence, and probably with respect to its three-dimensional structure, the TACE catalytic domain is thus not a typical member of the mammalian ADAMs proper (a family of membrane-anchored cell-surface proteins, with the catalytic domain quite homologous to adamalysin (Wolfsberg et al., "ADAMs in Fertilization and Development" *Developm. Biol.* 180, 389–401 (1996))) TACE presumably shares this "outsider" role with (bovine) ADAM 10 (FIG. 3), which does also possess some TACE-like activity (Lunn et al., "Purification of ADAM 10 from bovine spleen as a TNFα convertase," *FEBS Lett.* 400, 333–335 (1997)), and whose Drosophila version (kuz) has recently been shown to process the Notch receptor (Rooke et al., *Science* 273, 1227–1231 (1996)). Also ADAM 10 probably exhibits an elongated hA-sII loop and the two "ears" typical for TACE, but might have a multiple-turn intermediate insize between TACE and adamalysin (see FIG. 3). Ninety of the ADAM 10 catalytic domain residues are identical to TACE further underlining the close homology (see FIG. 3), whereas the other mammalian ADAMs probably resemble much more adamalysin II (Gomis-Ruth et al., "Refined 2.0 Å crystal structure of snake venom zinc endopeptidase adamalysin II" *J. Mol. Biol.* 239, 513–544 (1994)).

Figure 2B:
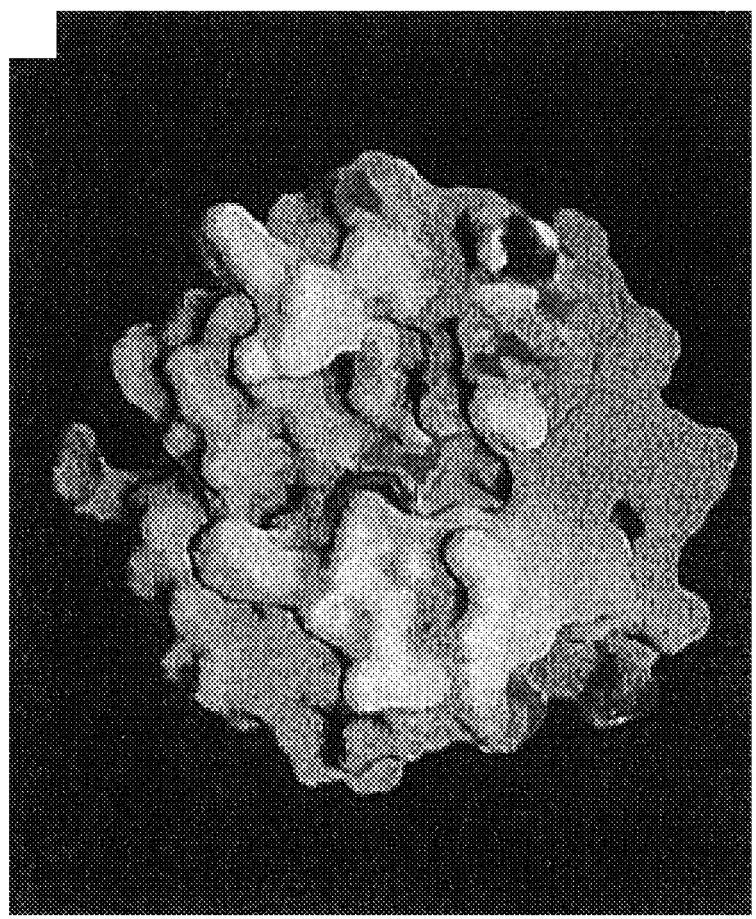

The structural homology of TACE to the MMPs is significantly lower. The relative arrangement of the common secondary structural elements differs more (reflected by the significantly larger mnis deviation of 1.6 Å of the about 120 topologically equivalent Cα-atoms), and the MMPs lack characteristic TACE/adamalysin structural elements (such as the intermediate helix hB and the multiple-turn loop, the Asp residue behind the third zinc-binding histidine), or exhibit typical determinants (such as the structural zinc and the integrated calcium ions) not seen in TACE. Notwithstanding the differences in secondary structure, the active-site cleft of TACE bears some similarity with that of the MMPs, with the flat nonprimed (left-hand) side, and the narrow primed side centering in the deep S1' pocket (FIG. 2b). This subsite similarity to the MMPs explains the observed partial sensitivity of TNFα-convertase activity towards synthetic hydroxamic acid inhibitors originally designed for inhibition of various MMPs (DiMartino et al., "Anti-arthritic activity of hydroxamic acid-based pseudopeptide inhibitors of matrix metalloproteinases and TNF-α processing" *Inflamm. Res.* 46, 211–215 (1997)). Model building experiments with TIMP-1 structure (Gomis-Rüth et al., "Mechanism of inhibition of the human matrix metalloproteinase stromelysin-1 by TIMP-1" *Nature* 389, 77–81(1997)) show no obvious obstacles in the active-site region of TACE that would easily explain its resistance to blockage by the TIMPs.

This TCD crystal structure thus gives evidence for a topological similarity of the catalytic domain of TACE with that of the adamalysins/ADAMs, and for a share of its substrate binding site to that of the MMPs. TACE exhibits, however, several structural peculiarities regarding surface contour, charge and shape, which facilitates the design of potent selective synthetic inhibitors.

In designing and developing compounds, such as inhibitors, mediators and other compounds having activities with biological significance, that associate with TACE, it is desirable to select compounds with a view toward the particular surface contour, charge, shape, and other physical characteristics of the TACE catalytic domain. Generally, the compounds should be capable of physically and structurally associating with TACE, as well as be able to assume a conformation that allows it to associate with TACE. The features described above will direct the skilled artisan in this regard. In particular, compounds with a linear functionality should be particularly suitable. Such compounds will be particularly suitable in light of the deep pockets of the TACE catalytic domain.

The compounds that associate with TACE, for example, may be designed to associate with the S1' region or the S1'S3' pocket of TACE. Compounds that associate with TACE also may be designed to (i) incorporate a moiety that chelates zinc. Further exemplary compounds include compounds are designed to form a hydrogen bond with Leu348 or Gly349 of TACE, (ii) introduce a non-polar group which occupies the S1' pocket of TACE, (iii) introduce a group which lies within the channel joining S1'-S3' pockets of TACE and which makes appropriate van der Waal contact with the channel, and (iv) form a hydrogen bond with Leu348 or Gly349 on the backbone amide groups of TNF-α-converting enzyme, or (v) any combination of the above.

Computer-Readable Medium

The present invention also relates to a computer-readable medium having recorded thereon the x-ray diffraction structure coordinates of a crystalline TACE polypeptide. The computer-readable media of the invention are useful for storage, transfer, and use with software of the TACE structural coordinates. The computer readable medium may be any suitable data storage material, including, but not limited to, a floppy disc, a hard disc, computer-type Random Access Memory, Read-Only Memory flash memory, CD-ROM, recordable and rewritable CDs, recordable and rewritable DVDs, magnetic-optical disk, ZIP drive, JAZ drive, Syquist drive, digital tape drive, or the like. Other suitable media will be known to those of skill in the art.

In one embodiment, the computer readable medium comprises the coordinates of Table 1 or a substantial portion thereof. The computer-readable medium may be used in conjunction with a machine programmed with instructions for using the data recorded on the medium, such as a computer loaded with one or more programs identified throughout the specification, to display a graphical, three-dimensional representation of a TACE polypeptide, or any part thereof.

Computer Based System

Figure 6:
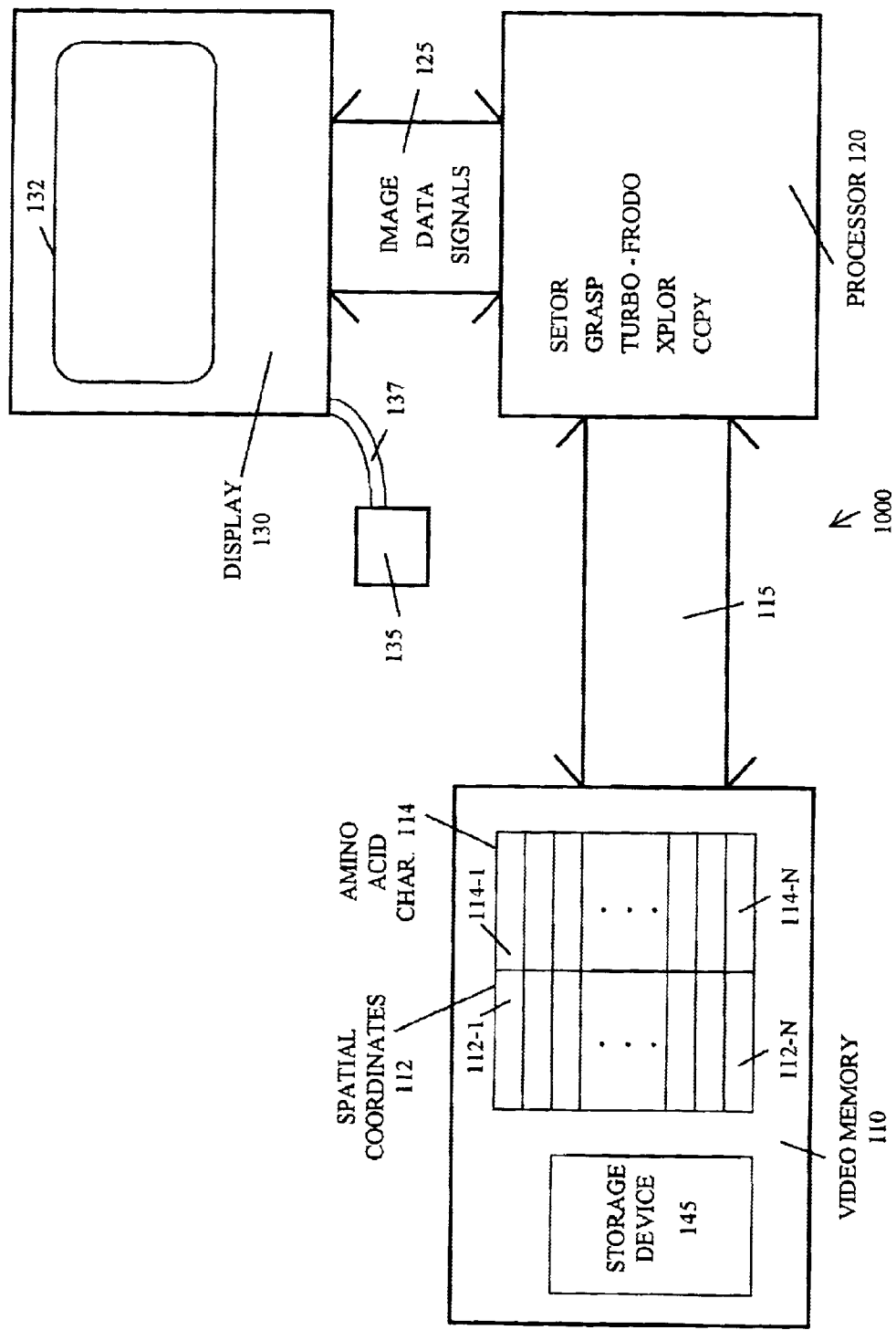
FIG. 6.

FIG. 6 illustrates a system 1000 for studying a TACE polypeptide. The system includes a video memory 110 that stores information representing at least a portion of a TACE polypeptide. The memory has at least one first-type storage region 112, having recorded thereon a set of spatial coordinates specifying a location in a three dimensional space, and at least one second-type storage region 114, having recording thereon information representing a characteristic of one of a plurality of amino acids. The second-type storage regions are logically associated with the first-type storage regions in the video memory 110 to represent a geometric arrangement of at least one characteristic of at least a portion of the TACE polypeptide in the three dimensional space. Memory, 112 and 114 can comprise, for example, the data shown in Table 1. The system 1000 also includes a processor, coupled to the memory to access the first-type storage regions 112 and the second-type storage regions 114, to generate image signals for depicting a visual three dimensional image of at least one characteristic of at least a portion of the TACE polypeptide in the three dimensional space based on data from the memory 110. The processor can be any general purpose processor with a CPU, register, memory and the like. A display 130 coupled to the processor 120 via lines 125 to receive the image signals, for depicting a visual three dimensional image of at least one characteristic of at least a portion of the TACE polypeptide in the three dimensional space based on the image data on a screen 132.

Figure 4:
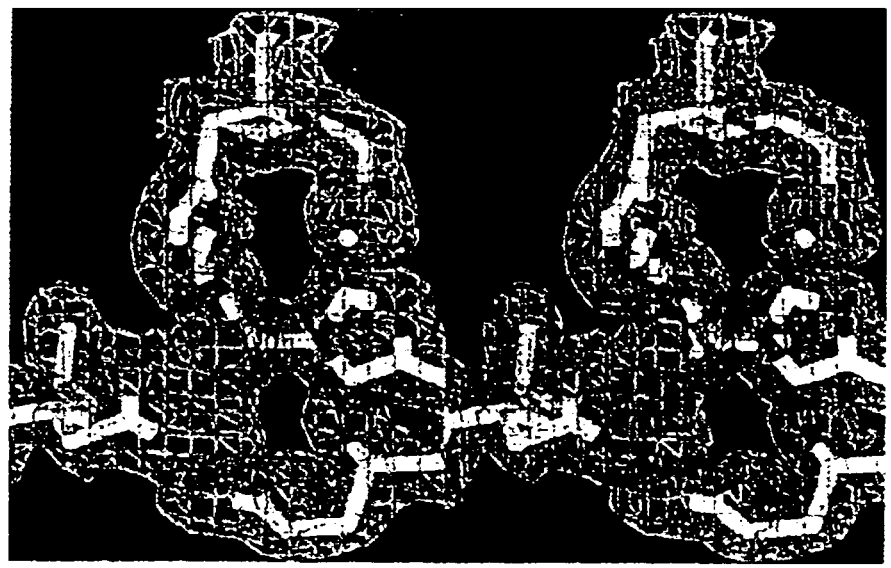
FIG. 4.

In one embodiment of the invention, the image data includes data for depicting a visual three dimensional image of a ribbon structure of at least a portion of a TACE polypeptide in three dimensional space, such as shown in FIG. 1. In another embodiment, the image data includes data for depicting a visual three dimensional image of a solid model representation of at least a portion of said TACE polypeptide in three dimensional space, such as shown in FIG. 2. In still another embodiment, the image data includes data for depicting a visual three dimensional image of electrostatic surface potential of at least a portion of TACE polypeptide in three dimensional space, such as shown in FIG. 2. In yet another embodiment, the image data includes data for depicting a visual three dimensional stereo image of at least a portion of a TACE polypeptide in three dimensional space, such as shown in FIG. 4.

The system 1000 of the present invention may further comprise a storage device 145 that stores data representing a geometric arrangement of a characteristic of a composition other than the TACE polypeptide and an operator interface, such as a mouse 135, for receiving instructions from a operator. Storage device 145 can include, for example, the three-dimensional X-ray coordinate data for other chemical entities. The processor 120 is coupled to the storage device 145 and to said operator interface 135 and generates additional image data for depicting the geometric arrangement of the characteristic of the composition relative to said visual three dimensional image of said at least one characteristic of said at least a portion of TACE polypeptide on the screen 132 based on instructions from the operator interface. In the FIG. 6 embodiment, the storage device 145 is part of the memory 110.

The first-type storage regions 112 and said second-type storage regions 114 are regions of, for example, a semiconductor memory, regions of an optical disk, or regions of a magnetic memory.

In one embodiment, processor 120 and video memory 110 are in the form of a UNIX or VAX computer, such those available from Silicon Graphics, Sun Microsystems, and IBM. However, the invention is not limited to use of this particular hardware and software.

The invention is described in more detail in the following illustrative examples. Although the examples may represent only selected embodiments of the invention, it should be understood that the following examples are illustrative and not limiting.

EXAMPLE 1

TACE Polypeptide Expression, Isolation, and Purification

A cDNA encoding the signal peptide, pro and catalytic domains of TACE, amino acid residues 1–477, as disclosed in Black et al., "A Metalloproteinase disintigrin that releases tumour-necrosis factor-α from cells," *Nature* 385: 729–733 (February 1997), with Ser266 changed to Ala, Asn452 changed to Gln and the sequence Gly-Ser-(His)$_6$ added to the C-terminus, was inserted into an expression vector for CHO cells. The TACE polypeptide was expressed in CHO cells and a mixture of the TACE polypeptide beginning either with Val212 or Arg215 was secreted. The cells were cultured in the drug, methotrexate, which kills those cells that did not incorporate the vector.

The expressed TACE polypeptide was then purified. Purification started with 5 liters of the medium containing the expressed TACE polypeptide. The medium was concentrated to about 200 mL with a Millipore 10K cut-off, 1 ft$^2$ TFF diafiltration unit. The pumping rate was 50–100 mL/min. Two liters of a buffer solution of 20 mM Tris (pH 7.5) and 300 mM NaCl (Buffer E) was then added to the sample.

The sample was reconcentrated as described above and diluted a second time with 2 liters of Buffer E, reconcentrated again, diluted a third time with 2 liters of Buffer E, and reconcentrated to about 100 mL. The sample retained in the diafiltration unit was recovered by a back-flush. This material was then filtered through a 0.45 μm and was azide added to 0.05%. The filtered sample was stored overnight at 4° C.

After overnight storage, imidazole was added to the filtered sample to 5 mM from a 200 mM stock in water and ZnCl$_2$ was added to 5 uM from a 1 M stock in water. The sample then was pumped over 2.2 mL of Quiagen Ni-NTA Superflow resin (Cat. # 30430) at 3 mL/min (column size 7.5×50 mm).

The column was washed at 5 mL/min with 100 mL of a buffer of 20 mM Tris pH 7.5, 300 mM NaCl, 5 mM imidazole, and 5 uM ZnCl$_2$ (Buffer A). The protein was then eluted with an increasing gradient of imidazole, going up to 200 mM in 1 minute (5 mL total volume), followed by 35 mL of 200 mM imidazole in Buffer A. Two mL fractions were collected, TACE generally coming off about 6 mL into the elution. The fractions were collected in tubes containing 500 ul of 50% glycerol in water and 200 ul of 1 M Tris pH 8. The glycerol in water was prepared the day of the column run.

A dot blot, with 3 μl from each fraction, was stained with amido black to determine which fractions contained a significant amount of protein. The fractions with a significant amount of protein were pooled. The pool was then concentrated to 1–2 mL with a 10 K cut-off Amicon Centriprep concentrator.

The inhibitor N-{D,L-2-(hydroxyaminocarbonyl)methyl-4-methylpentanoyl}-L-3-amino-2-dimethylbutanoyl-L-alanine, 2amino)ethyl amide was added to the concentrated sample to 1 mM from a 50 mM stock in water, and octylglucoside was added to 1% from a 10% stock in water. The sample was then incubated at room temperature for 15–24 hours.

Following incubation, the sample was applied to a 21.5× 600 mm size exclusion column, LKB 2135-365, packed with TSK-G3000 SWG, and equilibrated with 10 mM Tris pH 7.5, 100 mM NaCl, 10% glycerol. This buffer was then pumped through the column at 2.5 mL/min for 100 minutes. The TACE polypeptide in the effluent was detected by absorption at 280 nm. Excluded material generally eluted at about 38 minutes. The pure TACE generally eluted at about 78 minutes or longer.

A gel analysis, with 15 μl of all fractions with significant protein was then carried out to determine which fractions should be pooled. The size-exclusion chromatography pool was concentrated to about 1 mL with a 10 K cut-off Amicon Centriprep concentrator.

The inhibitor N-{D,L-2-(hydroxyaminocarbonyl)methyl-4-methylpentanoyl}-L-3-amino-2-dimethylbutanoyl-L-alanine, 2-(amino)ethyl amide was then added to the purified sample to a concentration of 1 mM. The protein can be stored at 4° C.

EXAMPLE 2

Protein Crystallization

A DNA construct comprising the prodomain and the catalytic domain of human TACE (resides 1–477) was fused to the sequence Gly-Ser-(His)$_6$ (SEQ ID NO: 2) to facilitate purification of the protein on a Ni-NTA affinity column. Chinese Hamster Ovary (CHO) were cells used for protein expression. The cells secreted a mixture of mature TACE beginning with either Val212 or Arg215. TACE-containing fractions from the Ni-NTA column were incubated in a buffer containing octylglucoside and the binding partner N-[D,L-[2-(hydroxyaminocarnbonyl)methyl]-4-methyl-pentanoyl)-L-3-(tert-butyl)-glycyl-L-alanine. The final purification step was performed on a gel filtration column. Purified TACE was stored in a buffer containing 10 mM Tris/HCL, pH 7.5, 100 mM NaCl, 10% glycerol and 1 mM of inhibitor (TACE buffer).

Crystallization experiments were set up at a TACE concentration of approximately 5 mg/mL by mixing TACE (in TACE buffer) in a 1:1 ratio with the crystallization buffers listed below and using the sitting drop vapor diffusion technique. The experiments were performed in duplicate and incubated either at about 4° C. or at 20° C. Crystalline precipitate was obtained at 20° C. in the following crystallization buffers:

Buffer A) 0.1 M Na Acetate pH 5.3, 0.2 M CaCl$_2$, 30% v/v Ethanol

Buffer B) 0.1 M Na Citrate pH 5.0, 40% v/v Ethanol

Buffer C) 0.1 M Na Citrate pH 8.7, 20% w/v PEG 4000, 20% v/v Isopropanol

Small crystals were obtained upon transferring seeds from the crystalline precipitate with a hair of a rabbit into a 1:1 mixture of a concentrated sample of TACE (12 mg/mL in TACE buffer) with either buffer B or C. Further refinement of buffer C resulted in buffer D, which allowed the production of crystals suitable for X-ray data collection.

Buffer D) 0.1 M Na Citrate pH 5.4, 20% w/v PEG 4000, 20% v/v Isopropanol

The first data set was measured to a reduction of 2.5 Å on a MAR300 imaging plate scanner attached to a Rigaku-Denki totaling Cu-anode generator operated at 5.4 kW providing graphite-monochromatized CuKα radiation. The data were processed with MOSFLM v. 5.23 program and routines of the CCP4 suite. All attempts to solve the structure by molecular replacement methods using either adamalysin II, an all-alanine model of adamalysin II and models generated failed to produce useful starting points for phasing. Thus the locations of four independent zinc atoms were determined with the help of an anomalous difference Patterson synthesis. In order to measure MAD data, the crystals were deep-frozen in liquid nitrogen. Therefore, crystals were transferred into a cryo buffer (80% v/v buffer D containing 17% v/v glycerol) with the help of a silk loop of appropriate size, soaked for about 10 seconds and then immediately deep-frozen at 90 degrees K.

The crystals obtained belong to the monoclinic space group $P2_1$, have cell constants a=61.38 Å (angstrom), b=126.27 Å, c=81.27 Å, β=107.41°, and contain four molecules in the asymmetric unit.

EXAMPLE 3
X-ray Diffraction

Using the crystals described in Example 2, a first data set was measured to a resolution of 2.5 Å on a MAR300 imaging plate scanner attached to a Rigaku-Denki. rotating Cu-anode generator operated at 5.4 kW providing graphite-monochromatized CuKα radiation. The data were processed at with the MOSFLM v. 5.23 program and routines of the CCP4 suite.

All attempts to solve the structure by molecular replacement methods using either adamalysin II, an all-alanine model of adamalysin II, and other models failed to produce useful starting points for phasing.

Thus, the locations of the four independent zinc atoms were determined with the help of an anomalous difference Patterson synthesis. In order to measure MAD data, the crystals were deep-frozen in a nitrogen gas stream cooled down to the temperature of liquid nitrogen. The crystals were first transferred into a cryo-buffer of 80% v/v Buffer D (0.1 M Na Citrate pH 5.4, 20% w/v PEG 4000, 20% v/v Isopropanol) containing 17% v/v glycerol. Transfer to the cryo-buffer was performed with the help of a silk loop of appropriate size. The crystals were soaked in the cryo-buffer for about 10 seconds and then immediately deep-frozen at 90 K.

Anomalous diffraction data to 2.0 Å were collected with MAR345 imaging plate scanner at 90 K on the BW6 wiggler beamline of DORIS (DESY, Hamburg, Germany), using monochromatic X-ray radiation at the wavelengths of maximal f" (1.2769 Å) and minimal f" (1.2776 Å) at the K absorption edge of zinc and at a remote wavelength (1.060 Å). The data were scanned and evaluated using DENZO/SCALEPACK, yielding 77653 independent reflections from 1051836 measurements (96.9% completeness, R-merge 0.031 in intensities).

MAD phases were refined and calculated with MLPHARE including all measured data to 2.0 Å resolution. Their initial mean-figure-of-merit of 0.53 was increased to 0.76 by solvent flattening/histogram matching methods applying DM. This density allowed building of the complete chains of the four independent TACE catalytic domains and the bound hydroxamic acid substrates on an SGI system using TURBO-FRODO. This model was crystallographically refined with XPLOR and with CCP4 routines to a crystallographic R factor of 18.6% ($R_{free}$ 27.4%) using 79400 independent reflections from, 12.0 to 2 A. resolution.

Four independent TACE molecules form the periodic arrangement.

Molecules 1 and 2, and 3 and 4 are defined from Asp219 and Met221, respectively, to Ser474.

EXAMPLE 4
X-ray Diffraction

Anomalous dispersion diffraction data to 2.0 Å were collected with a MAR345 imaging plate scanner at 100 K on the wiggler beamline of DORIS (DESY, Hamburg, Germany), using monochromatic X-ray radiation of maximal f' (1.2797 Å) and minimal f' (1.2804 Å) at the K absorption edge of zinc and at a remote wavelength (1.060 Å). These data were evaluated and scanned using DENZO/SCALEPACK, yielding 77,653 independent reflections (96.9% completeness, R-merge 0.031).

The structure coordinates obtained are reproduced in Table 1.

TABLE 1

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 1 N | ASP | A | 219 | 0.865 | 33.077 | 15.204 | 1.00 | 20.00 |
| ATOM | 2 OD2 | ASP | A | 219 | 5.154 | 33.868 | 14.335 | 1.00 | 20.00 |
| ATOM | 3 OD1 | ASP | A | 219 | 4.450 | 35.924 | 14.844 | 1.00 | 20.00 |
| ATOM | 4 CG | ASP | A | 219 | 4.191 | 34.718 | 14.461 | 1.00 | 20.00 |
| ATOM | 5 CB | ASP | A | 219 | 2.738 | 34.303 | 14.156 | 1.00 | 20.00 |
| ATOM | 6 CA | ASP | A | 219 | 2.290 | 33.026 | 14.883 | 1.00 | 20.00 |
| ATOM | 7 C | ASP | A | 219 | 3.166 | 32.889 | 16.123 | 1.00 | 20.00 |
| ATOM | 8 O | ASP | A | 219 | 3.439 | 33.884 | 16.819 | 1.00 | 20.00 |
| ATOM | 9 N | PRO | A | 220 | 3.629 | 31.679 | 16.386 | 1.00 | 20.00 |
| ATOM | 10 CG | PRO | A | 220 | 4.073 | 29.436 | 16.118 | 1.00 | 20.00 |
| ATOM | 11 CD | PRO | A | 220 | 3.224 | 30.531 | 15.588 | 1.00 | 20.00 |
| ATOM | 12 CB | PRO | A | 220 | 4.893 | 29.974 | 17.303 | 1.00 | 20.00 |
| ATOM | 13 CA | PRO | A | 220 | 4.523 | 31.452 | 17.495 | 1.00 | 20.00 |
| ATOM | 14 C | PRO | A | 220 | 5.649 | 32.530 | 17.443 | 1.00 | 20.00 |
| ATOM | 15 O | PRO | A | 220 | 6.513 | 32.741 | 18.173 | 1.00 | 20.00 |

TABLE 1-continued

REMARK Created by MOLEMAN V. 961218/7.2.5 at Fri Sep 19 20:05:05 1997 for user carlos
REMARK Moleman FDS file
CRYST1 61.387   126.278   81.273   90.00   107.42 90.00   P 21   4
CRIGX1         1.000000            0.000000            0.000000            0.00000
CRIGX2         0.000000            1.000000            0.000000            0.00000
CRIGX3         0.000000            0.000000            1.000000            0.00000
SCALE1         0.016290            0.000000            0.005111            0.00000
SCALE2         0.000000            0.007919            0.000000            0.00000
SCALE3         0.000000            0.000000            0.012896            0.00000

| | Atom Type | Residue | ! | # | X | Y | Z | OCC | B |
|---|---|---|---|---|---|---|---|---|---|
| ATOM | 16 N | MET | A | 221 | 5.766 | 33.341 | 16.625 | 1.00 | 48.83 |
| ATOM | 17 CE | MET | A | 221 | 9.090 | 36.336 | 12.584 | 1.00 | 53.01 |
| ATOM | 18 SD | MET | A | 221 | 9.248 | 36.147 | 14.337 | 1.00 | 54.21 |
| ATOM | 19 CG | MET | A | 221 | 8.515 | 34.606 | 14.801 | 1.00 | 51.15 |
| ATOM | 20 CB | MET | A | 221 | 7.101 | 34.778 | 15.298 | 1.00 | 48.69 |
| ATOM | 21 CA | MET | A | 221 | 6.875 | 34.306 | 16.701 | 1.00 | 48.22 |
| ATOM | 22 C | MET | A | 221 | 6.485 | 35.500 | 17.614 | 1.00 | 42.51 |
| ATOM | 23 O | MET | A | 221 | 7.279 | 36.002 | 18.427 | 1.00 | 43.93 |
| ATOM | 24 N | LYS | A | 222 | 5.215 | 35.817 | 17.508 | 1.00 | 36.53 |
| ATOM | 25 NZ | LYS | A | 222 | 1.844 | 39.934 | 13.657 | 1.00 | 40.05 |
| ATOM | 26 CE | LYS | A | 222 | 2.513 | 39.901 | 14.974 | 1.00 | 39.09 |
| ATOM | 27 CD | LYS | A | 222 | 2.353 | 38.522 | 15.613 | 1.00 | 38.20 |
| ATOM | 28 CG | LYS | A | 222 | 3.646 | 38.146 | 16.312 | 1.00 | 36.27 |
| ATOM | 29 CB | LYS | A | 222 | 3.345 | 37.404 | 17.597 | 1.00 | 33.97 |
| ATOM | 30 CA | LYS | A | 222 | 4.567 | 36.853 | 18.299 | 1.00 | 32.39 |
| ATOM | 31 C | LYS | A | 222 | 4.144 | 36.220 | 19.633 | 1.00 | 29.13 |
| ATOM | 32 O | LYS | A | 222 | 2.999 | 35.844 | 19.866 | 1.00 | 26.54 |
| ATOM | 33 N | ASN | A | 223 | 5.157 | 36.011 | 20.462 | 1.00 | 23.62 |
| ATOM | 34 CA | ASN | A | 223 | 4.951 | 35.296 | 21.704 | 1.00 | 22.97 |
| ATOM | 35 CB | ASN | A | 223 | 5.756 | 33.987 | 21.611 | 1.00 | 25.44 |
| ATOM | 36 CG | ASN | A | 223 | 7.229 | 34.245 | 21.372 | 1.00 | 26.32 |
| ATOM | 37 OD1 | ASN | A | 223 | 7.973 | 33.261 | 21.243 | 1.00 | 29.74 |
| ATOM | 38 ND2 | ASN | A | 223 | 7.688 | 35.482 | 21.319 | 1.00 | 25.96 |
| ATOM | 39 C | ASN | A | 223 | 5.327 | 36.123 | 22.908 | 1.00 | 18.46 |
| ATOM | 40 O | ASN | A | 223 | 5.365 | 35.556 | 23.983 | 1.00 | 18.08 |
| ATOM | 41 N | THR | A | 224 | 5.611 | 37.408 | 22.709 | 1.00 | 17.03 |
| ATOM | 42 CA | THR | A | 224 | 6.035 | 38.246 | 23.824 | 1.00 | 16.24 |
| ATOM | 43 CS | THR | A | 224 | 7.507 | 38.721 | 23.599 | 1.00 | 17.52 |
| ATOM | 44 OG1 | THR | A | 224 | 8.317 | 37.590 | 23.318 | 1.00 | 16.14 |
| ATOM | 45 CG2 | THR | A | 224 | 8.002 | 39.440 | 24.849 | 1.00 | 17.72 |
| ATOM | 46 C | THR | A | 224 | 5.152 | 39.464 | 24.033 | 1.00 | 16.13 |
| ATOM | 47 C | THR | A | 224 | 4.863 | 40.275 | 23.152 | 1.00 | 15.14 |
| ATOM | 48 N | CYS | A | 225 | 4.708 | 39.650 | 25.253 | 1.00 | 16.61 |
| ATOM | 49 CA | CYS | A | 225 | 3.915 | 40.833 | 25.646 | 1.00 | 17.81 |
| ATOM | 50 CB | CYS | A | 225 | 2.895 | 40.460 | 26.723 | 1.00 | 18.01 |
| ATOM | 51 SG | CYS | A | 225 | 2.120 | 41.843 | 27.562 | 1.00 | 18.77 |
| ATOM | 52 C | CYS | A | 225 | 4.899 | 41.914 | 26.101 | 1.00 | 17.46 |
| ATOM | 53 O | CYS | A | 225 | 5.614 | 41.703 | 27.033 | 1.00 | 18.52 |
| ATOM | 54 N | LYS | A | 226 | 5.070 | 42.945 | 25.285 | 1.00 | 17.94 |
| ATOM | 55 CA | LYS | A | 226 | 6.011 | 44.033 | 25.573 | 1.00 | 18.62 |
| ATOM | 56 CB | LYS | A | 226 | 6.373 | 44.816 | 24.311 | 1.00 | 21.04 |
| ATOM | 57 CG | LYS | A | 226 | 6.985 | 43.974 | 23.202 | 1.00 | 22.16 |
| ATOM | 58 CD | LYS | A | 226 | 8.395 | 43.451 | 23.514 | 1.00 | 24.95 |
| ATOM | 59 CE | LYS | A | 226 | 8.867 | 42.585 | 23.365 | 1.00 | 28.75 |
| ATOM | 60 NZ | LYS | A | 226 | 10.336 | 42.445 | 22.185 | 1.00 | 31.31 |
| ATOM | 61 C | LYS | A | 226 | 5.461 | 44.940 | 26.658 | 1.00 | 17.48 |
| ATOM | 62 O | LYS | A | 226 | 4.295 | 45.336 | 26.642 | 1.00 | 16.96 |
| ATOM | 63 N | LEU | A | 227 | 6.281 | 45.274 | 27.641 | 1.00 | 15.78 |
| ATOM | 64 CA | LEU | A | 227 | 5.848 | 46.025 | 28.777 | 1.00 | 15.23 |
| ATOM | 65 CB | LEU | A | 227 | 6.182 | 45.347 | 30.117 | 1.00 | 15.96 |
| ATOM | 66 CG | LEU | A | 227 | 5.848 | 43.884 | 30.334 | 1.00 | 15.88 |
| ATOM | 67 CD1 | LEU | A | 227 | 6.375 | 43.382 | 31.692 | 1.00 | 15.72 |
| ATOM | 68 CD2 | LEU | A | 227 | 4.356 | 43.646 | 30.314 | 1.00 | 13.61 |
| ATOM | 69 C | LEU | A | 227 | 6.462 | 47.398 | 28.965 | 1.00 | 16.89 |
| ATOM | 70 O | LEU | A | 227 | 7.639 | 47.635 | 28.725 | 1.00 | 17.35 |
| ATOM | 71 N | LEU | A | 228 | 5.585 | 48.248 | 29.488 | 1.00 | 16.01 |
| ATOM | 72 CA | LEU | A | 228 | 6.024 | 49.559 | 29.935 | 1.00 | 15.78 |
| ATOM | 73 CB | LEU | A | 228 | 5.105 | 50.721 | 29.644 | 1.00 | 15.98 |
| ATOM | 74 CG | LEU | A | 228 | 5.360 | 52.012 | 30.426 | 1.00 | 17.60 |
| ATOM | 75 CD1 | LEU | A | 228 | 6.596 | 52.712 | 29.853 | 1.00 | 15.81 |
| ATOM | 76 CD2 | LEU | A | 228 | 4.154 | 52.945 | 30.340 | 1.00 | 19.40 |
| ATOM | 77 C | LEU | A | 228 | 6.144 | 49.360 | 31.455 | 1.00 | 16.70 |
| ATOM | 78 O | LEU | A | 228 | 5.124 | 49.074 | 32.104 | 1.00 | 16.99 |
| ATOM | 79 N | VAL | A | 229 | 7.356 | 49.488 | 33.983 | 1.00 | 13.83 |
| ATOM | 80 CA | VAL | A | 229 | 7.484 | 49.343 | 33.450 | 1.00 | 12.75 |
| ATOM | 81 CB | VAL | A | 229 | 8.600 | 48.320 | 33.747 | 1.00 | 15.41 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | | 0.000000 | | 0.00000 |
| CRIGX2 | | 0.000000 | | 1.000000 | | | 0.000000 | | 0.00000 |
| CRIGX3 | | 0.000000 | | 0.000000 | | | 1.000000 | | 0.00000 |
| SCALE1 | | 0.016290 | | 0.000000 | | | 0.005111 | | 0.00000 |
| SCALE2 | | 0.000000 | | 0.007919 | | | 0.000000 | | 0.00000 |
| SCALE3 | | 0.000000 | | 0.000000 | | | 0.012896 | | 0.00000 |

| | Atom Type | Residue | ! | # | X | Y | Z | OCC | B |
|---|---|---|---|---|---|---|---|---|---|
| ATOM | 82 CG1 | VAL | A | 229 | 9.015 | 48.421 | 35.199 | 1.00 | 15.21 |
| ATOM | 83 CG2 | VAL | A | 229 | 8.062 | 46.910 | 33.451 | 1.00 | 16.11 |
| ATOM | 84 C | VAL | A | 229 | 7.758 | 50.710 | 34.055 | 1.00 | 11.45 |
| ATOM | 85 O | VAL | A | 229 | 8.592 | 51.462 | 33.529 | 1.00 | 10.78 |
| ATOM | 86 N | VAL | A | 230 | 7.029 | 51.092 | 35.090 | 1.00 | 11.10 |
| ATOM | 87 CA | VAL | A | 230 | 7.169 | 52.397 | 35.688 | 1.00 | 13.35 |
| ATOM | 88 CB | VAL | A | 230 | 5.910 | 53.299 | 35.516 | 1.00 | 13.78 |
| ATOM | 89 CG1 | VAL | A | 230 | 6.096 | 54.643 | 36.192 | 1.00 | 13.70 |
| ATOM | 90 CG2 | VAL | A | 230 | 5.577 | 53.586 | 34.050 | 1.00 | 12.14 |
| ATOM | 91 C | VAL | A | 230 | 7.495 | 52.252 | 37.154 | 1.00 | 12.98 |
| ATOM | 92 O | VAL | A | 230 | 6.791 | 51.546 | 37.877 | 1.00 | 14.51 |
| ATOM | 93 N | ALA | A | 231 | 8.582 | 52.891 | 37.570 | 1.00 | 14.57 |
| ATOM | 94 CA | ALA | A | 231 | 8.915 | 52.901 | 39.001 | 1.00 | 12.63 |
| ATOM | 95 CB | ALA | A | 231 | 10.382 | 52.556 | 39.219 | 1.00 | 14.54 |
| ATOM | 96 C | ALA | A | 231 | 8.616 | 54.305 | 39.505 | 1.00 | 13.54 |
| ATOM | 97 O | ALA | A | 231 | 9.215 | 55.290 | 39.004 | 1.00 | 12.89 |
| ATOM | 98 N | ASP | A | 232 | 7.739 | 54.412 | 40.500 | 1.00 | 13.89 |
| ATOM | 99 CA | ASP | A | 232 | 7.440 | 55.781 | 40.947 | 1.00 | 15.63 |
| ATOM | 100 CB | ASP | A | 232 | 6.061 | 55.875 | 41.560 | 1.00 | 16.03 |
| ATOM | 101 CG | ASP | A | 232 | 5.856 | 55.198 | 42.876 | 1.00 | 17.24 |
| ATOM | 102 OD1 | ASP | A | 232 | 4.725 | 55.249 | 43.432 | 1.00 | 18.20 |
| ATOM | 103 CD2 | ASP | A | 232 | 6.804 | 54.565 | 43.403 | 1.00 | 15.69 |
| ATOM | 104 C | ASP | A | 232 | 8.559 | 56.276 | 41.875 | 1.00 | 15.96 |
| ATOM | 105 O | ASP | A | 232 | 9.395 | 55.459 | 42.253 | 1.00 | 13.21 |
| ATOM | 106 N | HIS | A | 233 | 8.375 | 57.492 | 42.392 | 1.00 | 16.98 |
| ATOM | 107 CA | HIS | A | 233 | 9.399 | 58.118 | 43.244 | 1.00 | 16.61 |
| ATOM | 108 CB | HIS | A | 233 | 9.075 | 59.600 | 43.522 | 1.00 | 17.60 |
| ATOM | 109 CG | HIS | A | 233 | 7.977 | 59.866 | 44.494 | 1.00 | 17.74 |
| ATOM | 110 CD2 | HIS | A | 233 | 8.012 | 60.040 | 45.836 | 1.00 | 18.92 |
| ATOM | 111 ND1 | HIS | A | 233 | 6.648 | 59.946 | 44.152 | 1.00 | 17.72 |
| ATOM | 112 CE1 | HIS | A | 233 | 5.910 | 60.144 | 45.222 | 1.00 | 18.19 |
| ATOM | 113 NE2 | HIS | A | 233 | 6.730 | 60.214 | 46.266 | 1.00 | 19.56 |
| ATOM | 114 C | HIS | A | 233 | 9.562 | 57.364 | 44.535 | 1.00 | 16.98 |
| ATOM | 115 O | HIS | A | 233 | 10.626 | 57.385 | 45.170 | 1.00 | 14.73 |
| ATOM | 116 N | ARG | A | 234 | 8.457 | 56.762 | 45.005 | 1.00 | 16.26 |
| ATOM | 117 CA | ARG | A | 234 | 8.476 | 55.997 | 46.231 | 1.00 | 16.71 |
| ATOM | 118 CB | ARG | A | 234 | 7.083 | 55.600 | 46.688 | 1.00 | 19.19 |
| ATOM | 119 CG | ARG | A | 234 | 6.078 | 56.729 | 46.814 | 1.00 | 18.94 |
| ATOM | 120 CD | ARG | A | 234 | 4.726 | 56.181 | 47.250 | 1.00 | 21.89 |
| ATOM | 121 NE | ARG | A | 234 | 3.696 | 57.214 | 47.125 | 1.00 | 23.72 |
| ATOM | 122 CZ | ARG | A | 234 | 2.872 | 57.469 | 48.130 | 1.00 | 26.70 |
| ATOM | 123 NH1 | ARG | A | 234 | 2.923 | 56.798 | 49.270 | 1.00 | 27.34 |
| ATOM | 124 NH2 | ARG | A | 234 | 1.953 | 58.411 | 47.989 | 1.00 | 28.96 |
| ATOM | 125 C | ARG | A | 234 | 9.319 | 54.728 | 46.062 | 1.00 | 17.39 |
| ATOM | 126 O | ARG | A | 234 | 10.072 | 54.359 | 46.955 | 1.00 | 17.02 |
| ATOM | 127 N | PHE | A | 235 | 9.149 | 54.039 | 44.954 | 1.00 | 15.45 |
| ATOM | 128 CA | PHE | A | 235 | 9.913 | 52.829 | 44.669 | 1.00 | 17.15 |
| ATOM | 129 CB | PHE | A | 235 | 9.458 | 52.167 | 43.370 | 1.00 | 15.92 |
| ATOM | 130 CG | PHE | A | 235 | 10.063 | 50.804 | 43.165 | 1.00 | 14.51 |
| ATOM | 131 CD1 | PHE | A | 235 | 11.226 | 50.638 | 42.442 | 1.00 | 14.09 |
| ATOM | 132 CD2 | PHE | A | 235 | 9.429 | 49.693 | 43.697 | 1.00 | 13.27 |
| ATOM | 133 CE1 | PHE | A | 235 | 11.786 | 49.334 | 42.283 | 1.00 | 12.49 |
| ATOM | 134 CE2 | PHE | A | 235 | 9.979 | 48.436 | 43.514 | 1.00 | 14.15 |
| ATOM | 135 CZ | PHE | A | 235 | 11.159 | 48.280 | 42.812 | 1.00 | 11.73 |
| ATOM | 136 C | PHE | A | 235 | 11.391 | 53.211 | 44.502 | 1.00 | 15.85 |
| ATOM | 137 O | PHE | A | 235 | 12.309 | 52.611 | 45.041 | 1.00 | 15.02 |
| ATOM | 138 N | TYR | A | 236 | 16.573 | 54.282 | 43.750 | 1.00 | 15.65 |
| ATOM | 139 CA | TYR | A | 236 | 12.920 | 54.781 | 43.501 | 1.00 | 18.77 |
| ATOM | 140 CB | TYR | A | 236 | 12.809 | 56.087 | 42.744 | 1.00 | 20.15 |
| ATOM | 141 CG | TYR | A | 236 | 14.079 | 56.831 | 42.453 | 1.00 | 20.77 |
| ATOM | 142 CD1 | TYR | A | 236 | 15.006 | 56.379 | 41.554 | 1.00 | 23.25 |
| ATOM | 143 CE1 | TYR | A | 236 | 16.171 | 57.111 | 41.294 | 1.00 | 25.10 |
| ATOM | 144 CD2 | TYR | A | 236 | 14.303 | 58.043 | 43.094 | 1.00 | 22.97 |
| ATOM | 145 CE2 | TYR | A | 236 | 15.434 | 58.789 | 42.840 | 1.00 | 23.38 |
| ATOM | 146 CZ | TYR | A | 236 | 16.355 | 58.309 | 41.944 | 1.00 | 24.28 |
| ATOM | 147 OH | TYR | A | 236 | 17.490 | 59.032 | 41.699 | 1.00 | 27.10 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | | Atom Type | Residue | ! | # | X | Y | Z | OCC | B |
|---|---|---|---|---|---|---|---|---|---|---|
| ATOM | 148 | C | TYR | A | 236 | 13.668 | 55.005 | 44.807 | 1.00 | 18.41 |
| ATOM | 149 | O | TYR | A | 236 | 14.785 | 54.538 | 44.979 | 1.00 | 17.82 |
| ATOM | 150 | N | ARG | A | 237 | 13.029 | 55.671 | 45.741 | 1.00 | 18.84 |
| ATOM | 151 | NH2 | ARG | A | 237 | 16.164 | 60.578 | 45.801 | 1.00 | 36.66 |
| ATOM | 152 | NH1 | ARG | A | 237 | 15.513 | 58.642 | 46.822 | 1.00 | 35.42 |
| ATOM | 153 | CZ | ARG | A | 237 | 15.208 | 59.704 | 46.106 | 1.00 | 35.99 |
| ATOM | 154 | NE | ARG | A | 237 | 13.940 | 59.862 | 45.712 | 1.00 | 36.11 |
| ATOM | 155 | CD | ARG | A | 237 | 12.867 | 58.910 | 45.981 | 1.00 | 32.12 |
| ATOM | 156 | CG | ARG | A | 237 | 12.655 | 58.442 | 47.386 | 1.00 | 28.99 |
| ATOM | 157 | CB | ARG | A | 237 | 12.578 | 56.978 | 47.698 | 1.00 | 22.94 |
| ATOM | 158 | CA | ARG | A | 237 | 13.566 | 56.021 | 47.029 | 1.00 | 21.89 |
| ATOM | 159 | C | ARG | A | 237 | 13.824 | 54.847 | 47.959 | 1.00 | 22.82 |
| ATOM | 160 | O | ARG | A | 237 | 14.874 | 54.759 | 48.586 | 1.00 | 22.33 |
| ATOM | 161 | N | TYR | A | 238 | 12.826 | 53.995 | 48.165 | 1.00 | 20.93 |
| ATOM | 162 | CA | TYR | A | 238 | 12.807 | 52.950 | 49.142 | 1.00 | 22.79 |
| ATOM | 163 | CB | TYR | A | 238 | 11.438 | 52.835 | 49.835 | 1.00 | 25.02 |
| ATOM | 164 | CG | TYR | A | 238 | 11.052 | 54.133 | 50.502 | 1.00 | 28.43 |
| ATOM | 165 | CD1 | TYR | A | 238 | 10.191 | 55.011 | 49.873 | 1.00 | 30.38 |
| ATOM | 166 | CE1 | TYR | A | 238 | 9.827 | 56.214 | 50.439 | 1.00 | 32.45 |
| ATOM | 167 | CD2 | TYR | A | 238 | 11.570 | 54.501 | 51.729 | 1.00 | 30.38 |
| ATOM | 168 | CE2 | TYR | A | 238 | 11.228 | 55.709 | 52.309 | 1.00 | 32.79 |
| ATOM | 169 | CZ | TYR | A | 238 | 10.384 | 56.572 | 51.647 | 1.00 | 33.85 |
| ATOM | 170 | OH | TYR | A | 238 | 10.043 | 57.784 | 52.208 | 1.00 | 34.86 |
| ATOM | 171 | C | TYR | A | 238 | 13.222 | 51.579 | 48.683 | 1.00 | 22.48 |
| ATOM | 172 | O | TYR | A | 238 | 13.682 | 50.772 | 49.509 | 1.00 | 24.69 |
| ATOM | 173 | N | MET | A | 239 | 13.171 | 51.306 | 47.405 | 1.00 | 20.92 |
| ATOM | 174 | CA | MET | A | 239 | 13.680 | 50.048 | 46.893 | 1.00 | 18.57 |
| ATOM | 175 | CB | MET | A | 239 | 12.667 | 49.374 | 45.965 | 1.00 | 18.57 |
| ATOM | 176 | CG | MET | A | 239 | 11.394 | 48.971 | 46.729 | 1.00 | 18.44 |
| ATOM | 177 | SD | MET | A | 239 | 13.677 | 47.664 | 47.929 | 1.00 | 17.64 |
| ATOM | 178 | CE | MET | A | 239 | 12.084 | 46.309 | 46.855 | 1.00 | 16.38 |
| ATOM | 179 | C | MET | A | 239 | 14.975 | 50.292 | 46.121 | 1.00 | 17.52 |
| ATOM | 180 | O | MET | A | 239 | 15.826 | 49.422 | 46.133 | 1.00 | 16.58 |
| ATOM | 181 | N | GLY | A | 240 | 15.067 | 51.440 | 45.447 | 1.00 | 16.74 |
| ATOM | 182 | CA | GLY | A | 240 | 16.198 | 51.733 | 44.602 | 1.00 | 16.82 |
| ATOM | 183 | C | GLY | A | 240 | 17.334 | 52.497 | 45.232 | 1.00 | 20.60 |
| ATOM | 184 | O | GLY | A | 240 | 18.280 | 52.875 | 44.516 | 1.00 | 20.21 |
| ATOM | 185 | N | ARG | A | 241 | 17.242 | 52.871 | 46.503 | 1.00 | 20.89 |
| ATOM | 186 | CA | ARG | A | 241 | 18.300 | 53.628 | 47.162 | 1.00 | 24.17 |
| ATOM | 187 | CB | ARG | A | 241 | 19.609 | 52.806 | 47.126 | 1.00 | 26.15 |
| ATOM | 188 | CG | ARG | A | 241 | 19.504 | 51.488 | 47.875 | 1.00 | 29.48 |
| ATOM | 189 | CD | ARG | A | 241 | 20.771 | 50.648 | 47.896 | 1.00 | 31.73 |
| ATOM | 190 | NE | ARG | A | 241 | 21.417 | 50.785 | 49.228 | 1.00 | 32.75 |
| ATOM | 191 | CZ | ARG | A | 241 | 22.188 | 51.837 | 49.428 | 1.00 | 33.64 |
| ATOM | 192 | NH1 | ARG | A | 241 | 22.361 | 52.722 | 48.450 | 1.00 | 35.35 |
| ATOM | 193 | NH2 | ARG | A | 241 | 22.752 | 52.014 | 50.598 | 1.00 | 32.64 |
| ATOM | 194 | C | ARG | A | 241 | 18.497 | 55.001 | 46.543 | 1.00 | 25.05 |
| ATOM | 195 | O | ARG | A | 241 | 19.574 | 55.585 | 46.696 | 1.00 | 21.63 |
| ATOM | 196 | N | GLY | A | 242 | 17.470 | 55.529 | 45.831 | 1.00 | 22.70 |
| ATOM | 197 | CA | GLY | A | 242 | 17.603 | 56.784 | 45.110 | 1.00 | 20.94 |
| ATOM | 198 | C | GLY | A | 242 | 18.622 | 56.667 | 44.003 | 1.00 | 20.36 |
| ATOM | 199 | O | GLY | A | 242 | 19.255 | 57.656 | 43.639 | 1.00 | 20.42 |
| ATOM | 200 | N | GLY | A | 243 | 18.841 | 55.486 | 43.445 | 1.00 | 19.57 |
| ATOM | 201 | CA | GLU | A | 243 | 19.832 | 55.277 | 42.418 | 1.00 | 19.51 |
| ATOM | 202 | CB | GLU | A | 243 | 20.951 | 54.324 | 42.832 | 1.00 | 21.04 |
| ATOM | 203 | CG | GLU | A | 243 | 21.992 | 54.818 | 43.816 | 1.00 | 22.54 |
| ATOM | 204 | CD | GLU | A | 243 | 22.782 | 53.747 | 44.543 | 1.00 | 24.67 |
| ATOM | 205 | OE1 | GLU | A | 243 | 23.740 | 54.097 | 45.292 | 1.00 | 24.23 |
| ATOM | 206 | OE2 | GLU | A | 243 | 22.512 | 52.535 | 44.451 | 1.00 | 22.83 |
| ATOM | 207 | C | GLU | A | 243 | 19.104 | 54.717 | 41.197 | 1.00 | 19.62 |
| ATOM | 208 | O | GLU | A | 243 | 18.414 | 53.698 | 41.291 | 1.00 | 18.85 |
| ATOM | 209 | N | GLU | A | 244 | 19.324 | 55.341 | 40.075 | 1.00 | 19.48 |
| ATOM | 210 | CA | GLU | A | 244 | 18.699 | 54.904 | 38.833 | 1.00 | 22.19 |
| ATOM | 211 | CB | GLU | A | 244 | 18.928 | 55.950 | 37.739 | 1.00 | 25.49 |
| ATOM | 212 | CG | GLU | A | 244 | 18.502 | 55.433 | 36.371 | 1.00 | 29.88 |
| ATOM | 213 | CD | GLU | A | 244 | 18.409 | 56.498 | 35.310 | 1.00 | 32.59 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | | Residue | ! | # | X | Y | Z | OCC | B |
|---|---|---|---|---|---|---|---|---|---|---|
| ATOM | 214 | OE1 | GLU | A | 244 | 18.205 | 57.691 | 35.608 | 1.00 | 33.16 |
| ATOM | 215 | OE2 | GLU | A | 244 | 18.528 | 56.090 | 34.136 | 1.00 | 35.02 |
| ATOM | 216 | C | GLU | A | 244 | 19.176 | 53.524 | 38.424 | 1.00 | 21.10 |
| ATOM | 217 | O | GLU | A | 244 | 18.360 | 52.654 | 38.029 | 1.00 | 17.68 |
| ATOM | 218 | N | SER | A | 245 | 20.466 | 53.247 | 38.644 | 1.00 | 18.06 |
| ATOM | 219 | CA | SER | A | 245 | 21.001 | 51.960 | 38.207 | 1.00 | 20.29 |
| ATOM | 220 | CB | SER | A | 245 | 22.549 | 51.953 | 38.270 | 1.00 | 21.06 |
| ATOM | 221 | OG | SER | A | 245 | 22.833 | 52.394 | 39.607 | 1.00 | 21.74 |
| ATOM | 222 | C | SER | A | 245 | 20.409 | 50.844 | 39.056 | 1.00 | 17.46 |
| ATOM | 223 | O | SER | A | 245 | 19.970 | 49.834 | 38.536 | 1.00 | 18.81 |
| ATOM | 224 | N | THR | A | 246 | 20.355 | 51.020 | 40.343 | 1.00 | 15.88 |
| ATOM | 225 | CA | THR | A | 246 | 19.821 | 50.027 | 41.275 | 1.00 | 18.13 |
| ATOM | 226 | CB | THR | A | 246 | 20.051 | 50.546 | 42.689 | 1.00 | 19.42 |
| ATOM | 227 | OG1 | THR | A | 246 | 21.459 | 50.877 | 42.861 | 1.00 | 21.14 |
| ATOM | 228 | CG2 | THR | A | 246 | 19.692 | 49.547 | 43.761 | 1.00 | 19.86 |
| ATOM | 229 | C | THR | A | 246 | 18.337 | 49.757 | 41.014 | 1.00 | 16.92 |
| ATOM | 230 | O | THR | A | 246 | 17.915 | 48.619 | 41.068 | 1.00 | 14.90 |
| ATOM | 231 | N | THR | A | 247 | 17.545 | 50.799 | 40.800 | 1.00 | 17.19 |
| ATOM | 232 | CA | THR | A | 247 | 16.108 | 50.689 | 40.560 | 1.00 | 16.84 |
| ATOM | 233 | CB | THR | A | 247 | 15.458 | 52.076 | 40.443 | 1.00 | 16.21 |
| ATOM | 234 | OG1 | THR | A | 247 | 15.860 | 52.839 | 41.581 | 1.00 | 14.61 |
| ATOM | 235 | CG2 | THR | A | 247 | 13.920 | 52.069 | 40.449 | 1.00 | 14.87 |
| ATOM | 236 | C | THR | A | 247 | 15.848 | 49.892 | 39.308 | 1.00 | 15.69 |
| ATOM | 237 | O | THR | A | 247 | 15.088 | 48.922 | 39.295 | 1.00 | 14.94 |
| ATOM | 238 | N | THR | A | 248 | 16.502 | 50.305 | 38.232 | 1.00 | 16.92 |
| ATOM | 239 | CA | THR | A | 248 | 16.382 | 49.685 | 36.926 | 1.00 | 16.92 |
| ATOM | 240 | CB | THR | A | 248 | 17.322 | 50.415 | 35.963 | 1.00 | 17.93 |
| ATOM | 241 | OG1 | THR | A | 248 | 16.875 | 51.787 | 35.915 | 1.00 | 18.06 |
| ATOM | 242 | CG2 | THR | A | 248 | 17.381 | 49.792 | 34.586 | 1.00 | 19.15 |
| ATOM | 243 | C | THR | A | 248 | 16.712 | 48.202 | 36.972 | 1.00 | 18.22 |
| ATOM | 244 | O | THR | A | 248 | 16.073 | 47.313 | 36.427 | 1.00 | 14.91 |
| ATOM | 245 | N | ASN | A | 249 | 17.857 | 47.907 | 37.593 | 1.00 | 17.46 |
| ATOM | 246 | CA | ASN | A | 249 | 18.342 | 46.545 | 37.700 | 1.00 | 17.81 |
| ATOM | 247 | CB | ASN | A | 249 | 19.723 | 46.472 | 38.349 | 1.00 | 19.11 |
| ATOM | 248 | CG | ASN | A | 249 | 20.854 | 47.016 | 37.499 | 1.00 | 22.53 |
| ATOM | 249 | OD1 | ASN | A | 249 | 20.753 | 47.173 | 36.283 | 1.00 | 22.82 |
| ATOM | 250 | ND2 | ASN | A | 249 | 21.989 | 47.306 | 33.157 | 1.00 | 21.73 |
| ATOM | 251 | C | ASN | A | 249 | 17.364 | 45.662 | 33.478 | 1.00 | 15.16 |
| ATOM | 252 | O | ASN | A | 249 | 17.157 | 44.510 | 38.066 | 1.00 | 13.94 |
| ATOM | 253 | N | TYR | A | 250 | 16.650 | 46.170 | 39.578 | 1.00 | 14.10 |
| ATOM | 254 | CA | TYR | A | 250 | 15.888 | 45.426 | 40.360 | 1.00 | 15.67 |
| ATOM | 255 | CB | TYR | A | 250 | 16.393 | 46.239 | 41.546 | 1.00 | 16.52 |
| ATOM | 256 | CG | TYR | A | 250 | 14.527 | 45.444 | 42.501 | 1.00 | 18.76 |
| ATOM | 257 | CD1 | TYR | A | 250 | 15.109 | 44.778 | 43.571 | 1.00 | 20.38 |
| ATOM | 258 | CE1 | TYR | A | 250 | 14.344 | 44.031 | 44.447 | 1.00 | 21.56 |
| ATOM | 259 | CD2 | TYR | A | 250 | 13.138 | 45.344 | 42.332 | 1.00 | 18.76 |
| ATOM | 260 | CE2 | TYR | A | 250 | 12.377 | 44.600 | 43.203 | 1.00 | 19.63 |
| ATOM | 261 | CZ | TYR | A | 250 | 12.985 | 43.943 | 44.248 | 1.00 | 22.22 |
| ATOM | 262 | OH | TYR | A | 250 | 12.250 | 43.189 | 45.134 | 1.00 | 24.91 |
| ATOM | 263 | C | TYR | A | 250 | 14.683 | 45.029 | 39.472 | 1.00 | 14.95 |
| ATOM | 264 | O | TYR | A | 250 | 14.234 | 43.893 | 39.546 | 1.00 | 11.83 |
| ATOM | 265 | N | LEU | A | 251 | 14.133 | 46.031 | 38.758 | 1.00 | 13.07 |
| ATOM | 266 | CA | LEU | A | 251 | 12.977 | 45.742 | 37.899 | 1.00 | 12.72 |
| ATOM | 267 | CB | LEU | A | 251 | 12.271 | 47.059 | 37.519 | 1.00 | 12.66 |
| ATOM | 268 | CG | LEU | A | 251 | 11.696 | 47.800 | 38.734 | 1.00 | 14.96 |
| ATOM | 269 | CD1 | LEU | A | 251 | 11.038 | 49.099 | 38.363 | 1.00 | 18.53 |
| ATOM | 270 | CD2 | LEU | A | 251 | 10.717 | 46.914 | 39.501 | 1.00 | 19.00 |
| ATOM | 271 | C | LEU | A | 251 | 13.288 | 44.885 | 36.700 | 1.00 | 11.35 |
| ATOM | 272 | O | LEU | A | 251 | 12.518 | 43.962 | 36.349 | 1.00 | 10.33 |
| ATOM | 273 | N | ILE | A | 252 | 14.429 | 45.093 | 36.050 | 1.00 | 10.29 |
| ATOM | 274 | CA | ILE | A | 252 | 14.832 | 44.209 | 34.944 | 1.00 | 12.09 |
| ATOM | 275 | CB | ILE | A | 252 | 16.209 | 44.654 | 34.372 | 1.00 | 13.58 |
| ATOM | 276 | CG2 | ILE | A | 252 | 16.848 | 43.570 | 33.523 | 1.00 | 14.17 |
| ATOM | 277 | CG1 | ILE | A | 252 | 16.059 | 45.964 | 33.581 | 1.00 | 16.57 |
| ATOM | 278 | CD1 | ILE | A | 252 | 17.351 | 46.450 | 32.902 | 1.00 | 18.53 |
| ATOM | 279 | C | ILE | A | 252 | 14.938 | 42.791 | 35.448 | 1.00 | 10.51 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 280 O | ILE | A | 252 | 14.592 | 41.830 | 34.755 | 1.00 | 12.14 |
| ATOM | 281 N | GLU | A | 253 | 15.508 | 42.598 | 36.641 | 1.00 | 9.27 |
| ATOM | 282 CA | GLU | A | 253 | 15.743 | 41.263 | 37.159 | 1.00 | 10.71 |
| ATOM | 283 CB | GLU | A | 253 | 16.762 | 41.233 | 38.306 | 1.00 | 12.25 |
| ATOM | 284 CG | GLU | A | 253 | 18.217 | 41.412 | 37.830 | 1.00 | 12.76 |
| ATOM | 285 CD | GLU | A | 253 | 19.215 | 41.029 | 38.924 | 1.00 | 15.62 |
| ATOM | 286 CE1 | GLU | A | 253 | 19.091 | 40.009 | 39.615 | 1.00 | 14.92 |
| ATOM | 287 OE2 | GLU | A | 253 | 20.134 | 41.798 | 39.207 | 1.00 | 14.69 |
| ATOM | 288 C | GLU | A | 253 | 14.422 | 40.619 | 37.605 | 1.00 | 9.88 |
| ATOM | 289 O | GLU | A | 253 | 14.195 | 39.441 | 37.388 | 1.00 | 7.43 |
| ATOM | 290 N | LEU | A | 254 | 13.559 | 41.420 | 38.230 | 1.00 | 10.47 |
| ATOM | 291 CA | LEU | A | 254 | 12.266 | 40.858 | 38.649 | 1.00 | 10.04 |
| ATOM | 292 CB | LEU | A | 254 | 11.537 | 41.807 | 39.572 | 1.00 | 9.52 |
| ATOM | 293 CG | LEU | A | 254 | 10.103 | 41.493 | 40.022 | 1.00 | 10.99 |
| ATOM | 294 CD1 | LEU | A | 254 | 9.778 | 42.322 | 41.239 | 1.00 | 11.71 |
| ATOM | 295 CD2 | LEU | A | 254 | 9.106 | 41.854 | 33.918 | 1.00 | 11.46 |
| ATOM | 296 C | LEU | A | 254 | 11.481 | 40.463 | 37.408 | 1.00 | 9.41 |
| ATOM | 297 O | LEU | A | 254 | 10.959 | 39.343 | 37.426 | 1.00 | 10.16 |
| ATOM | 298 N | ILE | A | 255 | 11.399 | 41.269 | 36.369 | 1.00 | 11.15 |
| ATOM | 299 CA | ILE | A | 255 | 10.590 | 40.910 | 35.180 | 1.00 | 11.06 |
| ATOM | 300 CB | ILE | A | 255 | 10.480 | 42.108 | 34.194 | 1.00 | 10.34 |
| ATOM | 301 CG2 | ILE | A | 255 | 9.910 | 41.651 | 32.851 | 1.00 | 12.31 |
| ATOM | 302 CG1 | ILE | A | 255 | 9.646 | 43.216 | 34.796 | 1.00 | 10.06 |
| ATOM | 303 CD1 | ILE | A | 255 | 8.235 | 42.810 | 35.286 | 1.00 | 10.96 |
| ATOM | 304 C | ILE | A | 255 | 11.113 | 39.671 | 34.495 | 1.00 | 11.34 |
| ATOM | 305 O | ILE | A | 255 | 10.466 | 38.704 | 34.055 | 1.00 | 8.95 |
| ATOM | 306 N | ASP | A | 256 | 12.458 | 39.596 | 34.420 | 1.00 | 10.09 |
| ATOM | 307 CA | ASP | A | 256 | 13.108 | 38.362 | 33.953 | 1.00 | 11.00 |
| ATOM | 308 CB | ASP | A | 256 | 14.621 | 38.617 | 33.890 | 1.00 | 12.60 |
| ATOM | 309 CG | ASP | A | 256 | 15.320 | 37.358 | 33.434 | 1.00 | 16.54 |
| ATOM | 310 OD1 | ASP | A | 256 | 15.159 | 37.033 | 32.249 | 1.00 | 17.04 |
| ATOM | 311 OD2 | ASP | A | 256 | 15.977 | 36.731 | 34.290 | 1.00 | 18.15 |
| ATOM | 312 C | ASP | A | 256 | 12.763 | 37.124 | 34.779 | 1.00 | 10.53 |
| ATOM | 313 O | ASP | A | 256 | 12.485 | 36.036 | 34.246 | 1.00 | 11.14 |
| ATOM | 314 N | ARG | A | 257 | 12.719 | 37.177 | 36.087 | 1.00 | 11.51 |
| ATOM | 315 CA | ARG | A | 257 | 12.362 | 36.025 | 36.523 | 1.00 | 11.03 |
| ATOM | 316 CB | ARG | A | 257 | 12.646 | 36.291 | 38.375 | 1.00 | 11.04 |
| ATOM | 317 CG | ARG | A | 257 | 14.194 | 36.302 | 38.743 | 1.00 | 9.97 |
| ATOM | 318 CD | ARG | A | 257 | 14.347 | 36.333 | 40.258 | 1.00 | 9.34 |
| ATOM | 319 NE | ARG | A | 257 | 13.581 | 37.392 | 40.951 | 1.00 | 9.56 |
| ATOM | 320 CZ | ARG | A | 257 | 14.058 | 38.613 | 41.124 | 1.00 | 10.48 |
| ATOM | 321 NH1 | ARG | A | 257 | 15.283 | 38.961 | 40.677 | 1.00 | 8.64 |
| ATOM | 322 NH2 | ARG | A | 257 | 13.363 | 39.539 | 41.718 | 1.00 | 8.45 |
| ATOM | 323 C | ARG | A | 257 | 10.868 | 35.673 | 36.655 | 1.00 | 10.99 |
| ATOM | 324 O | ARG | A | 257 | 10.495 | 34.509 | 36.580 | 1.00 | 10.38 |
| ATOM | 325 N | VAL | A | 258 | 10.033 | 36.685 | 36.635 | 1.00 | 7.90 |
| ATOM | 326 CA | VAL | A | 258 | 8.600 | 36.497 | 36.295 | 1.00 | 9.48 |
| ATOM | 327 CB | VAL | A | 258 | 7.877 | 37.856 | 36.335 | 1.00 | 8.97 |
| ATOM | 328 CG1 | VAL | A | 258 | 6.398 | 37.717 | 35.905 | 1.00 | 7.38 |
| ATOM | 329 CG2 | VAL | A | 258 | 7.915 | 38.447 | 37.733 | 1.00 | 7.76 |
| ATOM | 330 C | VAL | A | 258 | 8.469 | 35.851 | 34.931 | 1.00 | 9.20 |
| ATOM | 331 O | VAL | A | 258 | 7.769 | 34.858 | 34.706 | 1.00 | 11.73 |
| ATOM | 332 N | ASP | A | 259 | 9.193 | 36.330 | 33.947 | 1.00 | 10.44 |
| ATOM | 333 CA | ASP | A | 259 | 9.196 | 35.817 | 32.585 | 1.00 | 11.92 |
| ATOM | 334 CB | ASP | A | 259 | 10.101 | 36.614 | 31.655 | 1.00 | 12.64 |
| ATOM | 335 CG | ASP | A | 259 | 10.059 | 36.157 | 30.219 | 1.00 | 17.49 |
| ATOM | 336 OD1 | ASP | A | 259 | 8.962 | 36.007 | 29.644 | 1.00 | 16.26 |
| ATOM | 337 OD2 | ASP | A | 259 | 11.145 | 35.932 | 29.637 | 1.00 | 20.54 |
| ATOM | 338 C | ASP | A | 259 | 9.618 | 34.346 | 32.546 | 1.00 | 13.21 |
| ATOM | 339 O | ASP | A | 259 | 9.021 | 33.572 | 31.783 | 1.00 | 11.13 |
| ATOM | 340 N | ASP | A | 260 | 10.546 | 33.904 | 33.412 | 1.00 | 12.46 |
| ATOM | 341 OD2 | ASP | A | 260 | 14.081 | 33.042 | 35.067 | 1.00 | 19.42 |
| ATOM | 342 OD1 | ASP | A | 260 | 13.629 | 33.074 | 32.936 | 1.00 | 15.68 |
| ATOM | 343 CG | ASP | A | 260 | 13.335 | 32.789 | 34.098 | 1.00 | 16.09 |
| ATOM | 344 CB | ASP | A | 260 | 11.972 | 32.171 | 34.451 | 1.00 | 13.52 |
| ATOM | 345 CA | ASP | A | 260 | 10.912 | 32.498 | 33.403 | 1.00 | 11.20 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 346 C | ASP | A | 260 | 9.647 | 31.669 | 33.761 | 1.00 | 13.45 |
| ATOM | 347 O | ASP | A | 260 | 9.461 | 30.565 | 33.241 | 1.00 | 11.34 |
| ATOM | 348 N | ILE | A | 261 | 8.867 | 32.202 | 34.720 | 1.00 | 10.81 |
| ATOM | 349 CA | ILE | A | 261 | 7.643 | 31.469 | 35.052 | 1.00 | 11.86 |
| ATOM | 350 CB | ILE | A | 261 | 6.910 | 32.167 | 36.198 | 1.00 | 13.06 |
| ATOM | 351 CG2 | ILE | A | 261 | 5.538 | 31.612 | 36.416 | 1.00 | 12.50 |
| ATOM | 252 CG1 | ILE | A | 261 | 7.825 | 31.986 | 37.422 | 1.00 | 16.02 |
| ATOM | 353 CD1 | ILE | A | 261 | 7.242 | 32.547 | 38.701 | 1.00 | 17.40 |
| ATOM | 354 C | ILE | A | 261 | 6.738 | 31.396 | 33.815 | 1.00 | 10.07 |
| ATOM | 355 O | ILE | A | 261 | 6.351 | 30.273 | 33.480 | 1.00 | 11.72 |
| ATOM | 356 N | TYR | A | 262 | 6.434 | 32.522 | 33.232 | 1.00 | 8.70 |
| ATOM | 357 CA | TYR | A | 262 | 5.515 | 32.515 | 32.082 | 1.00 | 11.55 |
| ATOM | 358 CB | TYR | A | 262 | 5.275 | 33.937 | 31.548 | 1.00 | 11.91 |
| ATOM | 359 CG | TYR | A | 262 | 4.257 | 34.650 | 32.411 | 1.00 | 12.15 |
| ATOM | 360 CD1 | TYR | A | 262 | 4.554 | 35.110 | 33.670 | 1.00 | 12.29 |
| ATOM | 361 CE1 | TYR | A | 262 | 3.598 | 35.746 | 34.457 | 1.00 | 12.53 |
| ATOM | 362 CD2 | TYR | A | 262 | 2.940 | 34.799 | 31.941 | 1.00 | 14.52 |
| ATOM | 363 CE2 | TYR | A | 262 | 1.989 | 35.420 | 32.716 | 1.00 | 14.04 |
| ATOM | 364 CZ | TYR | A | 262 | 2.315 | 35.905 | 33.956 | 1.00 | 14.14 |
| ATOM | 365 OH | TYR | A | 262 | 1.368 | 36.538 | 34.724 | 1.00 | 12.39 |
| ATOM | 366 C | TYR | A | 262 | 5.982 | 31.682 | 30.932 | 1.00 | 11.66 |
| ATOM | 367 O | TYR | A | 262 | 5.202 | 30.842 | 30.446 | 1.00 | 11.39 |
| ATOM | 368 N | ARG | A | 263 | 7.231 | 31.887 | 30.478 | 1.00 | 10.78 |
| ATOM | 369 CA | ARG | A | 263 | 7.771 | 31.380 | 29.333 | 1.00 | 14.61 |
| ATOM | 370 CB | ARG | A | 263 | 9.236 | 31.623 | 29.117 | 1.00 | 18.66 |
| ATOM | 371 CG | ARG | A | 263 | 9.634 | 32.729 | 28.194 | 1.00 | 21.81 |
| ATOM | 372 CD | ARG | A | 263 | 11.103 | 32.655 | 27.718 | 1.00 | 25.82 |
| ATOM | 373 NE | ARG | A | 263 | 11.932 | 31.745 | 28.516 | 1.00 | 27.30 |
| ATOM | 374 CZ | ARG | A | 263 | 12.427 | 32.092 | 29.708 | 1.00 | 28.71 |
| ATOM | 375 NH1 | ARG | A | 263 | 12.225 | 33.329 | 30.166 | 1.00 | 29.09 |
| ATOM | 376 NH2 | ARG | A | 263 | 13.087 | 33.212 | 30.435 | 1.00 | 27.05 |
| ATOM | 377 C | ARG | A | 263 | 7.751 | 29.674 | 29.425 | 1.00 | 15.13 |
| ATOM | 378 O | ARG | A | 263 | 7.596 | 28.973 | 28.384 | 1.00 | 17.45 |
| ATOM | 379 N | ASN | A | 264 | 8.019 | 29.078 | 30.591 | 1.00 | 12.82 |
| ATOM | 380 CA | ASN | A | 264 | 8.003 | 27.677 | 30.834 | 1.00 | 14.56 |
| ATOM | 381 CB | ASN | A | 264 | 8.878 | 27.204 | 32.013 | 1.00 | 17.95 |
| ATOM | 382 CG | ASN | A | 264 | 10.323 | 27.555 | 31.654 | 1.00 | 19.62 |
| ATOM | 383 OD1 | ASN | A | 264 | 10.776 | 27.002 | 30.654 | 1.00 | 23.35 |
| ATOM | 384 ND2 | ASN | A | 264 | 10.957 | 28.464 | 32.335 | 1.00 | 19.81 |
| ATOM | 385 C | ASN | A | 264 | 6.582 | 27.144 | 31.076 | 1.00 | 16.00 |
| ATOM | 386 O | ASN | A | 264 | 6.449 | 25.944 | 31.293 | 1.00 | 14.82 |
| ATOM | 387 N | THR | A | 265 | 5.566 | 28.017 | 31.073 | 1.00 | 13.74 |
| ATOM | 388 CA | THR | A | 265 | 4.221 | 27.425 | 31.290 | 1.00 | 13.37 |
| ATOM | 389 CB | THR | A | 265 | 3.309 | 28.463 | 31.935 | 1.00 | 14.37 |
| ATOM | 390 OG1 | THR | A | 265 | 3.800 | 28.787 | 33.238 | 1.00 | 11.71 |
| ATOM | 391 CG2 | THR | A | 265 | 1.866 | 27.953 | 32.101 | 1.00 | 12.84 |
| ATOM | 392 C | THR | A | 265 | 3.675 | 26.917 | 29.965 | 1.00 | 12.82 |
| ATOM | 393 O | THR | A | 265 | 3.698 | 27.828 | 28.968 | 1.00 | 14.37 |
| ATOM | 394 N | ALA | A | 266 | 3.134 | 25.708 | 29.970 | 1.00 | 13.65 |
| ATOM | 395 CA | ALA | A | 266 | 2.432 | 25.151 | 28.820 | 1.00 | 14.19 |
| ATOM | 396 CB | ALA | A | 266 | 2.737 | 23.645 | 28.812 | 1.00 | 14.17 |
| ATOM | 397 C | ALA | A | 266 | 0.937 | 25.431 | 28.997 | 1.00 | 11.04 |
| ATOM | 398 O | ALA | A | 266 | 0.250 | 24.682 | 29.675 | 1.00 | 10.22 |
| ATOM | 399 N | TRP | A | 267 | 0.426 | 26.539 | 28.524 | 1.00 | 11.35 |
| ATOM | 400 CA | TRP | A | 267 | −0.962 | 26.949 | 28.736 | 1.00 | 13.04 |
| ATOM | 401 CB | TRP | A | 267 | −1.183 | 28.301 | 28.045 | 1.00 | 11.63 |
| ATOM | 402 CG | TRP | A | 267 | −0.186 | 29.330 | 28.523 | 1.00 | 10.70 |
| ATOM | 403 CD2 | TRP | A | 267 | −0.205 | 29.920 | 29.819 | 1.00 | 8.77 |
| ATOM | 404 CE2 | TRP | A | 267 | 0.904 | 30.814 | 29.863 | 1.00 | 12.19 |
| ATOM | 405 CE3 | TRP | A | 267 | −1.007 | 29.828 | 30.931 | 1.00 | 9.72 |
| ATOM | 406 CD1 | TRP | A | 267 | 0.865 | 29.846 | 27.849 | 1.00 | 10.38 |
| ATOM | 407 NE1 | TRP | A | 267 | 1.531 | 30.754 | 28.652 | 1.00 | 11.35 |
| ATOM | 408 CZ2 | TRP | A | 267 | 1.187 | 31.580 | 30.989 | 1.00 | 10.57 |
| ATOM | 409 CZ3 | TRP | A | 267 | −0.718 | 30.580 | 32.066 | 1.00 | 11.82 |
| ATOM | 410 CH2 | TRP | A | 267 | 0.395 | 31.439 | 32.071 | 1.00 | 9.78 |
| ATOM | 411 C | TRP | A | 267 | −2.007 | 25.919 | 28.298 | 1.00 | 14.01 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 412 O | TRP | A | 267 | −3.089 | 25.832 | 28.915 | 1.00 | 14.19 |
| ATOM | 413 N | ASP | A | 268 | −1.688 | 25.091 | 27.326 | 1.00 | 11.86 |
| ATOM | 414 CA | ASP | A | 268 | −2.615 | 24.026 | 26.899 | 1.00 | 13.82 |
| ATOM | 415 CB | ASP | A | 268 | −2.765 | 24.051 | 25.382 | 1.00 | 13.92 |
| ATOM | 416 CG | ASP | A | 268 | −1.517 | 23.691 | 24.619 | 1.00 | 16.74 |
| ATOM | 417 OD1 | ASP | A | 268 | −0.422 | 23.699 | 25.244 | 1.00 | 16.49 |
| ATOM | 418 OD2 | ASP | A | 268 | −1.561 | 23.395 | 23.404 | 1.00 | 15.38 |
| ATOM | 419 C | ASP | A | 268 | −2.165 | 22.661 | 27.367 | 1.00 | 15.26 |
| ATOM | 420 O | ASP | A | 268 | −2.554 | 21.608 | 26.834 | 1.00 | 13.18 |
| ATOM | 421 N | ASN | A | 269 | −1.225 | 22.609 | 28.329 | 1.00 | 14.90 |
| ATOM | 422 CA | ASN | A | 269 | −0.596 | 21.391 | 28.792 | 1.00 | 15.45 |
| ATOM | 423 CB | ASN | A | 269 | −1.547 | 20.454 | 29.549 | 1.00 | 17.28 |
| ATOM | 424 CG | ASN | A | 269 | −2.190 | 21.182 | 30.719 | 1.00 | 18.96 |
| ATOM | 425 OD1 | ASN | A | 269 | −1.464 | 21.670 | 31.560 | 1.00 | 20.34 |
| ATOM | 426 ND2 | ASN | A | 269 | −3.500 | 21.321 | 30.788 | 1.00 | 18.93 |
| ATOM | 427 C | ASN | A | 269 | 0.108 | 20.556 | 27.711 | 1.00 | 14.79 |
| ATOM | 428 O | ASN | A | 269 | 0.330 | 19.352 | 27.859 | 1.00 | 14.35 |
| ATOM | 429 N | ALA | A | 270 | 0.523 | 21.193 | 26.654 | 1.00 | 14.55 |
| ATOM | 430 CA | ALA | A | 270 | 1.203 | 20.593 | 25.533 | 1.00 | 17.42 |
| ATOM | 431 CB | ALA | A | 270 | 0.189 | 20.155 | 24.481 | 1.00 | 15.76 |
| ATOM | 432 C | ALA | A | 270 | 2.239 | 21.573 | 25.004 | 1.00 | 16.67 |
| ATOM | 433 O | ALA | A | 270 | 3.183 | 21.866 | 25.757 | 1.00 | 19.13 |
| ATOM | 434 N | GLY | A | 271 | 2.141 | 22.004 | 23.765 | 1.00 | 16.01 |
| ATOM | 435 CA | GLY | A | 271 | 3.174 | 22.837 | 23.177 | 1.00 | 18.64 |
| ATOM | 436 C | GLY | A | 271 | 2.951 | 24.321 | 23.125 | 1.00 | 17.56 |
| ATOM | 437 O | GLY | A | 271 | 3.768 | 25.075 | 22.589 | 1.00 | 18.20 |
| ATOM | 438 N | PHE | A | 272 | 1.844 | 24.831 | 23.659 | 1.00 | 17.81 |
| ATOM | 439 CA | PHE | A | 272 | 1.538 | 26.263 | 23.614 | 1.00 | 16.42 |
| ATOM | 440 CB | PHE | A | 272 | 0.047 | 26.539 | 23.710 | 1.00 | 16.73 |
| ATOM | 441 CG | PHE | A | 272 | −0.389 | 27.890 | 23.205 | 1.00 | 17.94 |
| ATOM | 442 CD1 | PHE | A | 272 | −0.462 | 28.168 | 21.858 | 1.00 | 19.17 |
| ATOM | 443 CD2 | PHE | A | 272 | −0.716 | 28.894 | 24.100 | 1.00 | 18.80 |
| ATOM | 444 CE1 | PHE | A | 272 | −0.813 | 29.421 | 23.407 | 1.00 | 18.87 |
| ATOM | 445 CE2 | PHE | A | 272 | −1.120 | 30.139 | 23.664 | 1.00 | 18.81 |
| ATOM | 446 CZ | PHE | A | 272 | −1.142 | 30.404 | 22.310 | 1.00 | 19.11 |
| ATOM | 447 C | PHE | A | 272 | 2.305 | 26.889 | 24.796 | 1.00 | 16.83 |
| ATOM | 448 O | PHE | A | 272 | 1.786 | 27.138 | 25.860 | 1.00 | 14.19 |
| ATOM | 449 N | LYS | A | 273 | 3.584 | 27.067 | 24.561 | 1.00 | 17.93 |
| ATOM | 450 CA | LYS | A | 273 | 4.522 | 27.543 | 25.546 | 1.00 | 21.35 |
| ATOM | 451 CB | LYS | A | 273 | 5.236 | 26.296 | 26.080 | 1.00 | 24.32 |
| ATOM | 452 CG | LYS | A | 273 | 6.157 | 25.698 | 25.023 | 1.00 | 27.94 |
| ATOM | 453 CD | LYS | A | 273 | 6.625 | 24.300 | 25.389 | 1.00 | 31.29 |
| ATOM | 454 CE | LYS | A | 273 | 7.307 | 24.300 | 26.732 | 1.00 | 32.80 |
| ATOM | 455 NZ | LYS | A | 273 | 6.347 | 24.136 | 27.857 | 1.00 | 33.38 |
| ATOM | 456 C | LYS | A | 273 | 5.479 | 28.518 | 24.906 | 1.00 | 19.96 |
| ATOM | 457 O | LYS | A | 273 | 5.444 | 28.763 | 23.706 | 1.00 | 18.61 |
| ATOM | 458 N | GLY | A | 274 | 6.382 | 29.094 | 25.709 | 1.00 | 20.59 |
| ATOM | 459 CA | GLY | A | 274 | 7.323 | 30.058 | 25.166 | 1.00 | 17.10 |
| ATOM | 460 C | GLY | A | 274 | 6.701 | 31.449 | 25.153 | 1.00 | 17.80 |
| ATOM | 461 O | GLY | A | 274 | 7.272 | 32.334 | 24.547 | 1.00 | 17.48 |
| ATOM | 462 N | TYR | A | 275 | 5.527 | 31.675 | 25.763 | 1.00 | 15.67 |
| ATOM | 463 CA | TYR | A | 275 | 4.892 | 32.965 | 25.302 | 1.00 | 16.24 |
| ATOM | 464 CB | TYR | A | 275 | 3.340 | 32.874 | 25.854 | 1.00 | 15.81 |
| ATOM | 465 CG | TYR | A | 275 | 2.838 | 32.446 | 24.503 | 1.00 | 17.73 |
| ATOM | 466 CD1 | TYR | A | 275 | 2.784 | 31.102 | 24.175 | 1.00 | 17.51 |
| ATOM | 467 CE1 | TYR | A | 275 | 2.384 | 30.722 | 22.919 | 1.00 | 20.42 |
| ATOM | 468 CD2 | TYR | A | 275 | 2.524 | 33.418 | 23.543 | 1.00 | 18.48 |
| ATOM | 469 CE2 | TYR | A | 275 | 2.140 | 33.017 | 22.279 | 1.00 | 20.02 |
| ATOM | 470 CZ | TYR | A | 275 | 2.065 | 31.690 | 21.989 | 1.00 | 19.42 |
| ATOM | 471 OH | TYR | A | 275 | 1.670 | 31.304 | 20.737 | 1.00 | 23.70 |
| ATOM | 472 C | TYR | A | 275 | 5.317 | 33.689 | 27.087 | 1.00 | 15.60 |
| ATOM | 473 O | TYR | A | 275 | 5.270 | 33.077 | 28.160 | 1.00 | 15.87 |
| ATOM | 474 N | GLY | A | 276 | 5.638 | 34.959 | 26.991 | 1.00 | 17.04 |
| ATOM | 475 CA | GLY | A | 276 | 5.978 | 35.692 | 28.390 | 1.00 | 17.48 |
| ATOM | 476 C | GLY | A | 276 | 5.988 | 37.183 | 28.020 | 1.00 | 19.17 |
| ATOM | 477 O | GLY | A | 276 | 5.226 | 37.781 | 27.278 | 1.00 | 16.76 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 478 N | ILE | A | 277 | 6.893 | 37.805 | 28.811 | 1.00 | 18.66 |
| ATOM | 479 CA | ILE | A | 277 | 6.938 | 39.245 | 28.907 | 1.00 | 17.89 |
| ATOM | 480 CB | ILE | A | 277 | 6.413 | 39.745 | 30.256 | 1.00 | 19.63 |
| ATOM | 481 CG2 | ILE | A | 277 | 4.925 | 39.409 | 30.421 | 1.00 | 21.02 |
| ATOM | 482 CG1 | ILE | A | 277 | 7.212 | 39.101 | 31.390 | 1.00 | 20.19 |
| ATOM | 483 CD1 | ILE | A | 277 | 6.754 | 39.439 | 32.779 | 1.00 | 20.94 |
| ATOM | 484 C | ILE | A | 277 | 8.385 | 39.741 | 28.763 | 1.00 | 18.46 |
| ATOM | 485 O | ILE | A | 277 | 9.318 | 39.076 | 29.168 | 1.00 | 16.61 |
| ATOM | 486 N | GLN | A | 278 | 8.505 | 40.919 | 28.219 | 1.00 | 17.96 |
| ATOM | 487 CA | GLN | A | 278 | 9.743 | 41.629 | 28.051 | 1.00 | 19.65 |
| ATOM | 488 CB | GLN | A | 278 | 10.224 | 41.684 | 26.624 | 1.00 | 25.01 |
| ATOM | 489 CG | GLN | A | 278 | 11.692 | 41.405 | 26.382 | 1.00 | 28.24 |
| ATOM | 490 CD | GLN | A | 278 | 11.580 | 40.059 | 25.643 | 1.00 | 32.63 |
| ATOM | 491 OE1 | GLN | A | 278 | 11.660 | 40.060 | 24.422 | 1.00 | 33.32 |
| ATOM | 492 NE2 | GLN | A | 278 | 11.331 | 39.078 | 26.502 | 1.00 | 34.14 |
| ATOM | 493 C | GLN | A | 278 | 9.499 | 43.122 | 28.316 | 1.00 | 17.44 |
| ATOM | 494 O | GLN | A | 278 | 8.589 | 43.689 | 27.693 | 1.00 | 14.22 |
| ATOM | 495 N | ILE | A | 279 | 10.537 | 43.709 | 28.900 | 1.00 | 13.53 |
| ATOM | 496 CA | ILE | A | 279 | 10.471 | 45.146 | 29.090 | 1.00 | 15.82 |
| ATOM | 497 CB | ILE | A | 279 | 11.441 | 45.658 | 30.183 | 1.00 | 15.54 |
| ATOM | 498 CG2 | ILE | A | 279 | 11.402 | 47.166 | 30.140 | 1.00 | 15.97 |
| ATOM | 499 CG1 | ILE | A | 279 | 11.007 | 45.083 | 31.520 | 1.00 | 16.27 |
| ATOM | 500 CD1 | ILE | A | 279 | 11.940 | 45.388 | 32.661 | 1.00 | 17.52 |
| ATOM | 501 C | ILE | A | 279 | 10.745 | 45.847 | 27.771 | 1.00 | 16.97 |
| ATOM | 502 O | ILE | A | 279 | 11.741 | 45.578 | 27.115 | 1.00 | 16.40 |
| ATOM | 503 N | GLU | A | 280 | 9.824 | 46.719 | 27.370 | 1.00 | 17.63 |
| ATOM | 504 CA | GLU | A | 280 | 10.019 | 47.523 | 26.185 | 1.00 | 20.86 |
| ATOM | 505 CB | GLU | A | 280 | 8.744 | 47.778 | 25.395 | 1.00 | 23.07 |
| ATOM | 506 CG | GLU | A | 280 | 8.890 | 48.784 | 24.268 | 1.00 | 29.11 |
| ATOM | 507 CD | GLU | A | 280 | 9.843 | 48.327 | 23.189 | 1.00 | 32.61 |
| ATOM | 508 OE1 | GLU | A | 280 | 10.187 | 47.124 | 23.154 | 1.00 | 36.14 |
| ATOM | 509 OE2 | GLU | A | 280 | 10.293 | 49.127 | 22.343 | 1.00 | 34.84 |
| ATOM | 510 C | GLU | A | 280 | 10.599 | 48.892 | 26.605 | 1.00 | 18.21 |
| ATOM | 511 O | GLU | A | 280 | 11.426 | 49.511 | 25.941 | 1.00 | 16.53 |
| ATOM | 512 N | GLU | A | 281 | 10.088 | 49.380 | 27.716 | 1.00 | 18.36 |
| ATOM | 513 NE2 | GLN | A | 281 | 11.497 | 53.112 | 26.056 | 1.00 | 34.24 |
| ATOM | 514 OE1 | GLN | A | 281 | 10.702 | 55.093 | 26.755 | 1.00 | 36.11 |
| ATOM | 515 CD | GLN | A | 281 | 10.798 | 53.869 | 26.901 | 1.00 | 33.14 |
| ATOM | 516 CG | GLN | A | 281 | 10.120 | 53.163 | 28.056 | 1.00 | 29.67 |
| ATOM | 517 CB | GLN | A | 281 | 9.611 | 51.793 | 27.640 | 1.00 | 24.17 |
| ATOM | 518 CA | GLN | A | 281 | 10.509 | 50.675 | 28.207 | 1.00 | 21.85 |
| ATOM | 519 C | GLN | A | 281 | 10.385 | 50.730 | 29.723 | 1.00 | 22.08 |
| ATOM | 520 O | GLN | A | 281 | 9.444 | 50.170 | 30.275 | 1.00 | 19.43 |
| ATOM | 521 N | ILE | A | 282 | 11.379 | 51.377 | 30.337 | 1.00 | 19.26 |
| ATOM | 522 CA | ILE | A | 282 | 11.340 | 51.564 | 31.756 | 1.00 | 20.21 |
| ATOM | 523 CB | ILE | A | 282 | 12.456 | 50.838 | 32.501 | 1.00 | 23.17 |
| ATOM | 524 CG2 | ILE | A | 282 | 12.567 | 51.331 | 33.942 | 1.00 | 22.63 |
| ATOM | 525 CG1 | ILE | A | 282 | 12.183 | 49.337 | 32.486 | 1.00 | 24.53 |
| ATOM | 526 CD1 | ILE | A | 282 | 13.292 | 48.530 | 33.126 | 1.00 | 27.43 |
| ATOM | 527 C | ILE | A | 282 | 13.408 | 53.062 | 32.033 | 1.00 | 20.13 |
| ATOM | 528 O | ILE | A | 282 | 12.183 | 53.826 | 31.441 | 1.00 | 21.53 |
| ATOM | 529 N | ARG | A | 283 | 10.595 | 53.478 | 32.972 | 1.00 | 18.99 |
| ATOM | 530 CA | ARG | A | 283 | 10.541 | 54.878 | 33.353 | 1.00 | 20.71 |
| ATOM | 531 CB | ARG | A | 283 | 9.159 | 55.499 | 33.116 | 1.00 | 23.74 |
| ATOM | 532 CG | ARG | A | 283 | 8.779 | 55.516 | 31.645 | 1.00 | 28.61 |
| ATOM | 533 CD | ARG | A | 283 | 9.030 | 56.887 | 31.041 | 1.00 | 33.16 |
| ATOM | 534 NE | ARG | A | 283 | 9.596 | 56.759 | 29.712 | 1.00 | 37.40 |
| ATOM | 535 CZ | ARG | A | 283 | 9.199 | 57.449 | 28.659 | 1.00 | 40.44 |
| ATOM | 536 NH1 | ARG | A | 283 | 8.191 | 58.311 | 28.783 | 1.00 | 41.71 |
| ATOM | 537 NH2 | ARG | A | 283 | 9.800 | 57.245 | 27.492 | 1.00 | 41.03 |
| ATOM | 538 C | ARG | A | 283 | 10.826 | 54.930 | 34.844 | 1.00 | 20.40 |
| ATOM | 539 O | ARG | A | 283 | 10.049 | 54.339 | 35.566 | 1.00 | 17.37 |
| ATOM | 540 N | ILE | A | 284 | 11.881 | 55.634 | 35.220 | 1.00 | 18.94 |
| ATOM | 541 CA | ILE | A | 284 | 12.127 | 55.779 | 36.655 | 1.00 | 19.58 |
| ATOM | 542 CB | ILE | A | 284 | 13.582 | 55.519 | 37.053 | 1.00 | 20.09 |
| ATOM | 543 CG2 | ILE | A | 284 | 13.684 | 55.477 | 38.573 | 1.00 | 20.97 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 544 CG1 | ILE | A | 284 | 14.178 | 54.254 | 36.460 | 1.00 | 20.86 |
| ATOM | 545 CD1 | ILE | A | 284 | 13.442 | 52.976 | 36.774 | 1.00 | 20.01 |
| ATOM | 546 C | ILE | A | 284 | 11.792 | 57.228 | 37.002 | 1.00 | 19.71 |
| ATOM | 547 O | ILE | A | 284 | 12.399 | 58.147 | 36.427 | 1.00 | 19.08 |
| ATOM | 548 N | LEU | A | 285 | 10.816 | 57.413 | 37.849 | 1.00 | 19.33 |
| ATOM | 549 CA | LEU | A | 285 | 10.379 | 58.729 | 38.276 | 1.00 | 20.90 |
| ATOM | 550 CB | LEU | A | 285 | 8.881 | 58.729 | 38.557 | 1.00 | 20.57 |
| ATOM | 551 CG | LEU | A | 285 | 8.020 | 58.220 | 37.391 | 1.00 | 18.92 |
| ATOM | 552 CD1 | LEU | A | 285 | 6.569 | 58.488 | 37.719 | 1.00 | 19.77 |
| ATOM | 553 CD2 | LEU | A | 285 | 8.426 | 58.759 | 36.039 | 1.00 | 18.79 |
| ATOM | 554 C | LEU | A | 285 | 11.153 | 59.078 | 39.542 | 1.00 | 22.65 |
| ATOM | 555 O | LEU | A | 285 | 10.861 | 58.536 | 40.585 | 1.00 | 21.09 |
| ATOM | 556 N | LYS | A | 286 | 12.179 | 59.897 | 39.370 | 1.00 | 23.47 |
| ATOM | 557 CA | LYS | A | 286 | 13.101 | 60.223 | 40.443 | 1.00 | 25.88 |
| ATOM | 558 CB | LYS | A | 286 | 14.400 | 60.777 | 39.830 | 1.00 | 24.64 |
| ATOM | 559 CG | LYS | A | 286 | 15.057 | 59.703 | 38.969 | 1.00 | 26.69 |
| ATOM | 560 CD | LYS | A | 286 | 16.105 | 60.262 | 38.032 | 1.00 | 28.58 |
| ATOM | 561 CE | LYS | A | 286 | 17.308 | 59.334 | 37.986 | 1.00 | 28.89 |
| ATOM | 562 NZ | LYS | A | 286 | 18.328 | 59.807 | 37.012 | 1.00 | 29.92 |
| ATOM | 563 C | LYS | A | 286 | 12.515 | 61.157 | 41.473 | 1.00 | 26.73 |
| ATOM | 564 O | LYS | A | 286 | 12.944 | 61.136 | 42.622 | 1.00 | 28.60 |
| ATOM | 565 N | SER | A | 287 | 12.543 | 61.980 | 41.133 | 1.00 | 25.80 |
| ATOM | 566 CA | SER | A | 287 | 10.969 | 62.865 | 42.158 | 1.00 | 26.18 |
| ATOM | 567 CB | SER | A | 287 | 11.627 | 64.249 | 42.056 | 1.00 | 26.60 |
| ATOM | 568 OG | SER | A | 287 | 11.272 | 64.767 | 40.796 | 1.00 | 28.18 |
| ATOM | 569 C | SER | A | 287 | 9.471 | 62.857 | 41.977 | 1.00 | 24.89 |
| ATOM | 570 O | SER | A | 287 | 8.996 | 62.358 | 40.947 | 1.00 | 25.47 |
| ATOM | 571 N | PRO | A | 288 | 8.739 | 63.268 | 42.989 | 1.00 | 26.04 |
| ATOM | 572 CD | PRO | A | 288 | 9.222 | 63.876 | 44.247 | 1.00 | 27.14 |
| ATOM | 573 CA | PRO | A | 288 | 7.294 | 61.276 | 42.938 | 1.00 | 26.70 |
| ATOM | 574 CB | PRO | A | 288 | 6.831 | 63.561 | 44.339 | 1.00 | 26.05 |
| ATOM | 575 CG | PRO | A | 288 | 8.010 | 63.972 | 45.128 | 1.00 | 27.69 |
| ATOM | 576 C | PRO | A | 288 | 6.826 | 64.313 | 41.928 | 1.00 | 27.00 |
| ATOM | 577 O | PRO | A | 288 | 7.522 | 65.301 | 41.666 | 1.00 | 27.28 |
| ATOM | 578 N | GLN | A | 289 | 5.681 | 64.051 | 41.341 | 1.00 | 25.80 |
| ATOM | 579 CA | GLN | A | 289 | 5.123 | 64.976 | 40.376 | 1.00 | 27.15 |
| ATOM | 580 CB | GLN | A | 289 | 4.021 | 64.214 | 39.628 | 1.00 | 27.78 |
| ATOM | 581 CG | GLN | A | 289 | 3.246 | 65.040 | 38.617 | 1.00 | 27.92 |
| ATOM | 582 CD | GLN | A | 289 | 4.207 | 65.636 | 37.616 | 1.00 | 28.41 |
| ATOM | 583 OE1 | GLN | A | 289 | 4.970 | 64.944 | 36.966 | 1.00 | 28.03 |
| ATOM | 584 NE2 | GLN | A | 289 | 4.179 | 66.966 | 37.505 | 1.00 | 32.04 |
| ATOM | 585 C | GLN | A | 289 | 4.553 | 66.194 | 41.093 | 1.00 | 27.84 |
| ATOM | 586 O | GLN | A | 289 | 3.693 | 66.017 | 41.943 | 1.00 | 27.12 |
| ATOM | 587 N | GLU | A | 290 | 4.962 | 67.414 | 40.766 | 1.00 | 30.72 |
| ATOM | 588 OE2 | GLU | A | 290 | 4.477 | 72.113 | 38.486 | 1.00 | 39.70 |
| ATOM | 589 OE1 | GLU | A | 290 | 4.067 | 72.564 | 39.857 | 1.00 | 40.48 |
| ATOM | 590 CD | GLU | A | 290 | 5.336 | 71.724 | 39.305 | 1.00 | 39.53 |
| ATOM | 591 CG | GLU | A | 290 | 5.461 | 70.253 | 39.660 | 1.00 | 37.94 |
| ATOM | 592 CB | GLU | A | 290 | 5.094 | 69.910 | 41.084 | 1.00 | 35.71 |
| ATOM | 593 CA | GLU | A | 290 | 4.384 | 68.595 | 41.401 | 1.00 | 33.44 |
| ATOM | 594 C | GLU | A | 290 | 2.912 | 68.679 | 40.978 | 1.00 | 32.66 |
| ATOM | 595 O | GLU | A | 290 | 2.615 | 68.487 | 39.807 | 1.00 | 32.60 |
| ATOM | 596 N | VAL | A | 291 | 2.027 | 68.929 | 41.928 | 1.00 | 32.52 |
| ATOM | 597 CA | VAL | A | 291 | 0.589 | 68.960 | 41.608 | 1.00 | 34.53 |
| ATOM | 598 CB | VAL | A | 291 | 0.016 | 67.667 | 42.214 | 1.00 | 34.68 |
| ATOM | 599 CG1 | VAL | A | 291 | −0.992 | 67.828 | 43.317 | 1.00 | 33.99 |
| ATOM | 600 CG2 | VAL | A | 291 | −0.509 | 66.742 | 41.114 | 1.00 | 33.97 |
| ATOM | 601 C | VAL | A | 291 | −0.040 | 70.265 | 42.070 | 1.00 | 36.93 |
| ATOM | 602 O | VAL | A | 291 | 0.296 | 70.786 | 43.141 | 1.00 | 35.77 |
| ATOM | 603 N | LYS | A | 292 | −0.879 | 70.860 | 41.231 | 1.00 | 38.91 |
| ATOM | 604 NZ | LYS | A | 292 | 0.250 | 74.239 | 36.361 | 1.00 | 47.09 |
| ATOM | 605 CE | LYS | A | 292 | −0.459 | 74.753 | 37.563 | 1.00 | 45.89 |
| ATOM | 606 CD | LYS | A | 292 | −1.298 | 73.665 | 38.215 | 1.00 | 45.49 |
| ATOM | 607 CG | LYS | A | 292 | −1.226 | 73.759 | 39.722 | 1.00 | 44.08 |
| ATOM | 608 CB | LYS | A | 292 | −2.197 | 72.809 | 40.397 | 1.00 | 42.31 |
| ATOM | 609 CA | LYS | A | 292 | −1.595 | 72.078 | 41.589 | 1.00 | 41.28 |

TABLE 1-continued

REMARK Created by MOLEMAN V. 961218/7.2.5 at Fri Sep 19 20:05:05 1997 for user carlos
REMARK Moleman FDS file

| CRYST1 | 61.387 | 126.278 | 81.273 | 90.00 | 107.42 | 90.00 | P 21 | 4 | |
|---|---|---|---|---|---|---|---|---|---|
| CRIGX1 | | 1.000000 | | 0.000000 | | | 0.000000 | | 0.00000 |
| CRIGX2 | | 0.000000 | | 1.000000 | | | 0.000000 | | 0.00000 |
| CRIGX3 | | 0.000000 | | 0.000000 | | | 1.000000 | | 0.00000 |
| SCALE1 | | 0.016290 | | 0.000000 | | | 0.005111 | | 0.00000 |
| SCALE2 | | 0.000000 | | 0.007919 | | | 0.000000 | | 0.00000 |
| SCALE3 | | 0.000000 | | 0.000000 | | | 0.012896 | | 0.00000 |

| | Atom Type | Residue | ! | # | X | Y | Z | OCC | B |
|---|---|---|---|---|---|---|---|---|---|
| ATOM | 610 C | LYS | A | 292 | −2.701 | 71.697 | 42.557 | 1.00 | 41.79 |
| ATOM | 611 O | LYS | A | 292 | −3.085 | 70.535 | 42.624 | 1.00 | 42.72 |
| ATOM | 612 N | PRO | A | 293 | −3.192 | 72.668 | 43.305 | 1.00 | 42.21 |
| ATOM | 613 CD | PRO | A | 293 | −2.802 | 74.096 | 43.247 | 1.00 | 42.59 |
| ATOM | 614 CA | PRO | A | 293 | −4.279 | 72.420 | 44.237 | 1.00 | 41.91 |
| ATOM | 615 CB | PRO | A | 293 | −4.605 | 73.784 | 44.806 | 1.00 | 41.79 |
| ATOM | 616 CG | PRO | A | 293 | −3.481 | 74.676 | 44.450 | 1.00 | 41.90 |
| ATOM | 617 C | PRO | A | 293 | −5.441 | 71.807 | 43.474 | 1.00 | 41.40 |
| ATOM | 618 O | PRO | A | 293 | −5.696 | 72.212 | 42.339 | 1.00 | 41.02 |
| ATOM | 619 N | GLY | A | 294 | −6.059 | 70.755 | 44.003 | 1.00 | 40.85 |
| ATOM | 620 CA | GLY | A | 294 | −7.176 | 70.133 | 43.332 | 1.00 | 41.30 |
| ATOM | 621 C | GLY | A | 294 | −6.832 | 69.033 | 42.332 | 1.00 | 40.98 |
| ATOM | 622 O | GLY | A | 294 | −7.688 | 68.185 | 42.061 | 1.00 | 41.17 |
| ATOM | 623 N | GLU | A | 295 | −5.636 | 69.051 | 41.753 | 1.00 | 39.55 |
| ATOM | 624 OE2 | GLU | A | 295 | −2.049 | 69.989 | 38.852 | 1.00 | 44.47 |
| ATOM | 625 OE1 | GLU | A | 295 | −3.356 | 71.223 | 37.568 | 1.00 | 44.87 |
| ATOM | 626 CD | GLU | A | 295 | −3.176 | 70.330 | 38.422 | 1.00 | 44.01 |
| ATOM | 627 CG | GLU | A | 295 | −4.422 | 69.647 | 38.946 | 2.00 | 42.26 |
| ATOM | 628 CB | GLU | A | 295 | −4.099 | 68.521 | 39.886 | 1.00 | 39.91 |
| ATOM | 629 CA | GLU | A | 295 | −5.214 | 68.044 | 40.813 | 1.00 | 38.60 |
| ATOM | 630 C | GLU | A | 295 | −4.641 | 66.825 | 41.552 | 1.00 | 36.59 |
| ATOM | 631 O | GLU | A | 295 | −4.281 | 66.871 | 42.720 | 1.00 | 36.85 |
| ATOM | 632 N | LYS | A | 296 | −4.418 | 65.777 | 40.773 | 1.00 | 33.95 |
| ATOM | 633 CA | LYS | A | 296 | −3.782 | 64.575 | 41.294 | 1.00 | 30.68 |
| ATOM | 634 CB | LYS | A | 296 | −4.755 | 63.656 | 41.996 | 1.00 | 31.56 |
| ATOM | 635 CG | LYS | A | 296 | −5.992 | 63.312 | 41.185 | 1.00 | 32.22 |
| ATOM | 636 CD | LYS | A | 296 | −7.149 | 62.924 | 42.075 | 1.00 | 32.13 |
| ATOM | 637 CE | LYS | A | 296 | −8.161 | 62.034 | 41.381 | 1.00 | 33.43 |
| ATOM | 638 NZ | LYS | A | 296 | −8.106 | 62.091 | 39.904 | 1.00 | 34.90 |
| ATOM | 639 C | LYS | A | 296 | −3.028 | 63.883 | 40.167 | 1.00 | 28.79 |
| ATOM | 640 O | LYS | A | 296 | −3.275 | 64.112 | 38.986 | 1.00 | 27.50 |
| ATOM | 641 N | HIS | A | 297 | −1.999 | 63.335 | 40.580 | 1.00 | 25.20 |
| ATOM | 642 CA | HIS | A | 297 | −1.216 | 62.396 | 39.584 | 1.00 | 20.71 |
| ATOM | 643 CB | HIS | A | 297 | −0.148 | 63.267 | 38.981 | 1.00 | 20.06 |
| ATOM | 644 CG | HIS | A | 297 | 0.824 | 62.612 | 38.054 | 1.00 | 18.56 |
| ATOM | 645 CD2 | HIS | A | 297 | 1.808 | 61.741 | 38.309 | 1.00 | 15.40 |
| ATOM | 646 ND1 | HIS | A | 297 | 0.863 | 62.878 | 36.701 | 1.00 | 18.13 |
| ATOM | 647 CE1 | HIS | A | 297 | 1.844 | 62.180 | 36.160 | 1.00 | 17.97 |
| ATOM | 648 NE2 | HIS | A | 297 | 2.416 | 61.463 | 37.105 | 1.00 | 19.72 |
| ATOM | 649 C | HIS | A | 297 | −0.730 | 61.151 | 40.292 | 1.00 | 19.15 |
| ATOM | 650 O | HIS | A | 297 | −0.477 | 61.256 | 41.493 | 1.00 | 18.54 |
| ATOM | 651 N | TYR | A | 298 | −0.557 | 60.030 | 39.580 | 1.00 | 18.21 |
| ATOM | 652 CA | TYR | A | 298 | −0.155 | 58.824 | 40.330 | 1.00 | 16.80 |
| ATOM | 653 CB | TYR | A | 298 | −0.193 | 57.594 | 39.437 | 1.00 | 16.24 |
| ATOM | 654 CG | TYR | A | 298 | 0.940 | 57.509 | 38.444 | 1.00 | 17.23 |
| ATOM | 655 CD1 | TYR | A | 298 | 2.077 | 56.755 | 38.742 | 1.00 | 15.56 |
| ATOM | 656 CE1 | TYR | A | 298 | 3.094 | 56.667 | 37.821 | 1.00 | 15.21 |
| ATOM | 657 CD2 | TYR | A | 298 | 0.881 | 53.384 | 37.236 | 1.00 | 16.74 |
| ATOM | 658 CE2 | TYR | A | 298 | 1.913 | 58.098 | 36.337 | 1.00 | 16.91 |
| ATOM | 659 CZ | TYR | A | 298 | 3.022 | 57.325 | 36.636 | 1.00 | 16.49 |
| ATOM | 660 OH | TYR | A | 298 | 4.046 | 57.260 | 35.719 | 1.00 | 18.10 |
| ATOM | 661 C | TYR | A | 298 | 1.185 | 58.981 | 41.029 | 1.00 | 16.63 |
| ATOM | 662 O | TYR | A | 298 | 1.351 | 58.330 | 42.073 | 1.00 | 16.70 |
| ATOM | 663 N | ASN | A | 299 | 2.112 | 59.766 | 40.523 | 1.00 | 16.99 |
| ATOM | 664 CA | ASN | A | 299 | 3.423 | 60.011 | 41.085 | 1.00 | 18.59 |
| ATOM | 665 CB | ASN | A | 299 | 4.463 | 60.166 | 39.965 | 1.00 | 18.92 |
| ATOM | 666 CG | ASN | A | 299 | 5.890 | 60.214 | 40.494 | 1.00 | 18.76 |
| ATOM | 667 OD1 | ASN | A | 299 | 6.205 | 59.456 | 41.412 | 1.00 | 18.23 |
| ATOM | 668 ND2 | ASN | A | 299 | 6.748 | 61.070 | 39.950 | 1.00 | 19.19 |
| ATOM | 669 C | ASN | A | 299 | 3.513 | 61.224 | 42.009 | 1.00 | 20.06 |
| ATOM | 670 O | ASN | A | 299 | 4.606 | 61.723 | 42.362 | 1.00 | 18.80 |
| ATOM | 671 N | MET | A | 300 | 2.395 | 61.732 | 42.509 | 1.00 | 20.80 |
| ATOM | 672 CA | MET | A | 300 | 2.449 | 62.886 | 43.417 | 1.00 | 22.77 |
| ATOM | 673 CB | MET | A | 300 | 1.115 | 63.568 | 43.608 | 1.00 | 23.16 |
| ATOM | 674 CG | MET | A | 300 | 0.029 | 62.931 | 44.436 | 1.00 | 25.10 |
| ATOM | 675 SD | MET | A | 300 | −1.590 | 63.723 | 44.020 | 1.00 | 28.00 |

TABLE 1-continued

REMARK Created by MOLEMAN V. 961218/7.2.5 at Fri Sep 19 20:05:05 1997 for user carlos
REMARK Moleman FDS file
CRYST1 61.387   126.278   81.273   90.00   107.42 90.00   P 21   4
CRIGX1        1.000000           0.000000           0.000000           0.00000
CRIGX2        0.000000           1.000000           0.000000           0.00000
CRIGX3        0.000000           0.000000           1.000000           0.00000
SCALE1        0.016290           0.000000           0.005111           0.00000
SCALE2        0.000000           0.007919           0.000000           0.00000
SCALE3        0.000000           0.000000           0.012896           0.00000

| | Atom Type | Residue | ! | # | X | Y | Z | OCC | B |
|---|---|---|---|---|---|---|---|---|---|
| ATOM | 676 CE | MET | A | 300 | −2.640 | 62.839 | 45.144 | 1.00 | 24.04 |
| ATOM | 677 C | MET | A | 300 | 3.012 | 62.458 | 44.767 | 1.00 | 21.89 |
| ATOM | 678 O | MET | A | 300 | 2.833 | 61.314 | 45.160 | 1.00 | 18.53 |
| ATOM | 679 N | ALA | A | 301 | 3.369 | 63.413 | 45.606 | 1.00 | 22.83 |
| ATOM | 680 CA | ALA | A | 301 | 3.872 | 63.134 | 46.926 | 1.00 | 23.87 |
| ATOM | 681 CB | ALA | A | 301 | 4.450 | 64.429 | 47.484 | 1.00 | 23.72 |
| ATOM | 682 C | ALA | A | 301 | 2.841 | 62.580 | 47.893 | 1.00 | 24.63 |
| ATOM | 683 O | ALA | A | 301 | 3.085 | 61.615 | 48.637 | 1.00 | 23.46 |
| ATOM | 684 N | LYS | A | 302 | 1.652 | 63.178 | 47.913 | 1.00 | 26.09 |
| ATOM | 685 CA | LYS | A | 302 | 0.645 | 62.719 | 48.859 | 1.00 | 26.00 |
| ATOM | 686 CB | LYS | A | 302 | −0.215 | 63.890 | 49.329 | 1.00 | 28.38 |
| ATOM | 687 CG | LYS | A | 302 | 0.554 | 65.188 | 49.528 | 1.00 | 29.29 |
| ATOM | 688 CD | LYS | A | 302 | 1.697 | 65.125 | 50.505 | 1.00 | 30.98 |
| ATOM | 689 CE | LYS | A | 302 | 2.522 | 66.407 | 50.512 | 1.00 | 32.65 |
| ATOM | 690 NZ | LYS | A | 302 | 2.617 | 67.085 | 49.191 | 1.00 | 33.62 |
| ATOM | 691 C | LYS | A | 302 | −0.198 | 61.580 | 48.291 | 1.00 | 25.55 |
| ATOM | 692 O | LYS | A | 302 | −0.295 | 61.399 | 47.087 | 1.00 | 24.72 |
| ATOM | 693 N | SER | A | 303 | −0.793 | 60.835 | 49.202 | 1.00 | 24.45 |
| ATOM | 694 CA | SER | A | 303 | −1.621 | 59.696 | 48.836 | 1.00 | 25.50 |
| ATOM | 695 CB | SER | A | 303 | −1.434 | 58.619 | 49.878 | 1.00 | 26.64 |
| ATOM | 696 OG | SER | A | 303 | −1.869 | 59.030 | 51.149 | 1.00 | 31.03 |
| ATOM | 697 C | SER | A | 303 | −3.052 | 60.182 | 48.666 | 1.00 | 25.87 |
| ATOM | 698 O | SER | A | 303 | −3.396 | 61.256 | 49.185 | 1.00 | 22.73 |
| ATOM | 699 N | TYR | A | 304 | −3.814 | 59.454 | 47.855 | 1.00 | 24.98 |
| ATOM | 700 CA | TYR | A | 304 | −5.181 | 59.862 | 47.550 | 1.00 | 24.27 |
| ATOM | 701 CB | TYR | A | 304 | −5.140 | 60.449 | 46.132 | 1.00 | 25.45 |
| ATOM | 702 CG | TYR | A | 304 | −6.466 | 61.015 | 45.686 | 1.00 | 28.35 |
| ATOM | 703 CD1 | TYR | A | 304 | −6.762 | 62.357 | 45.929 | 1.00 | 29.08 |
| ATOM | 704 CE1 | TYR | A | 304 | −7.978 | 62.891 | 45.552 | 1.00 | 29.59 |
| ATOM | 705 CD2 | TYR | A | 304 | −7.426 | 60.214 | 45.085 | 1.00 | 27.54 |
| ATOM | 706 CE2 | TYR | A | 304 | −8.630 | 60.754 | 44.702 | 1.00 | 29.33 |
| ATOM | 707 CZ | TYR | A | 304 | −8.893 | 62.094 | 44.944 | 1.00 | 29.27 |
| ATOM | 708 OH | TYR | A | 304 | −10.103 | 62.610 | 44.578 | 1.00 | 32.08 |
| ATOM | 709 C | TYR | A | 304 | −6.192 | 58.769 | 47.721 | 1.00 | 25.14 |
| ATOM | 710 O | TYR | A | 304 | −5.707 | 57.735 | 47.336 | 1.000 | 20.08 |
| ATOM | 711 N | PRO | A | 305 | −7.356 | 59.000 | 48.279 | 1.00 | 26.60 |
| ATOM | 712 CD | PRO | A | 305 | −8.386 | 58.001 | 48.459 | 1.00 | 25.22 |
| ATOM | 713 CA | PRO | A | 305 | −7.989 | 60.240 | 48.637 | 1.00 | 27.02 |
| ATOM | 714 CB | PRO | A | 305 | −9.492 | 60.083 | 48.491 | 1.00 | 25.75 |
| ATOM | 715 CG | PRO | A | 305 | −9.707 | 58.646 | 48.789 | 1.00 | 25.74 |
| ATOM | 716 C | PRO | A | 305 | −7.625 | 60.782 | 50.007 | 1.00 | 28.63 |
| ATOM | 717 O | PRO | A | 305 | −7.922 | 61.915 | 50.430 | 1.00 | 28.68 |
| ATOM | 718 N | ASN | A | 306 | −6.988 | 59.904 | 50.783 | 1.00 | 29.14 |
| ATOM | 719 CA | ASN | A | 306 | −6.713 | 60.273 | 52.173 | 1.00 | 30.26 |
| ATOM | 720 CB | ASN | A | 306 | −7.350 | 59.232 | 53.075 | 1.00 | 32.58 |
| ATOM | 721 CG | ASN | A | 306 | −8.766 | 58.861 | 52.676 | 1.00 | 35.48 |
| ATOM | 722 OD1 | ASN | A | 306 | −9.661 | 59.712 | 52.612 | 1.00 | 36.24 |
| ATOM | 723 ND2 | ASN | A | 306 | −8.992 | 57.588 | 52.368 | 1.00 | 36.01 |
| ATOM | 724 C | ASN | A | 306 | −5.229 | 60.477 | 52.375 | 1.00 | 29.94 |
| ATOM | 725 O | ASN | A | 306 | −4.444 | 59.536 | 52.439 | 1.00 | 28.29 |
| ATOM | 726 N | GLU | A | 307 | −4.819 | 61.724 | 52.507 | 1.00 | 29.94 |
| ATOM | 727 OE2 | GLU | A | 307 | −2.295 | 66.669 | 51.130 | 1.00 | 41.44 |
| ATOM | 728 OE1 | GLU | A | 307 | −2.711 | 66.223 | 53.238 | 1.00 | 41.35 |
| ATOM | 729 CD | GLU | A | 307 | −2.656 | 65.896 | 52.037 | 1.00 | 40.02 |
| ATOM | 730 CG | GLU | A | 307 | −3.034 | 64.464 | 51.678 | 1.00 | 38.20 |
| ATOM | 731 CB | GLU | A | 307 | −3.401 | 63.683 | 52.914 | 1.00 | 33.77 |
| ATOM | 732 CA | GLU | A | 307 | −3.461 | 62.152 | 52.717 | 1.00 | 32.32 |
| ATOM | 733 C | GLU | A | 307 | −2.770 | 61.594 | 53.949 | 1.00 | 30.24 |
| ATOM | 734 O | GLU | A | 307 | −1.542 | 61.522 | 53.870 | 1.00 | 30.44 |
| ATOM | 735 N | GLU | A | 308 | −3.513 | 61.273 | 54.984 | 1.00 | 29.39 |
| ATOM | 736 OE2 | GLU | A | 308 | −6.099 | 61.320 | 55.501 | 1.00 | 38.47 |
| ATOM | 737 OE1 | GLU | A | 308 | −7.129 | 59.531 | 56.089 | 1.00 | 37.95 |
| ATOM | 738 CD | GLU | A | 308 | −6.176 | 60.330 | 56.250 | 1.00 | 36.70 |
| ATOM | 739 CG | GLU | A | 308 | −5.168 | 60.057 | 57.322 | 1.00 | 35.39 |
| ATOM | 740 CB | GLU | A | 308 | −3.931 | 60.913 | 57.384 | 1.00 | 33.10 |
| ATOM | 741 CA | GLU | A | 308 | −2.950 | 60.795 | 56.224 | 1.00 | 29.98 |

TABLE 1-continued

REMARK Created by MOLEMAN V. 961218/7.2.5 at Fri Sep 19 20:05:05 1997 for user carlos
REMARK Moleman FDS file
CRYST1 61.387 126.278 81.273 90.00 107.42 90.00 P 21 4
CRIGX1     1.000000     0.000000     0.000000     0.00000
CRIGX2     0.000000     1.000000     0.000000     0.00000
CRIGX3     0.000000     0.000000     1.000000     0.00000
SCALE1     0.016290     0.000000     0.005111     0.00000
SCALE2     0.000000     0.007919     0.000000     0.00000
SCALE3     0.000000     0.000000     0.012896     0.00000

| | Atom Type | Residue | ! | # | X | Y | Z | OCC | B |
|---|---|---|---|---|---|---|---|---|---|
| ATOM | 742 C | GLU | A | 308 | −2.487 | 59.353 | 56.093 | 1.00 | 28.21 |
| ATOM | 743 O | GLU | A | 308 | −1.607 | 58.963 | 56.857 | 1.00 | 26.31 |
| ATOM | 744 N | LYS | A | 309 | −3.004 | 58.626 | 55.094 | 1.00 | 24.19 |
| ATOM | 745 CA | LYS | A | 309 | −2.648 | 57.216 | 55.015 | 1.00 | 24.20 |
| ATOM | 746 CB | LYS | A | 309 | −3.711 | 56.413 | 54.263 | 1.00 | 24.89 |
| ATOM | 747 CG | LYS | A | 309 | −5.098 | 56.344 | 54.884 | 1.00 | 27.73 |
| ATOM | 748 CD | LYS | A | 309 | −5.089 | 56.571 | 56.361 | 1.00 | 31.22 |
| ATOM | 749 CE | LYS | A | 309 | −6.317 | 56.792 | 57.162 | 1.00 | 32.52 |
| ATOM | 750 NZ | LYS | A | 309 | −6.638 | 55.694 | 58.107 | 1.00 | 34.53 |
| ATOM | 751 C | LYS | A | 309 | −1.285 | 57.012 | 54.387 | 1.00 | 21.98 |
| ATOM | 752 O | LYS | A | 309 | −0.832 | 57.851 | 53.636 | 1.00 | 22.27 |
| ATOM | 753 N | ASP | A | 310 | −0.675 | 55.855 | 54.593 | 1.00 | 20.75 |
| ATOM | 754 CA | ASP | A | 310 | 0.605 | 55.530 | 53.953 | 1.00 | 20.70 |
| ATOM | 755 CB | ASP | A | 310 | 1.130 | 54.173 | 54.501 | 1.00 | 20.15 |
| ATOM | 756 CG | ASP | A | 310 | 2.615 | 54.085 | 54.167 | 1.00 | 22.21 |
| ATOM | 757 OD1 | ASP | A | 310 | 3.335 | 54.893 | 54.831 | 1.00 | 24.55 |
| ATOM | 758 OD2 | ASP | A | 310 | 3.040 | 53.306 | 53.292 | 1.00 | 18.20 |
| ATOM | 759 C | ASP | A | 310 | 0.474 | 55.419 | 52.450 | 1.00 | 19.43 |
| ATOM | 760 O | ASP | A | 310 | 1.385 | 55.706 | 51.651 | 1.00 | 20.19 |
| ATOM | 761 N | ALA | A | 311 | −0.727 | 55.044 | 51.990 | 1.00 | 18.69 |
| ATOM | 762 CA | ALA | A | 311 | −0.947 | 54.834 | 50.572 | 1.00 | 17.44 |
| ATOM | 763 CB | ALA | A | 311 | −0.991 | 53.296 | 50.429 | 1.00 | 16.55 |
| ATOM | 764 C | ALA | A | 311 | −2.302 | 55.316 | 50.025 | 1.00 | 16.60 |
| ATOM | 765 O | ALA | A | 311 | −3.221 | 55.655 | 50.751 | 1.00 | 12.08 |
| ATOM | 766 N | TRP | A | 312 | −2.339 | 55.302 | 48.711 | 1.00 | 17.19 |
| ATOM | 767 CA | TRP | A | 312 | −3.555 | 55.615 | 47.963 | 1.00 | 15.85 |
| ATOM | 768 CB | TRP | A | 312 | −3.236 | 55.569 | 46.483 | 1.00 | 14.37 |
| ATOM | 769 CG | TRP | A | 312 | −2.713 | 56.757 | 45.760 | 1.00 | 16.10 |
| ATOM | 770 CD2 | TRP | A | 312 | −3.413 | 57.526 | 44.772 | 1.00 | 16.24 |
| ATOM | 771 CE2 | TRP | A | 312 | −2.554 | 58.554 | 44.342 | 1.00 | 17.46 |
| ATOM | 772 CE1 | TRP | A | 312 | −4.685 | 57.427 | 44.204 | 1.00 | 17.59 |
| ATOM | 773 CD1 | TRP | A | 312 | −1.492 | 57.360 | 45.884 | 1.00 | 15.52 |
| ATOM | 774 NE1 | TRP | A | 312 | −1.381 | 58.440 | 45.050 | 1.00 | 16.75 |
| ATOM | 775 CZ2 | TRP | A | 312 | −2.900 | 59.475 | 43.357 | 1.00 | 17.80 |
| ATOM | 776 CZ3 | TRP | A | 312 | −5.022 | 58.348 | 43.228 | 1.00 | 15.80 |
| ATOM | 777 CH2 | TRP | A | 312 | −4.154 | 59.345 | 42.828 | 1.00 | 17.23 |
| ATOM | 778 C | TRP | A | 312 | −4.562 | 54.502 | 41.204 | 1.00 | 16.18 |
| ATOM | 779 O | TRP | A | 312 | −4.185 | 53.393 | 48.559 | 1.00 | 14.62 |
| ATOM | 780 N | ASP | A | 313 | −5.841 | 54.750 | 47.906 | 1.00 | 17.14 |
| ATOM | 781 CA | ASP | A | 313 | −6.817 | 53.682 | 47.741 | 1.00 | 17.42 |
| ATOM | 782 CB | ASP | A | 313 | −8.170 | 54.298 | 47.343 | 1.00 | 19.70 |
| ATOM | 783 CG | ASP | A | 313 | −9.106 | 53.244 | 46.797 | 1.00 | 22.89 |
| ATOM | 784 OD1 | ASP | A | 313 | −9.073 | 52.935 | 45.598 | 1.00 | 24.60 |
| ATOM | 785 OD2 | ASP | A | 313 | −9.841 | 52.697 | 47.623 | 1.00 | 26.78 |
| ATOM | 786 C | ASP | A | 313 | −6.273 | 52.903 | 46.539 | 1.00 | 14.58 |
| ATOM | 787 O | ASP | A | 313 | −6.033 | 53.570 | 45.533 | 1.00 | 14.85 |
| ATOM | 788 N | VAL | A | 314 | −6.101 | 51.596 | 46.588 | 1.00 | 15.33 |
| ATOM | 789 CA | VAL | A | 314 | −5.434 | 50.915 | 45.475 | 1.00 | 14.25 |
| ATOM | 790 CB | VAL | A | 314 | −5.067 | 49.478 | 45.891 | 1.00 | 13.94 |
| ATOM | 791 CG1 | VAL | A | 314 | −6.266 | 48.578 | 46.107 | 1.00 | 12.58 |
| ATOM | 792 CG2 | VAL | A | 314 | −4.090 | 48.891 | 44.864 | 1.00 | 12.94 |
| ATOM | 793 C | VAL | A | 314 | −6.110 | 50.966 | 44.129 | 1.00 | 14.22 |
| ATOM | 794 O | VAL | A | 314 | −5.480 | 51.152 | 43.099 | 1.00 | 13.01 |
| ATOM | 795 N | LYS | A | 315 | −7.435 | 50.819 | 44.092 | 1.00 | 16.35 |
| ATOM | 796 NZ | LYS | A | 315 | −12.342 | 48.884 | 46.668 | 1.00 | 27.78 |
| ATOM | 797 CE | LYS | A | 315 | −11.908 | 48.279 | 45.365 | 1.00 | 26.99 |
| ATOM | 798 CD | LYS | A | 315 | −11.499 | 49.287 | 44.334 | 1.00 | 24.72 |
| ATOM | 799 CG | LYS | A | 315 | −10.084 | 43.278 | 43.775 | 1.00 | 21.52 |
| ATOM | 800 CB | LYS | A | 315 | −9.700 | 50.621 | 43.204 | 1.00 | 18.30 |
| ATOM | 801 CA | LYS | A | 315 | −8.223 | 50.882 | 42.870 | 1.00 | 17.01 |
| ATOM | 802 C | LYS | A | 315 | −8.111 | 52.273 | 42.255 | 1.00 | 15.42 |
| ATOM | 803 O | LYS | A | 315 | −7.967 | 52.432 | 41.065 | 1.00 | 14.82 |
| ATOM | 804 N | MET | A | 316 | −8.189 | 53.317 | 43.095 | 1.00 | 16.67 |
| ATOM | 805 CA | MET | A | 316 | −8.023 | 54.673 | 42.531 | 1.00 | 16.96 |
| ATOM | 806 CB | MET | A | 316 | −8.396 | 55.717 | 43.579 | 1.00 | 19.66 |
| ATOM | 807 CG | MET | A | 316 | −9.874 | 55.516 | 43.966 | 1.00 | 21.49 |

TABLE 1-continued

REMARK Created by MOLEMAN V. 961218/7.2.5 at Fri Sep 19 20:05:05 1997 for user carlos
REMARK Moleman FDS file CRYST1 61.387  126.278  81.273  90.00  107.42 90.00  P 21  4
CRIGX1         1.000000            0.000000            0.000000        0.00000
CRIGX2         0.000000            1.000000            0.000000        0.00000
CRIGX3         0.000000            0.000000            1.000000        0.00000
SCALE1         0.016290            0.000000            0.005111        0.00000
SCALE2         0.000000            0.007919            0.000000        0.00000
SCALE3         0.000000            0.000000            0.012896        0.00000

| | Atom Type | Residue | ! | # | X | Y | Z | OCC | B |
|---|---|---|---|---|---|---|---|---|---|
| ATOM | 808 SD | MET | A | 316 | −10.303 | 56.858 | 45.216 | 1.00 | 25.95 |
| ATOM | 809 CE | MET | A | 316 | −11.921 | 56.212 | 45.655 | 1.00 | 23.70 |
| ATOM | 810 C | MET | A | 316 | −6.624 | 54.927 | 41.996 | 1.00 | 16.13 |
| ATOM | 811 O | MET | A | 316 | −6.463 | 55.672 | 41.038 | 1.00 | 16.38 |
| ATOM | 812 N | LEU | A | 317 | −5.583 | 54.315 | 42.552 | 1.00 | 15.29 |
| ATOM | 813 CA | LEU | A | 317 | −4.218 | 54.490 | 42.078 | 1.00 | 13.26 |
| ATOM | 814 CB | LEU | A | 317 | −3.200 | 53.915 | 43.097 | 1.00 | 11.74 |
| ATOM | 815 CG | LEU | A | 317 | −1.733 | 54.036 | 42.672 | 1.00 | 12.04 |
| ATOM | 816 CD1 | LEU | A | 317 | −1.323 | 55.505 | 42.512 | 1.00 | 10.99 |
| ATOM | 817 CD2 | LEU | A | 317 | −0.861 | 53.326 | 43.698 | 1.00 | 11.54 |
| ATOM | 818 C | LEU | A | 317 | −4.079 | 53.785 | 40.755 | 1.00 | 12.38 |
| ATOM | 819 O | LEU | A | 317 | −3.526 | 54.334 | 39.819 | 1.00 | 14.48 |
| ATOM | 820 N | LEU | A | 318 | −4.637 | 52.580 | 40.616 | 1.00 | 12.87 |
| ATOM | 821 CA | LEU | A | 318 | −4.561 | 51.890 | 39.326 | 1.00 | 12.84 |
| ATOM | 822 CB | LEU | A | 318 | −5.112 | 50.457 | 39.453 | 1.00 | 12.79 |
| ATOM | 823 CG | LEU | A | 318 | −4.966 | 49.629 | 38.170 | 1.00 | 14.82 |
| ATOM | 824 CD1 | LEU | A | 318 | −3.531 | 49.542 | 37.700 | 1.00 | 15.86 |
| ATOM | 825 CD2 | LEU | A | 318 | −5.558 | 48.241 | 38.355 | 1.00 | 14.73 |
| ATOM | 826 C | LEU | A | 318 | −5.230 | 52.673 | 38.218 | 1.00 | 12.07 |
| ATOM | 827 O | LEU | A | 318 | −4.780 | 52.829 | 37.099 | 1.00 | 12.74 |
| ATOM | 828 N | GLU | A | 319 | −6.420 | 53.193 | 38.511 | 1.00 | 15.24 |
| ATOM | 829 OE2 | GLU | A | 319 | −11.483 | 52.210 | 39.220 | 1.00 | 28.26 |
| ATOM | 830 OE1 | GLU | A | 319 | −10.797 | 54.093 | 40.042 | 1.00 | 29.42 |
| ATOM | 831 CD | GLU | A | 319 | −10.674 | 53.181 | 39.153 | 1.00 | 27.45 |
| ATOM | 832 CG | GLU | A | 319 | −9.561 | 53.233 | 38.177 | 1.00 | 24.55 |
| ATOM | 833 CB | GLU | A | 319 | −8.553 | 54.375 | 38.270 | 1.00 | 18.18 |
| ATOM | 834 CA | GLU | A | 319 | −7.199 | 54.025 | 37.614 | 1.00 | 15.25 |
| ATOM | 835 C | GLU | A | 319 | −6.421 | 55.288 | 37.289 | 1.00 | 14.06 |
| ATOM | 836 O | GLU | A | 319 | −6.317 | 55.697 | 36.141 | 1.00 | 13.57 |
| ATOM | 837 N | GLN | A | 320 | −5.879 | 55.947 | 38.303 | 1.00 | 14.48 |
| ATOM | 838 CA | GLN | A | 320 | −5.086 | 57.164 | 38.073 | 1.00 | 15.95 |
| ATOM | 839 CB | GLN | A | 320 | −4.631 | 57.772 | 39.413 | 1.00 | 17.37 |
| ATOM | 840 CG | GLN | A | 320 | −3.969 | 59.147 | 39.262 | 1.00 | 20.30 |
| ATOM | 841 CD | GLN | A | 320 | −4.917 | 60.189 | 38.681 | 1.00 | 20.82 |
| ATOM | 842 OE1 | GLN | A | 320 | −6.069 | 60.198 | 39.101 | 1.00 | 22.55 |
| ATOM | 843 NE2 | GLN | A | 320 | −4.480 | 61.016 | 37.768 | 1.00 | 20.50 |
| ATOM | 844 C | GLN | A | 320 | −3.896 | 56.849 | 37.206 | 1.00 | 15.14 |
| ATOM | 845 O | GLN | A | 320 | −3.545 | 57.572 | 36.274 | 1.00 | 16.35 |
| ATOM | 846 N | PHE | A | 321 | −3.178 | 55.751 | 37.535 | 1.00 | 14.19 |
| ATOM | 847 CA | PHE | A | 321 | −1.997 | 55.416 | 36.728 | 1.00 | 13.62 |
| ATOM | 848 CB | PHE | A | 321 | −1.389 | 54.100 | 37.277 | 1.00 | 14.84 |
| ATOM | 849 CG | PHE | A | 321 | −0.286 | 53.531 | 36.462 | 1.00 | 14.25 |
| ATOM | 850 CD1 | PHE | A | 321 | 0.874 | 54.232 | 36.256 | 1.00 | 16.53 |
| ATOM | 851 CD2 | PHE | A | 321 | −0.407 | 52.275 | 35.889 | 1.00 | 15.71 |
| ATOM | 852 C∊1 | PHE | A | 321 | 1.915 | 53.714 | 35.499 | 1.00 | 16.96 |
| ATOM | 853 C∊2 | PHE | A | 321 | 0.594 | 51.737 | 35.109 | 1.00 | 16.98 |
| ATOM | 854 CZ | PHE | A | 321 | 1.760 | 52.464 | 34.920 | 1.00 | 19.64 |
| ATOM | 855 C | PHE | A | 321 | −2.367 | 55.265 | 35.284 | 1.00 | 15.37 |
| ATOM | 856 O | PHE | A | 321 | −1.743 | 55.838 | 34.391 | 1.00 | 17.95 |
| ATOM | 857 N | SER | A | 322 | −3.440 | 54.502 | 35.011 | 1.00 | 15.65 |
| ATOM | 858 CA | SER | A | 322 | −3.862 | 54.261 | 33.650 | 1.00 | 16.47 |
| ATOM | 859 CB | SER | A | 322 | −5.052 | 53.312 | 33.545 | 1.00 | 17.62 |
| ATOM | 860 CG | SER | A | 322 | −4.956 | 52.111 | 34.281 | 1.00 | 21.90 |
| ATOM | 861 C | SER | A | 322 | −4.219 | 55.608 | 32.980 | 1.00 | 15.02 |
| ATOM | 862 O | SER | A | 322 | −3.836 | 55.773 | 31.839 | 1.00 | 15.73 |
| ATOM | 863 N | PHE | A | 323 | −4.855 | 56.499 | 33.694 | 1.00 | 15.76 |
| ATOM | 864 CA | PHE | A | 323 | −5.163 | 57.831 | 33.153 | 1.00 | 17.15 |
| ATOM | 865 CB | PHE | A | 323 | −5.953 | 58.697 | 34.136 | 1.00 | 18.22 |
| ATOM | 866 CG | PHE | A | 323 | −6.374 | 60.050 | 33.604 | 1.00 | 20.68 |
| ATOM | 867 CD1 | PHE | A | 323 | −5.660 | 61.195 | 33.861 | 1.00 | 21.45 |
| ATOM | 868 CD2 | PHE | A | 323 | −7.524 | 60.161 | 32.852 | 1.00 | 22.31 |
| ATOM | 869 CE1 | PHE | A | 323 | −6.032 | 62.425 | 33.329 | 1.00 | 22.60 |
| ATOM | 870 CE2 | PHE | A | 323 | −7.945 | 61.384 | 32.325 | 1.00 | 24.15 |
| ATOM | 871 CZ | PHE | A | 323 | −7.175 | 62.502 | 32.558 | 1.00 | 23.26 |
| ATOM | 872 C | PHE | A | 323 | −3.897 | 58.570 | 32.756 | 1.00 | 18.05 |
| ATOM | 873 O | PHE | A | 323 | −3.807 | 59.053 | 31.648 | 1.00 | 15.95 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | | Atom Type | Residue | ! | # | X | Y | Z | OCC | B |
|---|---|---|---|---|---|---|---|---|---|---|
| ATOM | 874 | N | ASP | A | 324 | −2.913 | 58.698 | 33.662 | 1.00 | 19.20 |
| ATOM | 875 | CA | ASP | A | 324 | −1.748 | 59.521 | 33.405 | 1.00 | 20.57 |
| ATOM | 876 | CB | ASP | A | 324 | −0.994 | 59.740 | 34.742 | 1.00 | 23.05 |
| ATOM | 877 | CG | ASP | A | 324 | −1.773 | 60.624 | 35.687 | 1.00 | 23.08 |
| ATOM | 878 | OD1 | ASP | A | 324 | −1.894 | 60.419 | 36.896 | 1.00 | 22.69 |
| ATOM | 879 | OD2 | ASP | A | 324 | −2.335 | 61.620 | 35.188 | 1.00 | 26.34 |
| ATOM | 880 | C | ASP | A | 324 | −0.746 | 58.999 | 32.402 | 1.00 | 21.82 |
| ATOM | 881 | O | ASP | A | 324 | −0.058 | 59.793 | 31.764 | 1.00 | 21.73 |
| ATOM | 882 | N | ILE | A | 325 | −0.672 | 57.679 | 32.240 | 1.00 | 21.33 |
| ATOM | 883 | CA | ILE | A | 325 | 0.264 | 57.038 | 31.339 | 1.00 | 22.61 |
| ATOM | 884 | CB | ILE | A | 325 | 0.922 | 55.889 | 32.161 | 1.00 | 25.69 |
| ATOM | 885 | CG2 | ILE | A | 325 | 0.154 | 54.579 | 32.043 | 1.00 | 24.65 |
| ATOM | 886 | CG1 | ILE | A | 325 | 2.370 | 55.730 | 31.765 | 1.00 | 26.90 |
| ATOM | 887 | CD1 | ILE | A | 325 | 3.369 | 56.465 | 32.631 | 1.00 | 27.55 |
| ATOM | 888 | C | ILE | A | 325 | −0.394 | 56.551 | 30.073 | 1.00 | 22.34 |
| ATOM | 889 | O | ILE | A | 325 | 0.238 | 55.950 | 29.209 | 1.00 | 19.22 |
| ATOM | 890 | N | ALA | A | 326 | −1.663 | 56.970 | 23.849 | 1.00 | 21.30 |
| ATOM | 891 | CA | ALA | A | 326 | −2.412 | 56.538 | 28.677 | 1.00 | 21.14 |
| ATOM | 892 | CB | ALA | A | 326 | −3.743 | 57.301 | 28.568 | 1.00 | 20.96 |
| ATOM | 893 | C | ALA | A | 326 | −1.701 | 56.616 | 27.350 | 1.00 | 20.02 |
| ATOM | 894 | O | ALA | A | 326 | −1.716 | 55.660 | 26.557 | 1.00 | 18.13 |
| ATOM | 895 | N | GLU | A | 327 | −1.087 | 57.750 | 27.055 | 1.00 | 21.17 |
| ATOM | 896 | OE2 | GLU | A | 327 | 1.606 | 59.498 | 22.827 | 1.00 | 38.00 |
| ATOM | 897 | OE1 | GLU | A | 327 | −0.468 | 59.073 | 22.310 | 1.00 | 37.16 |
| ATOM | 898 | CD | GLU | A | 327 | 0.389 | 59.482 | 23.114 | 1.00 | 35.40 |
| ATOM | 889 | CG | GLU | A | 327 | −0.062 | 59.993 | 24.456 | 1.00 | 33.57 |
| ATOM | 900 | CB | GLU | A | 327 | 0.333 | 59.223 | 25.685 | 1.00 | 26.72 |
| ATOM | 901 | CA | GLU | A | 327 | −0.310 | 57.845 | 25.805 | 1.00 | 23.82 |
| ATOM | 902 | C | GLU | A | 327 | 0.748 | 56.760 | 25.705 | 1.00 | 20.97 |
| ATOM | 903 | O | GLU | A | 327 | 0.932 | 56.156 | 24.626 | 1.00 | 20.68 |
| ATOM | 904 | N | GLU | A | 328 | 1.536 | 56.501 | 26.758 | 1.00 | 20.00 |
| ATOM | 905 | OE2 | GLU | A | 328 | 6.485 | 57.857 | 28.558 | 1.00 | 20.00 |
| ATOM | 906 | OE1 | GLU | A | 328 | 5.550 | 56.151 | 29.650 | 1.00 | 20.00 |
| ATOM | 907 | CD | GLU | A | 328 | 5.561 | 56.965 | 28.651 | 1.00 | 20.00 |
| ATOM | 908 | CG | GLU | A | 328 | 4.474 | 56.875 | 27.579 | 1.00 | 20.00 |
| ATOM | 909 | CB | GLU | A | 328 | 3.625 | 55.608 | 27.694 | 1.00 | 20.00 |
| ATOM | 910 | CA | GLU | A | 328 | 2.584 | 55.483 | 26.582 | 1.00 | 20.00 |
| ATOM | 911 | C | GLU | A | 328 | 1.966 | 54.088 | 26.663 | 1.00 | 20.00 |
| ATOM | 912 | O | GLU | A | 328 | 2.420 | 53.176 | 25.932 | 1.00 | 20.00 |
| ATOM | 913 | N | ALA | A | 329 | 0.930 | 53.900 | 27.438 | 1.00 | 19.57 |
| ATOM | 914 | CA | ALA | A | 329 | 0.280 | 52.586 | 27.501 | 1.00 | 21.09 |
| ATOM | 915 | CB | ALA | A | 329 | −0.828 | 52.628 | 28.545 | 1.00 | 20.52 |
| ATOM | 916 | C | ALA | A | 329 | −0.292 | 52.148 | 26.167 | 1.00 | 21.74 |
| ATOM | 917 | O | ALA | A | 329 | −0.460 | 50.963 | 25.860 | 1.00 | 22.92 |
| ATOM | 918 | N | SER | A | 330 | −0.593 | 53.077 | 25.263 | 1.00 | 22.47 |
| ATOM | 919 | CA | SER | A | 330 | −1.185 | 52.807 | 23.972 | 1.00 | 23.55 |
| ATOM | 920 | CB | SER | A | 330 | −1.669 | 54.151 | 23.397 | 1.00 | 23.31 |
| ATOM | 921 | OG | SER | A | 330 | −0.614 | 54.856 | 22.781 | 1.00 | 25.74 |
| ATOM | 922 | C | SER | A | 330 | −0.209 | 52.129 | 23.038 | 1.00 | 23.79 |
| ATOM | 923 | O | SER | A | 330 | −0.545 | 51.533 | 22.032 | 1.00 | 23.93 |
| ATOM | 924 | N | LYS | A | 331 | 1.073 | 52.141 | 23.385 | 1.00 | 20.00 |
| ATOM | 925 | NZ | LYS | A | 331 | 4.948 | 57.241 | 21.295 | 1.00 | 20.00 |
| ATOM | 926 | CE | LYS | A | 331 | 3.827 | 56.290 | 21.276 | 1.00 | 20.00 |
| ATOM | 927 | CD | LYS | A | 331 | 4.162 | 54.958 | 21.950 | 1.00 | 20.00 |
| ATOM | 928 | CG | LYS | A | 331 | 2.995 | 53.972 | 21.928 | 1.00 | 20.00 |
| ATOM | 929 | CB | LYS | A | 331 | 3.327 | 52.639 | 22.588 | 1.00 | 20.00 |
| ATOM | 930 | CA | LYS | A | 331 | 2.147 | 51.613 | 22.574 | 1.00 | 20.00 |
| ATOM | 933 | C | LYS | A | 331 | 2.659 | 50.261 | 22.982 | 1.00 | 20.00 |
| ATOM | 932 | O | LYS | A | 331 | 3.484 | 49.683 | 22.278 | 1.00 | 20.00 |
| ATOM | 933 | N | VAL | A | 332 | 2.207 | 49.748 | 24.112 | 1.00 | 21.24 |
| ATOM | 934 | CA | VAL | A | 332 | 2.660 | 48.458 | 24.592 | 1.00 | 19.62 |
| ATOM | 935 | CB | VAL | A | 332 | 3.467 | 48.639 | 25.296 | 1.00 | 20.18 |
| ATOM | 936 | CG1 | VAL | A | 332 | 4.816 | 49.290 | 25.660 | 1.00 | 19.67 |
| ATOM | 937 | CG2 | VAL | A | 332 | 2.651 | 49.433 | 26.897 | 1.00 | 18.82 |
| ATOM | 938 | C | VAL | A | 332 | 1.495 | 47.533 | 24.905 | 1.00 | 18.19 |
| ATOM | 939 | O | VAL | A | 332 | 0.344 | 47.965 | 24.964 | 1.00 | 18.61 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 940 N | CYS | A | 333 | 1.816 | 46.274 | 25.098 | 1.00 | 16.72 |
| ATOM | 941 CA | CYS | A | 333 | 0.869 | 45.245 | 25.475 | 1.00 | 18.08 |
| ATOM | 942 CB | CYS | A | 333 | 1.522 | 43.872 | 25.365 | 1.00 | 20.13 |
| ATOM | 943 SG | CYS | A | 333 | 0.694 | 42.448 | 26.048 | 1.00 | 23.29 |
| ATOM | 944 C | CYS | A | 333 | 0.346 | 45.494 | 26.878 | 1.00 | 16.83 |
| ATOM | 945 O | CYS | A | 333 | −0.855 | 45.347 | 27.075 | 1.00 | 15.63 |
| ATOM | 946 N | LEU | A | 334 | 1.226 | 45.820 | 27.841 | 1.00 | 12.87 |
| ATOM | 947 CA | LEU | A | 334 | 0.838 | 46.094 | 29.187 | 1.00 | 12.88 |
| ATOM | 948 CB | LEU | A | 334 | 0.857 | 44.925 | 30.157 | 1.00 | 13.67 |
| ATOM | 949 CG | LEU | A | 334 | 0.004 | 43.686 | 29.867 | 1.00 | 12.92 |
| ATOM | 950 CD1 | LEU | A | 334 | 0.432 | 42.513 | 30.699 | 1.00 | 9.29 |
| ATOM | 951 CD2 | LEU | A | 334 | −1.465 | 44.030 | 30.158 | 1.00 | 10.80 |
| ATOM | 952 C | LEU | A | 334 | 1.788 | 47.151 | 29.816 | 1.00 | 14.90 |
| ATOM | 953 O | LEU | A | 334 | 2.929 | 47.313 | 29.428 | 1.00 | 13.88 |
| ATOM | 954 N | ALA | A | 335 | 1.203 | 47.856 | 30.778 | 1.00 | 14.03 |
| ATOM | 955 CA | ALA | A | 335 | 1.920 | 48.854 | 31.544 | 1.00 | 14.38 |
| ATOM | 956 CB | ALA | A | 335 | 1.292 | 50.235 | 31.381 | 1.00 | 15.95 |
| ATOM | 957 C | ALA | A | 335 | 1.859 | 48.404 | 32.991 | 1.00 | 13.27 |
| ATOM | 958 O | ALA | A | 335 | 0.794 | 48.020 | 33.435 | 1.00 | 14.32 |
| ATOM | 959 N | HIS | A | 336 | 2.936 | 48.458 | 33.750 | 1.00 | 12.02 |
| ATOM | 960 CA | HIS | A | 336 | 2.886 | 43.039 | 35.141 | 1.00 | 10.67 |
| ATOM | 961 CB | HIS | A | 336 | 3.543 | 46.555 | 35.252 | 1.00 | 9.55 |
| ATOM | 962 CG | HIS | A | 336 | 3.104 | 45.503 | 36.449 | 1.00 | 12.03 |
| ATOM | 963 CD2 | HIS | A | 336 | 2.026 | 45.099 | 36.601 | 1.00 | 9.22 |
| ATOM | 964 ND1 | HIS | A | 336 | 3.730 | 45.915 | 37.686 | 1.00 | 11.53 |
| ATOM | 965 CE1 | HIS | A | 336 | 3.048 | 45.186 | 38.533 | 1.00 | 8.45 |
| ATOM | 966 NE2 | HIS | A | 336 | 1.995 | 44.711 | 37.891 | 1.00 | 12.17 |
| ATOM | 967 C | HIS | A | 336 | 3.596 | 43.039 | 36.001 | 1.00 | 13.40 |
| ATOM | 968 O | HIS | A | 336 | 4.669 | 49.576 | 35.641 | 1.00 | 13.52 |
| ATOM | 969 N | LEU | A | 337 | 2.987 | 49.473 | 37.104 | 1.00 | 12.61 |
| ATOM | 970 CA | LEU | A | 337 | 3.514 | 50.440 | 38.026 | 1.00 | 12.83 |
| ATOM | 971 CB | LEU | A | 337 | 2.357 | 51.336 | 38.563 | 1.00 | 13.25 |
| ATOM | 972 CG | LEU | A | 337 | 2.688 | 52.163 | 33.816 | 1.00 | 14.22 |
| ATOM | 973 CD1 | LEU | A | 337 | 3.886 | 53.054 | 39.540 | 1.00 | 14.34 |
| ATOM | 974 CD2 | LEU | A | 337 | 1.439 | 53.027 | 40.232 | 1.00 | 12.48 |
| ATOM | 975 C | LEU | A | 337 | 4.137 | 49.730 | 39.243 | 1.00 | 11.76 |
| ATOM | 976 O | LEU | A | 337 | 3.486 | 48.887 | 39.833 | 1.00 | 10.29 |
| ATOM | 977 N | PHE | A | 338 | 5.396 | 50.012 | 39.548 | 1.00 | 11.12 |
| ATOM | 978 CA | PHE | A | 338 | 6.001 | 49.502 | 40.775 | 1.00 | 9.77 |
| ATOM | 979 CB | PHE | A | 338 | 7.378 | 48.877 | 40.584 | 1.00 | 10.95 |
| ATOM | 980 CG | PHE | A | 338 | 7.336 | 47.661 | 39.688 | 1.00 | 10.01 |
| ATOM | 981 CD1 | PHE | A | 338 | 7.341 | 47.745 | 38.336 | 1.00 | 6.77 |
| ATOM | 982 CD2 | PHE | A | 338 | 7.347 | 46.392 | 40.263 | 1.00 | 10.50 |
| ATOM | 983 CE1 | PHE | A | 338 | 7.261 | 46.629 | 37.530 | 1.00 | 8.39 |
| ATOM | 984 CE2 | PHE | A | 338 | 7.260 | 45.254 | 39.504 | 1.00 | 7.33 |
| ATOM | 985 CZ | PHE | A | 338 | 7.257 | 45.387 | 38.135 | 1.00 | 9.45 |
| ATOM | 986 C | PHE | A | 338 | 6.093 | 50.673 | 41.742 | 1.00 | 10.02 |
| ATOM | 987 O | PHE | A | 338 | 6.621 | 51.737 | 41.430 | 1.00 | 11.99 |
| ATOM | 988 N | THR | A | 339 | 5.501 | 50.493 | 42.897 | 1.00 | 9.73 |
| ATOM | 989 CA | THR | A | 339 | 5.455 | 51.468 | 43.940 | 1.00 | 12.72 |
| ATOM | 990 CB | THR | A | 339 | 4.053 | 52.092 | 44.003 | 1.00 | 15.30 |
| ATOM | 991 OG1 | THR | A | 339 | 4.060 | 53.246 | 44.828 | 1.00 | 16.97 |
| ATOM | 992 CG2 | THR | A | 339 | 3.048 | 51.044 | 44.495 | 1.00 | 15.12 |
| ATOM | 993 C | THR | A | 339 | 5.886 | 50.830 | 45.261 | 1.00 | 12.86 |
| ATOM | 994 O | THR | A | 339 | 6.169 | 49.638 | 45.386 | 1.00 | 12.05 |
| ATOM | 995 N | TYR | A | 340 | 5.954 | 51.663 | 46.268 | 1.00 | 11.17 |
| ATOM | 996 CA | TYR | A | 340 | 6.323 | 51.315 | 47.616 | 1.00 | 11.82 |
| ATOM | 997 CB | TYR | A | 340 | 7.823 | 51.632 | 47.844 | 1.00 | 10.81 |
| ATOM | 998 CG | TYR | A | 340 | 8.342 | 51.050 | 49.121 | 1.00 | 11.94 |
| ATOM | 999 CD1 | TYR | A | 340 | 8.766 | 49.717 | 49.157 | 1.00 | 13.34 |
| ATOM | 1000 CE1 | TYR | A | 340 | 9.228 | 49.144 | 50.342 | 1.00 | 13.22 |
| ATOM | 1001 CD2 | TYR | A | 340 | 8.375 | 51.795 | 50.286 | 1.00 | 11.57 |
| ATOM | 1002 CE2 | TYR | A | 340 | 8.862 | 51.239 | 51.481 | 1.00 | 13.34 |
| ATOM | 1003 CZ | TYR | A | 340 | 9.294 | 49.929 | 51.474 | 1.00 | 12.53 |
| ATOM | 1004 OH | TYR | A | 340 | 9.708 | 49.349 | 52.630 | 1.00 | 13.01 |
| ATOM | 1005 C | TYR | A | 340 | 5.422 | 52.066 | 48.560 | 1.00 | 12.56 |

TABLE 1-continued

REMARK Created by MOLEMAN V. 961218/7.2.5 at Fri Sep 19 20:05:05 1997 for user carlos
REMARK Moleman FDS file
CRYST1 61.387  126.278  81.273  90.00  107.42 90.00  P 21  4
CRIGX1       1.000000           0.000000           0.000000        0.00000
CRIGX2       0.000000           1.000000           0.000000        0.00000
CRIGX3       0.000000           0.000000           1.000000        0.00000
SCALE1       0.016290           0.000000           0.005111        0.00000
SCALE2       0.000000           0.007919           0.000000        0.00000
SCALE3       0.000000           0.000000           0.012896        0.00000

| | Atom Type | Residue | ! | # | X | Y | Z | OCC | B |
|---|---|---|---|---|---|---|---|---|---|
| ATOM | 1006 O | TYR | A | 340 | 5.784 | 53.138 | 49.086 | 1.00 | 13.24 |
| ATOM | 1007 N | GLN | A | 341 | 4.248 | 51.479 | 48.801 | 1.00 | 12.63 |
| ATOM | 1008 CA | GLN | A | 341 | 3.279 | 52.124 | 49.697 | 1.00 | 12.73 |
| ATOM | 1009 CB | GLN | A | 341 | 2.457 | 53.199 | 48.996 | 1.00 | 15.96 |
| ATOM | 1010 CG | GLN | A | 341 | 1.630 | 52.745 | 47.790 | 1.00 | 12.86 |
| ATOM | 1011 CD | GLN | A | 341 | 1.063 | 53.915 | 47.015 | 1.00 | 14.37 |
| ATOM | 1012 OE1 | GLN | A | 341 | 0.019 | 54.455 | 47.412 | 1.00 | 14.26 |
| ATOM | 1013 NE2 | GLN | A | 341 | 1.690 | 54.336 | 45.913 | 1.00 | 12.87 |
| ATOM | 1014 C | GLN | A | 341 | 2.409 | 51.026 | 50.281 | 1.00 | 13.05 |
| ATOM | 1015 O | GLN | A | 341 | 2.135 | 50.001 | 49.651 | 1.00 | 12.36 |
| ATOM | 1016 N | ASP | A | 342 | 2.036 | 51.214 | 51.518 | 1.00 | 11.62 |
| ATOM | 1017 CA | ASP | A | 342 | 1.313 | 50.221 | 52.293 | 1.00 | 12.36 |
| ATOM | 1018 CB | ASP | A | 342 | 1.766 | 50.350 | 53.748 | 1.00 | 11.58 |
| ATOM | 1019 CG | ASP | A | 342 | 1.603 | 49.084 | 54.533 | 1.00 | 14.83 |
| ATOM | 1020 OD1 | ASP | A | 342 | 1.136 | 48.053 | 53.979 | 1.00 | 12.25 |
| ATOM | 1021 OD2 | ASP | A | 342 | 1.976 | 49.034 | 55.734 | 1.00 | 16.16 |
| ATOM | 1022 C | ASP | A | 342 | −0.202 | 50.344 | 52.159 | 1.00 | 13.76 |
| ATOM | 1023 O | ASP | A | 342 | −0.850 | 50.940 | 53.016 | 1.00 | 10.06 |
| ATOM | 1024 N | PHE | A | 343 | −0.705 | 49.804 | 51.047 | 1.00 | 12.77 |
| ATOM | 1025 CA | PHE | A | 343 | −2.123 | 49.686 | 50.828 | 1.00 | 13.67 |
| ATOM | 1026 CB | PHE | A | 343 | −2.407 | 48.846 | 49.572 | 1.00 | 11.23 |
| ATOM | 1027 CG | PHE | A | 343 | −1.813 | 49.447 | 48.336 | 1.00 | 13.10 |
| ATOM | 1028 CD1 | PHE | A | 343 | −2.070 | 50.761 | 47.978 | 1.00 | 11.42 |
| ATOM | 1029 CD2 | PHE | A | 343 | −0.968 | 48.703 | 47.519 | 1.00 | 11.91 |
| ATOM | 1030 CE1 | PHE | A | 343 | −1.494 | 51.298 | 46.845 | 1.00 | 11.83 |
| ATOM | 1031 CE2 | PHE | A | 343 | −0.431 | 49.235 | 46.395 | 1.00 | 13.17 |
| ATOM | 1032 CZ | PHE | A | 343 | −0.693 | 50.547 | 46.011 | 1.00 | 11.97 |
| ATOM | 1033 C | PHE | A | 343 | −2.827 | 49.073 | 52.018 | 1.00 | 13.82 |
| ATOM | 1034 O | PHE | A | 343 | −2.411 | 48.111 | 52.663 | 1.00 | 11.97 |
| ATOM | 1035 N | ASP | A | 344 | −3.976 | 49.646 | 52.364 | 1.00 | 14.70 |
| ATOM | 1036 CA | ASP | A | 344 | −4.734 | 49.159 | 53.500 | 1.00 | 16.30 |
| ATOM | 1037 CB | ASP | A | 344 | −6.066 | 49.896 | 53.688 | 1.00 | 19.86 |
| ATOM | 1038 CG | ASP | A | 344 | −5.919 | 51.270 | 54.287 | 1.00 | 24.51 |
| ATOM | 1039 OD1 | ASP | A | 344 | −4.851 | 51.804 | 54.586 | 1.00 | 24.70 |
| ATOM | 1040 OD2 | ASP | A | 344 | −6.983 | 51.916 | 54.436 | 1.00 | 27.18 |
| ATOM | 1041 C | ASP | A | 344 | −5.093 | 47.675 | 53.396 | 1.00 | 13.85 |
| ATOM | 1042 O | ASP | A | 344 | −5.208 | 47.157 | 52.310 | 1.00 | 9.77 |
| ATOM | 1043 N | MET | A | 345 | −5.213 | 47.069 | 54.564 | 1.00 | 13.16 |
| ATOM | 1044 CA | MET | A | 345 | −5.708 | 45.753 | 54.800 | 1.00 | 17.11 |
| ATOM | 1045 CB | MET | A | 345 | −7.235 | 45.710 | 54.450 | 1.00 | 23.01 |
| ATOM | 1046 CG | MET | A | 345 | −7.944 | 46.687 | 55.406 | 1.00 | 28.99 |
| ATOM | 1047 SD | MET | A | 345 | −9.349 | 45.913 | 56.215 | 1.00 | 39.05 |
| ATOM | 1048 CE | MET | A | 345 | −9.993 | 47.308 | 57.172 | 1.00 | 36.28 |
| ATOM | 1049 C | MET | A | 345 | −4.992 | 44.658 | 54.023 | 1.00 | 16.11 |
| ATOM | 1050 O | MET | A | 345 | −5.586 | 43.729 | 53.496 | 1.00 | 11.01 |
| ATOM | 1051 N | GLY | A | 346 | −3.649 | 44.811 | 53.976 | 1.00 | 13.02 |
| ATOM | 1052 CA | GLY | A | 346 | −2.848 | 43.775 | 53.364 | 1.00 | 12.48 |
| ATOM | 1053 C | GLY | A | 346 | −2.754 | 43.637 | 51.897 | 1.00 | 10.57 |
| ATOM | 1054 O | GLY | A | 346 | −2.092 | 42.654 | 51.492 | 1.00 | 10.20 |
| ATOM | 1055 N | THR | A | 347 | −3.392 | 44.516 | 51.092 | 1.00 | 10.34 |
| ATOM | 1056 CA | THR | A | 347 | −3.236 | 44.419 | 49.645 | 1.00 | 10.83 |
| ATOM | 1057 CB | THR | A | 347 | −4.204 | 45.426 | 48.958 | 1.00 | 11.57 |
| ATOM | 1058 OG1 | THR | A | 347 | −5.515 | 45.104 | 49.474 | 1.00 | 11.02 |
| ATOM | 1059 CG2 | THR | A | 347 | −4.265 | 45.214 | 47.479 | 1.00 | 9.59 |
| ATOM | 1060 C | THR | A | 347 | −1.836 | 44.663 | 49.119 | 1.00 | 11.95 |
| ATOM | 1061 O | THR | A | 347 | −1.160 | 45.651 | 49.506 | 1.00 | 10.72 |
| ATOM | 1062 N | LEU | A | 348 | −1.400 | 43.853 | 48.171 | 1.00 | 9.29 |
| ATOM | 1063 CA | LEU | A | 348 | −0.082 | 43.950 | 47.585 | 1.00 | 11.62 |
| ATOM | 1064 CB | LEU | A | 348 | 0.550 | 42.518 | 47.580 | 1.00 | 11.68 |
| ATOM | 1065 CG | LEU | A | 348 | 0.940 | 41.992 | 48.967 | 1.00 | 13.21 |
| ATOM | 1066 CD1 | LEU | A | 348 | 1.053 | 40.466 | 48.924 | 1.00 | 13.82 |
| ATOM | 1067 CD2 | LEU | A | 348 | 2.282 | 42.599 | 49.398 | 1.00 | 13.80 |
| ATOM | 1068 C | LEU | A | 348 | −0.066 | 44.478 | 46.170 | 1.00 | 10.00 |
| ATOM | 1069 O | LEU | A | 348 | 0.889 | 45.107 | 45.724 | 1.00 | 10.81 |
| ATOM | 1070 N | GLY | A | 349 | −1.177 | 44.229 | 45.417 | 1.00 | 10.78 |
| ATOM | 1071 CA | GLY | A | 349 | −1.154 | 44.718 | 44.035 | 1.00 | 9.96 |

TABLE 1-continued

REMARK Created by MOLEMAN V. 961218/7.2.5 at Fri Sep 19 20:05:05 1997 for user carlos
REMARK Moleman FDS file

| CRYST1 | 61.387 | 126.278 | 81.273 | 90.00 | 107.42 | 90.00 | P 21 | 4 | |
|---|---|---|---|---|---|---|---|---|---|
| CRIGX1 | | 1.000000 | | 0.000000 | | | 0.000000 | | 0.00000 |
| CRIGX2 | | 0.000000 | | 1.000000 | | | 0.000000 | | 0.00000 |
| CRIGX3 | | 0.000000 | | 0.000000 | | | 1.000000 | | 0.00000 |
| SCALE1 | | 0.016290 | | 0.000000 | | | 0.005111 | | 0.00000 |
| SCALE2 | | 0.000000 | | 0.007919 | | | 0.000000 | | 0.00000 |
| SCALE3 | | 0.000000 | | 0.000000 | | | 0.012896 | | 0.00000 |

| | Atom Type | Residue | ! | # | X | Y | Z | OCC | B |
|---|---|---|---|---|---|---|---|---|---|
| ATOM | 1072 C | GLY | A | 349 | −2.577 | 44.686 | 43.420 | 1.00 | 11.05 |
| ATOM | 1073 O | GLY | A | 349 | −3.461 | 44.195 | 44.075 | 1.00 | 9.57 |
| ATOM | 1074 N | LEU | A | 250 | −2.667 | 45.177 | 42.201 | 1.00 | 12.61 |
| ATOM | 1075 CA | LEU | A | 350 | −4.033 | 45.102 | 41.592 | 1.00 | 12.78 |
| ATOM | 1076 CB | LEU | A | 350 | −4.766 | 46.348 | 42.090 | 1.00 | 13.89 |
| ATOM | 1077 CG | LEU | A | 350 | −6.279 | 46.356 | 41.850 | 1.00 | 16.31 |
| ATOM | 1078 CD1 | LEU | A | 350 | −6.981 | 45.416 | 42.807 | 1.00 | 17.00 |
| ATOM | 1079 CD2 | LEU | A | 350 | −6.786 | 47.797 | 41.945 | 1.00 | 15.79 |
| ATOM | 1080 C | LEU | A | 350 | −3.881 | 45.086 | 40.119 | 1.00 | 10.61 |
| ATOM | 1081 O | LEU | A | 350 | −2.867 | 45.625 | 39.674 | 1.00 | 9.12 |
| ATOM | 1082 N | ALA | A | 351 | −4.815 | 44.544 | 35.319 | 1.00 | 8.13 |
| ATOM | 1083 CA | ALA | A | 351 | −4.645 | 44.560 | 37.896 | 1.00 | 9.68 |
| ATOM | 1084 CB | ALA | A | 351 | −3.807 | 43.358 | 37.429 | 1.00 | 8.30 |
| ATOM | 1085 C | ALA | A | 351 | −6.006 | 44.393 | 37.158 | 1.00 | 8.00 |
| ATOM | 1086 O | ALA | A | 351 | −6.781 | 43.671 | 37.749 | 1.00 | 8.17 |
| ATOM | 1087 N | TYR | A | 352 | −6.102 | 44.923 | 35.997 | 1.00 | 10.56 |
| ATOM | 1088 CA | TYR | A | 352 | −7.378 | 44.669 | 35.243 | 1.00 | 11.99 |
| ATOM | 1089 CB | TYR | A | 352 | −7.517 | 45.727 | 34.152 | 1.00 | 13.49 |
| ATOM | 1090 CG | TYR | A | 352 | −7.816 | 47.102 | 34.704 | 1.00 | 16.49 |
| ATOM | 1091 CD1 | TYR | A | 352 | −9.085 | 47.388 | 35.198 | 1.00 | 18.25 |
| ATOM | 1092 CE1 | TYR | A | 352 | −9.369 | 48.643 | 35.704 | 1.00 | 18.58 |
| ATOM | 1093 CD2 | TYR | A | 352 | −6.835 | 48.096 | 34.726 | 1.00 | 15.80 |
| ATOM | 1094 CE2 | TYR | A | 352 | −7.121 | 49.344 | 35.231 | 1.00 | 17.33 |
| ATOM | 1095 CZ | TYR | A | 352 | −8.385 | 49.612 | 35.726 | 1.00 | 19.62 |
| ATOM | 1096 OH | TYE | A | 352 | −8.671 | 50.865 | 36.229 | 1.00 | 20.81 |
| ATOM | 1097 C | TYR | A | 352 | −7.306 | 43.297 | 34.623 | 1.00 | 11.61 |
| ATOM | 1098 O | TYR | A | 352 | −6.226 | 42.856 | 34.133 | 1.00 | 9.99 |
| ATOM | 1099 N | VAL | A | 353 | −8.414 | 42.569 | 34.618 | 1.00 | 9.19 |
| ATOM | 1100 CA | VAL | A | 353 | −8.433 | 41.240 | 34.027 | 1.00 | 9.63 |
| ATOM | 1101 CB | VAL | A | 353 | −9.532 | 40.388 | 34.675 | 1.00 | 12.16 |
| ATOM | 1102 CG1 | VAL | A | 353 | −9.580 | 38.963 | 34.168 | 1.00 | 11.71 |
| ATOM | 1103 CG2 | VAL | A | 353 | −9.337 | 40.459 | 36.180 | 1.00 | 11.77 |
| ATOM | 1104 C | VAL | A | 353 | −8.597 | 41.233 | 32.532 | 1.00 | 12.50 |
| ATOM | 1105 O | VAL | A | 353 | −9.522 | 41.869 | 32.012 | 1.00 | 12.29 |
| ATOM | 1106 N | GLY | A | 354 | −7.759 | 40.476 | 31.830 | 1.00 | 10.94 |
| ATOM | 1107 CA | GLY | A | 354 | −7.781 | 40.328 | 30.400 | 1.00 | 14.31 |
| ATOM | 1108 C | GLY | A | 354 | −8.927 | 39.377 | 29.976 | 1.00 | 14.67 |
| ATOM | 1109 O | GLY | A | 354 | −9.497 | 38.711 | 30.814 | 1.00 | 13.50 |
| ATOM | 1110 N | SER | A | 355 | −9.183 | 39.300 | 28.685 | 1.00 | 15.31 |
| ATOM | 1111 CA | SER | A | 355 | −10.226 | 38.340 | 28.254 | 1.00 | 18.47 |
| ATOM | 1112 CB | SER | A | 355 | −11.596 | 29.039 | 28.449 | 1.00 | 19.00 |
| ATOM | 1113 OG | SER | A | 355 | −12.631 | 38.360 | 27.760 | 1.00 | 21.32 |
| ATOM | 1114 C | SER | A | 355 | −9.959 | 38.049 | 26.808 | 1.00 | 17.63 |
| ATOM | 1115 O | SER | A | 355 | −9.378 | 38.937 | 26.168 | 1.00 | 18.38 |
| ATOM | 1116 N | PRO | A | 356 | −10.461 | 36.952 | 26.271 | 1.00 | 19.06 |
| ATOM | 1117 CD | PRO | A | 356 | −11.125 | 35.862 | 27.017 | 1.00 | 18.95 |
| ATOM | 1118 CA | PRO | A | 356 | −10.370 | 36.661 | 24.859 | 1.00 | 21.26 |
| ATOM | 1119 CB | PRO | A | 356 | −10.771 | 35.200 | 24.707 | 1.00 | 20.19 |
| ATOM | 1120 CG | PRO | A | 356 | −11.451 | 34.834 | 25.974 | 1.00 | 20.51 |
| ATOM | 1121 C | PRO | A | 356 | −11.357 | 37.502 | 24.051 | 1.00 | 24.27 |
| ATOM | 1122 O | PRO | A | 356 | −11.249 | 37.622 | 22.833 | 1.00 | 25.16 |
| ATOM | 1123 N | ARG | A | 357 | −12.369 | 38.028 | 24.714 | 1.00 | 27.47 |
| ATOM | 1124 NH2 | ARG | A | 357 | −14.829 | 39.823 | 29.846 | 1.00 | 45.75 |
| ATOM | 1125 NH1 | ARG | A | 357 | −15.278 | 41.187 | 28.059 | 1.00 | 45.46 |
| ATOM | 1126 CZ | ARG | A | 357 | −15.278 | 39.980 | 28.609 | 1.00 | 43.96 |
| ATOM | 1127 NE | ARG | A | 357 | −15.708 | 38.909 | 27.965 | 1.00 | 41.93 |
| ATOM | 1128 CD | ARG | A | 357 | −16.239 | 38.818 | 26.627 | 1.00 | 38.04 |
| ATOM | 1129 CG | ARG | A | 357 | −15.252 | 38.219 | 25.641 | 1.00 | 34.46 |
| ATOM | 1130 CB | ARG | A | 357 | −14.476 | 39.345 | 24.961 | 1.00 | 32.97 |
| ATOM | 1131 CA | ARG | A | 357 | −13.386 | 33.812 | 24.032 | 1.00 | 31.58 |
| ATOM | 1132 C | ARG | A | 357 | −12.777 | 39.943 | 23.231 | 1.00 | 33.38 |
| ATOM | 1133 O | ARG | A | 357 | −11.979 | 40.784 | 23.635 | 1.00 | 32.52 |
| ATOM | 1134 CB | ALA | A | 358 | −13.971 | 40.872 | 19.874 | 1.00 | 35.32 |
| ATOM | 1135 C | ALA | A | 358 | −12.904 | 42.350 | 21.524 | 1.00 | 36.30 |
| ATOM | 1136 O | ALA | A | 358 | −11.940 | 43.090 | 21.425 | 1.00 | 37.79 |
| ATOM | 1137 N | ALA | A | 358 | −13.235 | 39.948 | 21.981 | 1.00 | 35.10 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | | 0.000000 | | 0.00000 |
| CRIGX2 | | 0.000000 | | 1.000000 | | | 0.000000 | | 0.00000 |
| CRIGX3 | | 0.000000 | | 0.000000 | | | 1.000000 | | 0.00000 |
| SCALE1 | | 0.016290 | | 0.000000 | | | 0.005111 | | 0.00000 |
| SCALE2 | | 0.000000 | | 0.007919 | | | 0.000000 | | 0.00000 |
| SCALE3 | | 0.000000 | | 0.000000 | | | 0.012896 | | 0.00000 |

| | Atom Type | Residue | ! | # | X | Y | Z | OCC | B |
|---|---|---|---|---|---|---|---|---|---|
| ATOM | 1138 CA | ALA | A | 358 | −12.901 | 40.933 | 20.979 | 1.00 | 36.40 |
| ATOM | 1139 N | ASN | A | 359 | −14.027 | 42.745 | 22.100 | 1.00 | 36.18 |
| ATOM | 1140 ND2 | ASN | A | 359 | −17.589 | 44.247 | 20.981 | 1.00 | 38.54 |
| ATOM | 1141 OD1 | ASN | A | 359 | −15.577 | 44.791 | 20.178 | 1.00 | 40.48 |
| ATOM | 1142 CG | ASN | A | 359 | −16.290 | 44.493 | 21.132 | 1.00 | 39.04 |
| ATOM | 1143 CB | ASN | A | 359 | −15.760 | 44.367 | 22.540 | 1.00 | 37.70 |
| ATOM | 1144 CA | ASN | A | 359 | −14.263 | 44.061 | 22.641 | 1.00 | 36.27 |
| ATOM | 1145 C | ASN | A | 359 | −13.834 | 44.198 | 24.094 | 1.00 | 35.65 |
| ATOM | 1146 O | ASN | A | 359 | −14.157 | 45.182 | 24.751 | 1.00 | 35.92 |
| ATOM | 1147 N | SER | A | 360 | −13.119 | 43.218 | 24.615 | 1.00 | 34.08 |
| ATOM | 1148 OG | SER | A | 360 | −10.429 | 42.540 | 26.749 | 1.00 | 34.50 |
| ATOM | 1149 CB | SER | A | 360 | −11.683 | 42.108 | 26.257 | 1.00 | 33.68 |
| ATOM | 1150 CA | SER | A | 360 | −12.647 | 43.261 | 25.982 | 1.00 | 32.95 |
| ATOM | 1151 C | SER | A | 360 | −11.907 | 44.577 | 26.260 | 1.00 | 30.62 |
| ATOM | 1152 O | SER | A | 360 | −11.073 | 45.055 | 25.505 | 1.00 | 29.59 |
| ATOM | 1153 N | HIS | A | 361 | −12.244 | 45.128 | 27.405 | 1.00 | 28.43 |
| ATOM | 1154 CD2 | HIS | A | 361 | −14.316 | 47.743 | 26.576 | 1.00 | 37.21 |
| ATOM | 1155 NE2 | HIS | A | 361 | −14.610 | 48.664 | 25.596 | 1.00 | 37.98 |
| ATOM | 1156 CE1 | HIS | A | 361 | −13.624 | 49.531 | 25.503 | 1.00 | 37.94 |
| ATOM | 1157 ND1 | HIS | A | 361 | −12.729 | 49.221 | 26.413 | 1.00 | 38.32 |
| ATOM | 1158 CG | HIS | A | 361 | −13.138 | 43.108 | 27.110 | 1.00 | 36.46 |
| ATOM | 1159 CB | HIS | A | 361 | −12.374 | 47.488 | 28.234 | 1.00 | 33.76 |
| ATOM | 1160 CA | HIS | A | 361 | −11.550 | 45.275 | 27.920 | 1.00 | 30.24 |
| ATOM | 1161 C | HIS | A | 361 | −10.928 | 45.653 | 29.193 | 1.00 | 29.98 |
| ATOM | 1162 O | HIS | A | 361 | −11.660 | 45.080 | 30.014 | 1.00 | 33.02 |
| ATOM | 1163 N | GLY | A | 362 | −9.625 | 45.543 | 29.184 | 1.00 | 25.53 |
| ATOM | 1164 CA | GLY | A | 362 | −8.942 | 45.064 | 30.372 | 1.00 | 20.70 |
| ATOM | 1165 C | GLY | A | 362 | −7.829 | 44.108 | 29.983 | 1.00 | 16.68 |
| ATOM | 1166 O | GLY | A | 362 | −7.986 | 43.330 | 29.056 | 1.00 | 12.10 |
| ATOM | 1167 N | GLY | A | 363 | −6.695 | 44.301 | 30.672 | 1.00 | 13.81 |
| ATOM | 1168 CA | GLY | A | 363 | −5.648 | 43.339 | 30.406 | 1.00 | 14.18 |
| ATOM | 1169 C | GLY | A | 363 | −4.908 | 43.513 | 29.110 | 1.00 | 13.66 |
| ATOM | 1170 O | GLY | A | 363 | −4.808 | 44.608 | 28.557 | 1.00 | 12.16 |
| ATOM | 1171 N | VAL | A | 364 | −4.310 | 42.413 | 28.673 | 1.00 | 14.17 |
| ATOM | 1172 CG2 | VAL | A | 364 | −4.030 | 40.030 | 27.062 | 1.00 | 15.53 |
| ATOM | 1173 CG1 | VAL | A | 364 | −1.902 | 40.628 | 28.266 | 1.00 | 15.36 |
| ATOM | 1174 CB | VAL | A | 364 | −2.897 | 41.047 | 27.174 | 1.00 | 18.71 |
| ATOM | 1175 CA | VAL | A | 364 | −3.455 | 42.442 | 27.502 | 1.00 | 17.47 |
| ATOM | 1176 C | VAL | A | 364 | −4.138 | 43.070 | 26.294 | 1.00 | 22.13 |
| ATOM | 1177 O | VAL | A | 364 | −5.313 | 42.870 | 26.039 | 1.00 | 18.74 |
| ATOM | 1178 N | CYS | A | 365 | −3.323 | 43.852 | 25.611 | 1.00 | 26.09 |
| ATOM | 1179 SG | CYS | A | 365 | −3.257 | 42.201 | 22.935 | 1.00 | 38.70 |
| ATOM | 1180 CB | CYS | A | 365 | −4.184 | 43.720 | 23.283 | 1.00 | 34.15 |
| ATOM | 1181 CA | CYS | A | 365 | −3.608 | 44.572 | 24.400 | 1.00 | 32.02 |
| ATOM | 1182 C | CYS | A | 365 | −4.433 | 45.808 | 24.718 | 1.00 | 32.84 |
| ATOM | 1183 O | CYS | A | 365 | −5.505 | 45.800 | 25.307 | 1.00 | 33.41 |
| ATOM | 1184 N | PRO | A | 366 | −3.826 | 46.943 | 24.391 | 1.00 | 34.94 |
| ATOM | 1185 CG | PRO | A | 366 | −2.315 | 48.596 | 23.731 | 1.00 | 34.57 |
| ATOM | 1186 CD | PRO | A | 366 | −2.542 | 47.119 | 23.698 | 1.00 | 34.14 |
| ATOM | 1187 CB | PRO | A | 366 | −3.403 | 49.216 | 24.501 | 1.00 | 35.23 |
| ATOM | 1188 CA | PRO | A | 366 | −4.515 | 48.220 | 24.644 | 1.00 | 35.75 |
| ATOM | 1189 C | PRO | A | 366 | −5.714 | 48.244 | 23.715 | 1.00 | 36.16 |
| ATOM | 1190 O | PRO | A | 366 | −5.574 | 47.917 | 22.548 | 1.00 | 38.73 |
| ATOM | 1191 N | LYS | A | 367 | −6.905 | 48.420 | 24.211 | 1.00 | 36.55 |
| ATOM | 1192 NZ | LYS | A | 367 | −11.060 | 46.083 | 19.713 | 1.00 | 39.83 |
| ATOM | 1193 CE | LYS | A | 367 | −10.945 | 46.830 | 20.990 | 1.00 | 39.58 |
| ATOM | 1194 CD | LYS | A | 367 | −10.461 | 45.989 | 22.141 | 1.00 | 39.79 |
| ATOM | 1195 CG | LYS | A | 367 | −9.071 | 46.373 | 22.617 | 1.00 | 39.82 |
| ATOM | 1196 CB | LYS | A | 367 | −9.031 | 47.227 | 23.867 | 1.00 | 36.78 |
| ATOM | 1197 CA | LYS | A | 367 | −8.228 | 48.530 | 23.676 | 1.00 | 37.98 |
| ATOM | 1198 C | LYS | A | 367 | −8.995 | 49.679 | 24.375 | 1.00 | 36.54 |
| ATOM | 1199 O | LYS | A | 367 | −9.725 | 49.528 | 25.366 | 1.00 | 33.85 |
| ATOM | 1200 N | ALA | A | 368 | −8.855 | 50.888 | 23.839 | 1.00 | 35.07 |
| ATOM | 1201 CA | ALA | A | 368 | −9.376 | 52.113 | 24.400 | 1.00 | 32.73 |
| ATOM | 1202 CB | ALA | A | 368 | −9.170 | 53.209 | 23.330 | 1.00 | 34.00 |
| ATOM | 1203 C | ALA | A | 368 | −10.770 | 52.317 | 24.933 | 1.00 | 32.95 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 1204 O | ALA | A | 368 | −11.784 | 51.928 | 24.364 | 1.00 | 32.14 |
| ATOM | 1205 N | TYR | A | 369 | −10.878 | 53.117 | 25.991 | 1.00 | 31.03 |
| ATOM | 1206 CA | TYR | A | 369 | −12.087 | 53.643 | 26.567 | 1.00 | 32.06 |
| ATOM | 1207 CB | TYR | A | 369 | −12.264 | 53.583 | 28.057 | 1.00 | 34.85 |
| ATOM | 1208 CG | TYR | A | 369 | −13.026 | 52.465 | 28.689 | 1.00 | 37.47 |
| ATOM | 1209 CD1 | TYR | A | 369 | −12.349 | 51.435 | 29.321 | 1.00 | 38.45 |
| ATOM | 1210 CE1 | TYR | A | 369 | −13.025 | 50.390 | 29.914 | 1.00 | 39.73 |
| ATOM | 1211 CD2 | TYR | A | 369 | −14.410 | 52.415 | 28.669 | 1.00 | 39.08 |
| ATOM | 1212 CE2 | TYR | A | 369 | −15.096 | 51.380 | 29.271 | 1.00 | 40.46 |
| ATOM | 1213 CZ | TYR | A | 369 | −14.397 | 50.369 | 29.891 | 1.00 | 41.04 |
| ATOM | 1214 OH | TYR | A | 369 | −15.067 | 49.320 | 30.483 | 1.00 | 42.68 |
| ATOM | 1215 C | TYR | A | 369 | −11.953 | 55.158 | 26.287 | 1.00 | 32.03 |
| ATOM | 1216 O | TYR | A | 369 | −10.842 | 55.634 | 26.529 | 1.00 | 28.95 |
| ATOM | 1217 N | TYR | A | 370 | −12.996 | 55.828 | 25.851 | 1.00 | 32.03 |
| ATOM | 1218 OH | TYR | A | 370 | −13.216 | 63.382 | 23.761 | 1.00 | 38.96 |
| ATOM | 1219 CD2 | TYR | A | 370 | −14.752 | 60.205 | 24.698 | 1.00 | 36.28 |
| ATOM | 1220 CE2 | TYR | A | 370 | −14.597 | 61.568 | 24.490 | 1.00 | 36.78 |
| ATOM | 1221 CZ | TYR | A | 370 | −13.409 | 62.034 | 23.975 | 1.00 | 37.70 |
| ATOM | 1222 CE1 | TYR | A | 370 | −12.383 | 61.168 | 23.662 | 1.00 | 36.85 |
| ATOM | 1223 CD1 | TYR | A | 370 | −12.563 | 59.820 | 23.871 | 1.00 | 35.73 |
| ATOM | 1224 CG | TYR | A | 370 | −13.741 | 59.312 | 24.388 | 1.00 | 35.35 |
| ATOM | 1225 CB | TYR | A | 370 | −13.896 | 57.816 | 24.613 | 1.00 | 34.74 |
| ATOM | 1226 CA | TYR | A | 370 | −12.850 | 57.254 | 25.574 | 1.00 | 33.23 |
| ATOM | 1227 C | TYR | A | 370 | −12.982 | 57.999 | 26.897 | 1.00 | 33.56 |
| ATOM | 1228 O | TYR | A | 370 | −13.819 | 57.580 | 27.684 | 1.00 | 33.28 |
| ATOM | 1229 N | SER | A | 371 | −12.169 | 59.015 | 27.125 | 1.00 | 35.61 |
| ATOM | 1230 OG | SER | A | 371 | −10.952 | 60.534 | 30.263 | 1.00 | 37.79 |
| ATOM | 1231 CB | SER | A | 371 | −10.994 | 59.623 | 29.183 | 1.00 | 39.02 |
| ATOM | 1232 CA | SER | A | 371 | −12.297 | 59.726 | 28.389 | 1.00 | 38.04 |
| ATOM | 1233 C | SER | A | 371 | −12.666 | 61.187 | 28.201 | 1.00 | 39.91 |
| ATOM | 1234 O | SER | A | 371 | −11.843 | 62.022 | 27.853 | 1.00 | 38.57 |
| ATOM | 1235 N | PRO | A | 372 | −13.931 | 61.484 | 28.820 | 1.00 | 43.18 |
| ATOM | 1236 CG | PRO | A | 372 | −16.243 | 61.324 | 28.452 | 1.00 | 44.76 |
| ATOM | 1237 CD | PRO | A | 372 | −15.008 | 60.574 | 28.867 | 1.00 | 44.03 |
| ATOM | 1238 CB | PRO | A | 372 | −15.900 | 62.772 | 28.425 | 1.00 | 45.09 |
| ATOM | 1239 CA | PRO | A | 372 | −14.403 | 62.878 | 28.437 | 1.00 | 45.43 |
| ATOM | 1240 C | PRO | A | 372 | −13.833 | 63.366 | 29.760 | 1.00 | 46.59 |
| ATOM | 1241 O | PRO | A | 372 | −14.102 | 62.743 | 30.789 | 1.00 | 47.64 |
| ATOM | 1242 N | VAL | A | 373 | −12.978 | 64.362 | 25.767 | 1.00 | 48.18 |
| ATOM | 1243 CG2 | VAL | A | 373 | −13.693 | 65.070 | 32.937 | 1.00 | 48.74 |
| ATOM | 1244 CG1 | VAL | A | 373 | −11.354 | 64.454 | 33.270 | 1.00 | 48.15 |
| ATOM | 1245 CB | VAL | A | 373 | −12.534 | 64.295 | 32.314 | 1.00 | 48.02 |
| ATOM | 1246 CA | VAL | A | 373 | −12.176 | 64.754 | 30.916 | 1.00 | 47.53 |
| ATOM | 1247 C | VAL | A | 373 | −10.843 | 64.081 | 30.527 | 1.00 | 47.84 |
| ATOM | 1248 O | VAL | A | 373 | −10.706 | 62.871 | 30.685 | 1.00 | 48.07 |
| ATOM | 1249 N | GLY | A | 374 | −9.966 | 64.870 | 29.936 | 1.00 | 46.71 |
| ATOM | 1250 CA | GLY | A | 374 | −8.687 | 64.329 | 29.474 | 1.00 | 45.92 |
| ATOM | 1251 C | GLY | A | 374 | −8.718 | 64.327 | 27.946 | 1.00 | 44.34 |
| ATOM | 1252 O | GLY | A | 374 | −7.703 | 64.386 | 27.276 | 1.00 | 43.53 |
| ATOM | 1253 N | LYS | A | 375 | −9.937 | 64.227 | 27.433 | 1.00 | 20.00 |
| ATOM | 1254 NZ | LYS | A | 375 | −11.621 | 70.469 | 25.481 | 1.00 | 20.00 |
| ATOM | 1255 CE | LYS | A | 375 | −11.822 | 69.108 | 25.996 | 1.00 | 20.00 |
| ATOM | 1256 CD | LYS | A | 375 | −10.786 | 68.111 | 25.474 | 1.00 | 20.00 |
| ATOM | 1257 CG | LYS | A | 375 | −10.999 | 66.697 | 26.013 | 1.00 | 20.00 |
| ATOM | 1258 CB | LYS | A | 375 | −9.976 | 65.697 | 25.486 | 1.00 | 20.00 |
| ATOM | 1259 CA | LYS | A | 375 | −10.201 | 64.262 | 26.011 | 1.00 | 20.00 |
| ATOM | 1260 C | LYS | A | 375 | −9.308 | 63.297 | 25.260 | 1.00 | 20.00 |
| ATOM | 1261 O | LYS | A | 375 | −8.529 | 63.725 | 24.411 | 1.00 | 20.00 |
| ATOM | 1262 N | LYS | A | 376 | −9.385 | 62.003 | 25.604 | 1.00 | 20.00 |
| ATOM | 1263 NZ | LYS | A | 376 | −3.285 | 64.692 | 24.559 | 1.00 | 20.00 |
| ATOM | 1264 CE | LYS | A | 376 | −4.696 | 64.381 | 24.290 | 1.00 | 20.00 |
| ATOM | 1265 CD | LYS | A | 376 | −5.139 | 63.045 | 24.890 | 1.00 | 20.00 |
| ATOM | 1266 CG | LYS | A | 376 | −6.606 | 62.726 | 24.608 | 1.00 | 20.00 |
| ATOM | 1267 CB | LYS | A | 376 | −7.050 | 61.390 | 25.194 | 1.00 | 20.00 |
| ATOM | 1268 CA | LYS | A | 376 | −8.531 | 61.050 | 24.897 | 1.00 | 20.00 |
| ATOM | 1269 C | LYS | A | 376 | −8.810 | 59.601 | 25.286 | 1.00 | 20.00 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 1270 O | LYS | A | 376 | −9.696 | 59.281 | 26.077 | 1.00 | 20.00 |
| ATOM | 1271 N | ASN | A | 377 | −8.050 | 53.726 | 24.640 | 1.00 | 29.74 |
| ATOM | 1272 CA | ASN | A | 377 | −8.240 | 57.295 | 24.862 | 1.00 | 29.33 |
| ATOM | 1273 CB | ASN | A | 377 | −7.825 | 56.539 | 23.612 | 1.00 | 29.66 |
| ATOM | 1274 CG | ASN | A | 377 | −8.743 | 56.803 | 22.433 | 1.00 | 30.76 |
| ATOM | 1275 OD1 | ASN | A | 377 | −9.964 | 56.948 | 22.559 | 1.00 | 29.66 |
| ATOM | 1276 ND2 | ASN | A | 377 | −8.128 | 56.865 | 21.249 | 1.00 | 31.26 |
| ATOM | 1277 C | ASN | A | 377 | −7.486 | 56.848 | 26.098 | 1.00 | 28.35 |
| ATOM | 1278 O | ASN | A | 377 | −6.411 | 57.376 | 26.306 | 1.00 | 26.83 |
| ATOM | 1279 N | ILE | A | 378 | −8.123 | 56.055 | 26.952 | 1.00 | 26.88 |
| ATOM | 1280 CA | ILE | A | 378 | −7.431 | 55.408 | 25.039 | 1.00 | 28.08 |
| ATOM | 1281 CB | ILE | A | 378 | −7.802 | 55.780 | 29.473 | 1.00 | 29.37 |
| ATOM | 1282 CG2 | ILE | A | 378 | −7.624 | 57.282 | 29.706 | 1.00 | 28.66 |
| ATOM | 1283 CG1 | ILE | A | 378 | −9.217 | 55.317 | 29.789 | 1.00 | 31.06 |
| ATOM | 1284 CD1 | ILE | A | 378 | −9.563 | 55.101 | 31.261 | 1.00 | 32.92 |
| ATOM | 1285 C | ILE | A | 378 | −7.567 | 53.887 | 27.882 | 1.00 | 26.65 |
| ATOM | 1286 O | ILE | A | 378 | −8.559 | 53.283 | 27.473 | 1.00 | 25.21 |
| ATOM | 1287 N | TYR | A | 379 | −6.456 | 53.246 | 28.250 | 1.00 | 25.14 |
| ATOM | 1288 CA | TYR | A | 379 | −6.298 | 51.805 | 28.141 | 1.00 | 23.62 |
| ATOM | 1289 CB | TYR | A | 379 | −5.057 | 51.473 | 27.299 | 1.00 | 25.30 |
| ATOM | 1290 CG | TYR | A | 379 | −5.076 | 52.202 | 25.979 | 1.00 | 27.60 |
| ATOM | 1291 CD1 | TYR | A | 379 | −4.644 | 53.523 | 25.919 | 1.00 | 28.62 |
| ATOM | 1292 CE1 | TYR | A | 379 | −4.683 | 54.224 | 24.736 | 1.00 | 30.42 |
| ATOM | 1293 CD2 | TYR | A | 379 | −5.571 | 51.619 | 24.836 | 1.00 | 28.58 |
| ATOM | 1294 CE2 | TYR | A | 379 | −5.582 | 52.298 | 23.534 | 1.00 | 29.43 |
| ATOM | 1295 CZ | TYR | A | 379 | −5.141 | 53.597 | 23.603 | 1.00 | 30.50 |
| ATOM | 1296 OH | TYR | A | 379 | −5.162 | 54.325 | 22.441 | 1.00 | 33.44 |
| ATOM | 1297 C | TYR | A | 379 | −6.141 | 51.154 | 29.498 | 1.00 | 22.07 |
| ATOM | 1298 O | TYR | A | 379 | −5.164 | 51.460 | 30.204 | 1.00 | 22.84 |
| ATOM | 1299 N | LEU | A | 380 | −6.941 | 50.122 | 29.768 | 1.00 | 16.20 |
| ATOM | 1300 CA | LEU | A | 380 | −6.831 | 49.396 | 30.998 | 1.00 | 17.68 |
| ATOM | 1301 CB | LEU | A | 380 | −8.233 | 49.019 | 31.490 | 1.00 | 19.14 |
| ATOM | 1302 CG | LEU | A | 380 | −9.204 | 50.207 | 31.624 | 1.00 | 21.74 |
| ATOM | 1303 CD1 | LEU | A | 380 | −10.479 | 49.690 | 32.285 | 1.00 | 22.06 |
| ATOM | 1304 CD2 | LEU | A | 380 | −8.614 | 51.364 | 32.411 | 1.00 | 20.08 |
| ATOM | 1305 C | LEU | A | 380 | −5.903 | 48.191 | 30.845 | 1.00 | 13.92 |
| ATOM | 1306 O | LEU | A | 380 | −6.249 | 47.139 | 31.351 | 1.00 | 12.26 |
| ATOM | 1307 N | ASN | A | 381 | −4.762 | 48.385 | 30.190 | 1.00 | 14.40 |
| ATOM | 1308 CA | ASN | A | 381 | −3.798 | 47.282 | 30.009 | 1.00 | 15.71 |
| ATOM | 1309 CB | ASN | A | 381 | −3.148 | 47.364 | 28.646 | 1.00 | 13.12 |
| ATOM | 1310 CG | ASN | A | 381 | −2.442 | 48.681 | 28.373 | 1.00 | 13.93 |
| ATOM | 1311 OD1 | ASN | A | 381 | −2.614 | 49.693 | 29.057 | 1.00 | 15.98 |
| ATOM | 1312 ND2 | ASN | A | 381 | −1.584 | 48.766 | 27.386 | 1.00 | 13.77 |
| ATOM | 1313 C | ASN | A | 381 | −2.732 | 47.428 | 31.111 | 1.00 | 15.34 |
| ATOM | 1314 O | ASN | A | 381 | −1.538 | 47.496 | 30.826 | 1.00 | 19.25 |
| ATOM | 1315 N | SER | A | 382 | −3.178 | 47.587 | 32.318 | 1.00 | 14.28 |
| ATOM | 1316 CA | SER | A | 382 | −2.363 | 47.953 | 33.462 | 1.00 | 16.49 |
| ATOM | 1317 CB | SER | A | 382 | −2.722 | 49.449 | 33.712 | 1.00 | 19.36 |
| ATOM | 1318 OG | SER | A | 382 | −4.021 | 49.622 | 34.261 | 1.00 | 19.22 |
| ATOM | 1319 C | SER | A | 382 | −2.534 | 47.168 | 34.720 | 1.00 | 13.50 |
| ATOM | 1320 O | SER | A | 382 | −3.491 | 46.443 | 34.986 | 1.00 | 14.79 |
| ATOM | 1321 N | GLY | A | 383 | −1.543 | 47.226 | 35.602 | 1.00 | 12.08 |
| ATOM | 1322 CA | GLY | A | 383 | −1.460 | 46.552 | 36.865 | 1.00 | 7.68 |
| ATOM | 1323 C | GLY | A | 383 | −0.407 | 47.250 | 37.737 | 1.00 | 9.13 |
| ATOM | 1324 O | GLY | A | 383 | 0.356 | 48.018 | 37.167 | 1.00 | 7.23 |
| ATOM | 1325 N | LEU | A | 384 | −0.406 | 46.961 | 39.018 | 1.00 | 9.60 |
| ATOM | 1326 CA | LEU | A | 384 | 0.596 | 47.604 | 39.860 | 1.00 | 10.98 |
| ATOM | 1327 CB | LEU | A | 384 | 0.108 | 48.911 | 40.437 | 1.00 | 10.87 |
| ATOM | 1328 CG | LEU | A | 384 | −1.098 | 48.840 | 41.372 | 1.00 | 12.55 |
| ATOM | 1329 CD1 | LEU | A | 384 | −0.751 | 48.583 | 42.819 | 1.00 | 11.84 |
| ATOM | 1330 CD2 | LEU | A | 384 | −1.824 | 50.197 | 41.305 | 1.00 | 14.27 |
| ATOM | 1331 C | LEU | A | 384 | 0.963 | 46.614 | 40.982 | 1.00 | 11.40 |
| ATOM | 1332 O | LEU | A | 384 | 0.191 | 45.705 | 41.269 | 1.00 | 12.17 |
| ATOM | 1333 N | THR | A | 385 | 2.174 | 46.774 | 41.470 | 1.00 | 10.30 |
| ATOM | 1334 CA | THR | A | 385 | 2.773 | 45.977 | 42.535 | 1.00 | 10.05 |
| ATOM | 1335 CB | THR | A | 385 | 3.958 | 45.170 | 41.969 | 1.00 | 11.82 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | | 0.000000 | | 0.00000 |
| CRIGX2 | | 0.000000 | | 1.000000 | | | 0.000000 | | 0.00000 |
| CRIGX3 | | 0.000000 | | 0.000000 | | | 1.000000 | | 0.00000 |
| SCALE1 | | 0.016290 | | 0.000000 | | | 0.005111 | | 0.00000 |
| SCALE2 | | 0.000000 | | 0.007919 | | | 0.000000 | | 0.00000 |
| SCALE3 | | 0.000000 | | 0.000000 | | | 0.012896 | | 0.00000 |

| | Atom Type | | Residue | ! | # | X | Y | Z | OCC | B |
|---|---|---|---|---|---|---|---|---|---|---|
| ATOM | 1336 | OG1 | THR | A | 385 | 3.463 | 44.161 | 41.100 | 1.00 | 12.53 |
| ATOM | 1337 | CG2 | THR | A | 385 | 4.842 | 44.430 | 42.991 | 1.00 | 7.93 |
| ATOM | 1338 | C | THR | A | 385 | 3.429 | 46.936 | 43.546 | 1.00 | 10.37 |
| ATOM | 1339 | O | THR | A | 385 | 4.154 | 47.869 | 43.150 | 1.00 | 10.04 |
| ATOM | 1340 | N | SER | A | 386 | 3.153 | 46.751 | 44.806 | 1.00 | 10.16 |
| ATOM | 1341 | CA | SER | A | 386 | 3.835 | 47.470 | 45.853 | 1.00 | 12.08 |
| ATOM | 1342 | CB | SER | A | 386 | 2.913 | 47.978 | 46.925 | 1.00 | 12.65 |
| ATOM | 1343 | OG | SER | A | 386 | 3.625 | 48.590 | 47.976 | 1.00 | 12.90 |
| ATOM | 1344 | C | SER | A | 386 | 4.773 | 46.445 | 46.540 | 1.00 | 11.71 |
| ATOM | 1345 | O | SER | A | 386 | 4.348 | 45.314 | 46.714 | 1.00 | 11.70 |
| ATOM | 1346 | N | THR | A | 387 | 5.929 | 46.899 | 46.978 | 1.00 | 13.21 |
| ATOM | 1347 | CA | THR | A | 387 | 6.861 | 46.004 | 47.677 | 1.00 | 11.54 |
| ATOM | 1348 | CB | THR | A | 387 | 8.258 | 45.976 | 47.083 | 1.00 | 12.46 |
| ATOM | 1349 | OG1 | THR | A | 387 | 8.794 | 47.305 | 46.902 | 1.00 | 12.52 |
| ATOM | 1350 | CG2 | THR | A | 387 | 8.193 | 45.224 | 45.771 | 1.00 | 9.84 |
| ATOM | 1351 | C | THR | A | 387 | 6.917 | 46.429 | 49.137 | 1.00 | 12.59 |
| ATOM | 1352 | O | THR | A | 387 | 7.750 | 45.916 | 49.857 | 1.00 | 9.86 |
| ATOM | 1353 | N | LYS | A | 388 | 5.888 | 47.176 | 49.559 | 1.00 | 10.11 |
| ATOM | 1354 | CA | LYS | A | 388 | 5.781 | 47.451 | 50.983 | 1.00 | 11.18 |
| ATOM | 1355 | CB | LYS | A | 388 | 5.844 | 48.928 | 51.315 | 1.00 | 10.27 |
| ATOM | 1356 | CG | LYS | A | 388 | 5.598 | 49.163 | 52.809 | 1.00 | 11.78 |
| ATOM | 1357 | CD | LYS | A | 388 | 5.570 | 50.665 | 53.086 | 1.00 | 12.59 |
| ATOM | 1358 | CE | LYS | A | 388 | 5.610 | 50.846 | 54.616 | 1.00 | 12.42 |
| ATOM | 1359 | NZ | LYS | A | 388 | 5.400 | 52.289 | 54.915 | 1.00 | 12.86 |
| ATOM | 1360 | C | LYS | A | 388 | 4.466 | 46.836 | 51.470 | 1.00 | 12.79 |
| ATOM | 1361 | O | LYS | A | 388 | 3.445 | 47.068 | 50.803 | 1.00 | 13.47 |
| ATOM | 1362 | N | ASN | A | 389 | 4.490 | 46.117 | 52.561 | 1.00 | 11.20 |
| ATOM | 1363 | CA | ASN | A | 389 | 3.235 | 45.595 | 53.114 | 1.00 | 13.05 |
| ATOM | 1364 | CB | ASN | A | 389 | 2.797 | 44.247 | 52.498 | 1.00 | 9.98 |
| ATOM | 1365 | CG | ASN | A | 389 | 1.328 | 43.929 | 52.695 | 1.00 | 13.57 |
| ATOM | 1366 | OD1 | ASN | A | 389 | 0.562 | 44.523 | 53.020 | 1.00 | 11.41 |
| ATOM | 1367 | ND2 | ASN | A | 389 | 0.828 | 42.697 | 52.544 | 1.00 | 11.87 |
| ATOM | 1368 | C | ASN | A | 389 | 3.401 | 45.431 | 54.605 | 1.00 | 12.01 |
| ATOM | 1369 | O | ASN | A | 389 | 4.389 | 44.832 | 55.045 | 1.00 | 12.68 |
| ATOM | 1370 | N | TYR | A | 390 | 2.463 | 45.891 | 55.415 | 1.00 | 9.33 |
| ATOM | 1371 | CA | TYR | A | 390 | 2.544 | 45.725 | 56.834 | 1.00 | 11.32 |
| ATOM | 1372 | CB | TYR | A | 390 | 2.395 | 44.317 | 57.360 | 1.00 | 13.01 |
| ATOM | 1373 | CG | TYR | A | 390 | 1.034 | 43.646 | 57.138 | 1.00 | 17.63 |
| ATOM | 1374 | CD1 | TYR | A | 390 | 0.888 | 42.699 | 56.135 | 1.00 | 17.99 |
| ATOM | 1375 | CE1 | TYR | A | 390 | −0.324 | 42.059 | 55.906 | 1.00 | 18.34 |
| ATOM | 1376 | CD2 | TYR | A | 390 | −0.059 | 43.050 | 57.918 | 1.00 | 17.56 |
| ATOM | 1377 | CE2 | TYR | A | 390 | −1.295 | 43.344 | 57.684 | 1.00 | 19.81 |
| ATOM | 1378 | CZ | TYR | A | 390 | −1.408 | 42.399 | 56.685 | 1.00 | 18.72 |
| ATOM | 1379 | OH | TYR | A | 390 | −2.599 | 41.770 | 56.456 | 1.00 | 18.16 |
| ATOM | 1380 | C | TYR | A | 390 | 3.875 | 46.390 | 57.342 | 1.00 | 11.32 |
| ATOM | 1381 | O | TYR | A | 390 | 4.444 | 45.867 | 58.262 | 1.00 | 10.06 |
| ATOM | 1382 | N | GLY | A | 391 | 4.202 | 47.568 | 56.849 | 1.00 | 12.38 |
| ATOM | 1383 | CA | GLY | A | 391 | 5.264 | 48.396 | 57.395 | 1.00 | 13.46 |
| ATOM | 1384 | C | GLY | A | 391 | 6.671 | 47.822 | 57.226 | 1.00 | 14.75 |
| ATOM | 1385 | O | GLY | A | 391 | 7.615 | 48.218 | 57.920 | 1.00 | 13.47 |
| ATOM | 1386 | N | LYS | A | 392 | 6.864 | 47.001 | 56.213 | 1.00 | 14.18 |
| ATOM | 1387 | NZ | LYS | A | 392 | 6.391 | 42.087 | 59.901 | 1.00 | 31.24 |
| ATOM | 1388 | CE | LYS | A | 392 | 6.545 | 43.004 | 58.726 | 1.00 | 30.06 |
| ATOM | 1389 | CD | LYS | A | 392 | 7.980 | 43.237 | 58.298 | 1.00 | 27.75 |
| ATOM | 1390 | CG | LYS | A | 392 | 8.231 | 44.701 | 57.942 | 1.00 | 25.41 |
| ATOM | 1391 | CB | LYS | A | 392 | 8.133 | 44.929 | 56.460 | 1.00 | 20.56 |
| ATOM | 1392 | CA | LYS | A | 392 | 8.133 | 46.376 | 55.909 | 1.00 | 15.94 |
| ATOM | 1393 | C | LYS | A | 392 | 8.265 | 46.221 | 54.399 | 1.00 | 14.65 |
| ATOM | 1394 | O | LYS | A | 392 | 7.242 | 46.070 | 53.676 | 1.00 | 12.21 |
| ATOM | 1395 | N | THR | A | 393 | 9.481 | 45.969 | 53.965 | 1.00 | 9.88 |
| ATOM | 1396 | CA | THR | A | 393 | 9.744 | 45.629 | 52.574 | 1.00 | 10.28 |
| ATOM | 1397 | CB | THR | A | 393 | 11.178 | 45.988 | 52.156 | 1.00 | 10.31 |
| ATOM | 1398 | OG1 | THR | A | 393 | 11.412 | 47.397 | 52.330 | 1.00 | 9.91 |
| ATOM | 1399 | CG2 | THR | A | 393 | 11.393 | 45.631 | 50.693 | 1.00 | 7.93 |
| ATOM | 1400 | C | THR | A | 393 | 9.450 | 44.139 | 52.450 | 1.00 | 11.39 |
| ATOM | 1401 | O | THR | A | 393 | 9.872 | 43.332 | 53.278 | 1.00 | 11.16 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 1402 N | ILE | A | 394 | 8.715 | 43.737 | 51.398 | 1.00 | 8.47 |
| ATOM | 1403 CA | ILE | A | 394 | 8.413 | 42.305 | 51.297 | 1.00 | 8.59 |
| ATOM | 1404 CB | ILE | A | 394 | 7.223 | 42.076 | 50.329 | 1.00 | 7.43 |
| ATOM | 1405 CG2 | ILE | A | 394 | 6.044 | 42.929 | 50.867 | 1.00 | 5.89 |
| ATOM | 1406 CG1 | ILE | A | 394 | 7.562 | 42.401 | 48.910 | 1.00 | 7.72 |
| ATOM | 1407 CD1 | ILE | A | 394 | 6.413 | 42.268 | 47.877 | 1.00 | 9.17 |
| ATOM | 1408 C | ILE | A | 394 | 9.657 | 41.573 | 50.761 | 1.00 | 9.33 |
| ATOM | 1409 O | ILE | A | 394 | 10.482 | 42.262 | 50.170 | 1.00 | 8.55 |
| ATOM | 1410 N | LEU | A | 395 | 9.689 | 40.276 | 50.913 | 1.00 | 7.97 |
| ATOM | 1411 CA | LEU | A | 395 | 10.808 | 39.499 | 50.347 | 1.00 | 11.81 |
| ATOM | 1412 CB | LEU | A | 395 | 10.545 | 37.998 | 50.620 | 1.00 | 12.21 |
| ATOM | 1413 CG | LEU | A | 395 | 10.370 | 37.651 | 52.090 | 1.00 | 13.09 |
| ATOM | 1414 CD1 | LEU | A | 395 | 10.246 | 36.140 | 52.313 | 1.00 | 10.90 |
| ATOM | 1415 CD2 | LEU | A | 395 | 11.569 | 38.245 | 52.832 | 1.00 | 13.70 |
| ATOM | 1416 C | LEU | A | 395 | 10.920 | 39.603 | 48.860 | 1.00 | 13.57 |
| ATOM | 1417 O | LEU | A | 395 | 9.864 | 39.692 | 48.193 | 1.00 | 11.36 |
| ATOM | 1418 N | THR | A | 396 | 12.089 | 39.426 | 48.281 | 1.00 | 9.31 |
| ATOM | 1419 CA | THR | A | 396 | 12.273 | 39.345 | 46.840 | 1.00 | 11.95 |
| ATOM | 1420 CB | THR | A | 396 | 13.746 | 39.021 | 46.476 | 1.00 | 14.52 |
| ATOM | 1421 OG1 | THR | A | 396 | 14.575 | 40.034 | 47.090 | 1.00 | 16.31 |
| ATOM | 1422 CG2 | THR | A | 396 | 13.983 | 39.148 | 44.996 | 1.00 | 16.49 |
| ATOM | 1423 C | THR | A | 396 | 11.376 | 38.264 | 46.208 | 1.00 | 12.19 |
| ATOM | 1424 O | THR | A | 396 | 10.790 | 38.544 | 45.152 | 1.00 | 11.09 |
| ATOM | 1425 N | LYS | A | 397 | 11.286 | 37.104 | 46.840 | 1.00 | 9.73 |
| ATOM | 1426 CA | LYS | A | 397 | 10.451 | 36.033 | 46.298 | 1.00 | 12.22 |
| ATOM | 1427 CB | LYS | A | 397 | 10.630 | 34.680 | 44.935 | 1.00 | 11.19 |
| ATOM | 1428 CG | LYS | A | 397 | 10.365 | 34.491 | 48.402 | 1.00 | 10.22 |
| ATOM | 1429 CD | LYS | A | 397 | 10.459 | 32.971 | 48.678 | 1.00 | 12.87 |
| ATOM | 1430 CE | LYS | A | 397 | 9.904 | 32.634 | 50.049 | 1.00 | 10.59 |
| ATOM | 1431 NZ | LYS | A | 397 | 10.430 | 31.409 | 50.690 | 1.00 | 13.72 |
| ATOM | 1432 C | LYS | A | 397 | 8.946 | 36.390 | 46.379 | 1.00 | 11.16 |
| ATOM | 1433 O | LYS | A | 397 | 8.250 | 35.937 | 45.488 | 1.00 | 10.09 |
| ATOM | 1434 N | GLU | A | 398 | 8.588 | 37.196 | 47.346 | 1.00 | 10.22 |
| ATOM | 1435 CA | GLU | A | 398 | 7.207 | 37.628 | 47.475 | 1.00 | 13.12 |
| ATOM | 1436 CB | GLU | A | 398 | 6.931 | 38.233 | 48.857 | 1.00 | 11.64 |
| ATOM | 1437 CG | GLU | A | 398 | 6.951 | 37.079 | 49.876 | 1.00 | 15.45 |
| ATOM | 1438 CD | GLU | A | 398 | 6.952 | 37.662 | 51.284 | 1.00 | 15.72 |
| ATOM | 1439 OE1 | GLU | A | 398 | 7.139 | 38.861 | 51.557 | 1.00 | 15.77 |
| ATOM | 1440 OE2 | GLU | A | 398 | 6.722 | 36.861 | 52.186 | 1.00 | 17.81 |
| ATOM | 1441 C | GLU | A | 398 | 6.875 | 38.628 | 46.374 | 1.00 | 14.23 |
| ATOM | 1442 O | GLU | A | 398 | 5.819 | 38.496 | 45.746 | 1.00 | 11.36 |
| ATOM | 1443 N | ALA | A | 399 | 7.791 | 39.566 | 46.144 | 1.00 | 11.71 |
| ATOM | 1444 CA | ALA | A | 399 | 7.603 | 40.571 | 45.121 | 1.00 | 10.93 |
| ATOM | 1445 CB | ALA | A | 399 | 8.705 | 41.611 | 45.021 | 1.00 | 10.46 |
| ATOM | 1446 C | ALA | A | 399 | 7.464 | 39.901 | 43.737 | 1.00 | 11.66 |
| ATOM | 1447 O | ALA | A | 399 | 6.535 | 40.310 | 43.047 | 1.00 | 8.52 |
| ATOM | 1448 N | ASP | A | 400 | 5.259 | 38.892 | 43.411 | 1.00 | 10.58 |
| ATOM | 1449 CA | ASP | A | 400 | 8.092 | 38.272 | 42.164 | 1.00 | 11.27 |
| ATOM | 1450 CB | ASP | A | 400 | 9.061 | 37.001 | 41.994 | 1.00 | 13.33 |
| ATOM | 1451 CG | ASP | A | 400 | 10.525 | 37.443 | 41.936 | 1.00 | 15.25 |
| ATOM | 1452 OD1 | ASP | A | 400 | 10.787 | 38.685 | 41.868 | 1.00 | 11.52 |
| ATOM | 1453 OD2 | ASP | A | 400 | 11.331 | 36.459 | 41.963 | 1.00 | 15.55 |
| ATOM | 1454 C | ASP | A | 400 | 6.682 | 37.543 | 42.061 | 1.00 | 10.74 |
| ATOM | 1455 O | ASP | A | 400 | 6.102 | 37.681 | 40.959 | 1.00 | 11.54 |
| ATOM | 1456 N | LEU | A | 401 | 6.184 | 37.034 | 43.153 | 1.00 | 9.91 |
| ATOM | 1457 CA | LEU | A | 401 | 4.860 | 36.399 | 43.132 | 1.00 | 12.48 |
| ATOM | 1458 CB | LEU | A | 401 | 4.618 | 35.610 | 44.411 | 1.00 | 13.67 |
| ATOM | 1459 CG | LEU | A | 401 | 5.551 | 34.464 | 44.805 | 1.00 | 19.11 |
| ATOM | 1460 CD1 | LEU | A | 401 | 5.596 | 34.451 | 46.337 | 1.00 | 20.83 |
| ATOM | 1461 CD2 | LEU | A | 401 | 5.072 | 33.125 | 44.302 | 1.00 | 19.44 |
| ATOM | 1462 C | LEU | A | 401 | 3.724 | 37.434 | 42.994 | 1.00 | 11.96 |
| ATOM | 1463 O | LEU | A | 401 | 2.701 | 37.092 | 42.388 | 1.00 | 9.62 |
| ATOM | 1464 N | VAL | A | 402 | 3.849 | 38.626 | 43.576 | 1.00 | 9.23 |
| ATOM | 1465 CA | VAL | A | 402 | 2.656 | 39.664 | 43.347 | 1.00 | 10.16 |
| ATOM | 1466 CB | VAL | A | 402 | 3.222 | 40.976 | 44.086 | 1.00 | 11.53 |
| ATOM | 1467 CG1 | VAL | A | 402 | 2.219 | 42.096 | 43.805 | 1.00 | 10.53 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | | 0.000000 | | 0.00000 |
| CRIGX2 | | 0.000000 | | 1.000000 | | | 0.000000 | | 0.00000 |
| CRIGX3 | | 0.000000 | | 0.000000 | | | 1.000000 | | 0.00000 |
| SCALE1 | | 0.016290 | | 0.000000 | | | 0.005111 | | 0.00000 |
| SCALE2 | | 0.000000 | | 0.007919 | | | 0.000000 | | 0.00000 |
| SCALE3 | | 0.000000 | | 0.000000 | | | 0.012896 | | 0.00000 |

| | Atom Type | Residue | ! | # | X | Y | Z | OCC | B |
|---|---|---|---|---|---|---|---|---|---|
| ATOM | 1468 CG2 | VAL | A | 402 | 3.254 | 40.598 | 45.565 | 1.00 | 8.46 |
| ATOM | 1469 C | VAL | A | 402 | 2.701 | 40.016 | 41.882 | 1.00 | 12.23 |
| ATOM | 1470 O | VAL | A | 402 | 1.581 | 40.096 | 41.336 | 1.00 | 9.50 |
| ATOM | 1471 N | THR | A | 403 | 3.821 | 40.359 | 41.261 | 1.00 | 8.92 |
| ATOM | 1472 CA | THR | A | 403 | 3.845 | 40.764 | 39.883 | 1.00 | 8.22 |
| ATOM | 1473 CB | THR | A | 403 | 5.220 | 41.259 | 39.386 | 1.00 | 6.99 |
| ATOM | 1474 OG1 | THR | A | 403 | 5.612 | 42.325 | 40.255 | 1.00 | 6.97 |
| ATOM | 1475 CG2 | THR | A | 403 | 5.221 | 41.841 | 37.998 | 1.00 | 6.87 |
| ATOM | 1476 C | THR | A | 403 | 3.381 | 39.610 | 38.992 | 1.00 | 9.35 |
| ATOM | 1477 O | THR | A | 403 | 2.693 | 39.954 | 38.016 | 1.00 | 5.99 |
| ATOM | 1478 N | THR | A | 404 | 3.855 | 38.407 | 39.301 | 1.00 | 6.34 |
| ATOM | 1479 CA | THR | A | 404 | 3.382 | 37.249 | 38.521 | 1.00 | 7.96 |
| ATOM | 1480 CB | THR | A | 404 | 3.962 | 35.946 | 39.104 | 1.00 | 8.71 |
| ATOM | 1481 OG1 | THR | A | 404 | 5.404 | 35.959 | 38.945 | 1.00 | 8.46 |
| ATOM | 1482 CG2 | THR | A | 404 | 3.448 | 34.743 | 38.303 | 1.00 | 8.11 |
| ATOM | 1483 C | THR | A | 404 | 1.842 | 37.175 | 38.572 | 1.00 | 6.99 |
| ATOM | 1484 O | THR | A | 404 | 1.211 | 36.979 | 37.529 | 1.00 | 6.33 |
| ATOM | 1485 N | HIS | A | 405 | 1.298 | 37.277 | 39.751 | 1.00 | 6.76 |
| ATOM | 1486 CA | HIS | A | 405 | −0.132 | 37.232 | 40.003 | 1.00 | 9.62 |
| ATOM | 1487 CB | HIS | A | 405 | −0.383 | 37.343 | 41.495 | 1.00 | 7.56 |
| ATOM | 1488 CG | HIS | A | 405 | −1.828 | 37.311 | 41.919 | 1.00 | 6.65 |
| ATOM | 1489 CD2 | HIS | A | 405 | −2.801 | 38.292 | 41.862 | 1.00 | 4.31 |
| ATOM | 1490 ND1 | HIS | A | 405 | −2.389 | 36.204 | 42.467 | 1.00 | 7.16 |
| ATOM | 1491 CE1 | HIS | A | 405 | −3.664 | 36.486 | 42.798 | 1.00 | 9.20 |
| ATOM | 1492 NE2 | HIS | A | 405 | −3.937 | 37.722 | 42.413 | 1.00 | 9.52 |
| ATOM | 1493 C | HIS | A | 405 | −0.867 | 38.376 | 39.290 | 1.00 | 9.96 |
| ATOM | 1494 O | HIS | A | 405 | −1.836 | 38.080 | 38.597 | 1.00 | 9.05 |
| ATOM | 1495 N | GLU | A | 406 | −0.414 | 39.612 | 39.416 | 1.00 | 9.09 |
| ATOM | 1496 CA | GLU | A | 406 | −1.106 | 40.730 | 38.755 | 1.00 | 11.72 |
| ATOM | 1497 CB | GLU | A | 406 | −0.532 | 42.078 | 39.207 | 1.00 | 12.02 |
| ATOM | 1498 CG | GLU | A | 406 | −0.582 | 42.239 | 40.701 | 1.00 | 11.63 |
| ATOM | 1499 CD | GLU | A | 406 | −1.940 | 42.013 | 41.321 | 1.00 | 12.61 |
| ATOM | 1500 CE1 | GLU | A | 406 | −2.985 | 42.048 | 40.632 | 1.00 | 12.02 |
| ATOM | 1501 CE2 | GLU | A | 406 | −1.910 | 41.759 | 42.535 | 1.00 | 12.54 |
| ATOM | 1502 C | GLU | A | 406 | −1.087 | 40.659 | 37.256 | 1.00 | 13.24 |
| ATOM | 1503 O | GLU | A | 406 | −2.110 | 40.827 | 36.529 | 1.00 | 10.09 |
| ATOM | 1504 N | LEU | A | 407 | 0.115 | 40.341 | 36.745 | 1.00 | 9.35 |
| ATOM | 1505 CA | LEU | A | 407 | 0.259 | 40.106 | 35.318 | 1.00 | 11.31 |
| ATOM | 1506 CB | LEU | A | 407 | 1.702 | 39.802 | 34.937 | 1.00 | 13.34 |
| ATOM | 1507 CG | LEU | A | 407 | 2.671 | 40.844 | 34.384 | 1.00 | 17.06 |
| ATOM | 1508 CD1 | LEU | A | 407 | 2.232 | 42.279 | 34.412 | 1.00 | 15.35 |
| ATOM | 1509 CD2 | LEU | A | 407 | 4.112 | 40.690 | 34.878 | 1.00 | 15.89 |
| ATOM | 1510 C | LEU | A | 407 | −0.675 | 38.971 | 34.886 | 1.00 | 8.96 |
| ATOM | 1511 O | LEU | A | 407 | −1.105 | 38.869 | 33.720 | 1.00 | 9.09 |
| ATOM | 1512 N | GLY | A | 408 | −0.837 | 37.972 | 35.732 | 1.00 | 7.26 |
| ATOM | 1513 CA | GLY | A | 408 | −1.649 | 36.774 | 35.444 | 1.00 | 7.95 |
| ATOM | 1514 C | GLY | A | 408 | −3.107 | 37.247 | 35.182 | 1.00 | 8.27 |
| ATOM | 1515 O | GLY | A | 408 | −3.776 | 36.757 | 34.277 | 1.00 | 7.64 |
| ATOM | 1516 N | HIS | A | 409 | −3.565 | 38.171 | 36.030 | 1.00 | 10.19 |
| ATOM | 1517 CA | HIS | A | 409 | −4.873 | 38.777 | 35.752 | 1.00 | 11.21 |
| ATOM | 1518 CB | HIS | A | 409 | −5.162 | 39.320 | 36.713 | 1.00 | 8.68 |
| ATOM | 1519 CG | HIS | A | 409 | −5.605 | 39.404 | 38.018 | 1.00 | 10.30 |
| ATOM | 1520 CD2 | HIS | A | 409 | −5.193 | 39.710 | 39.255 | 1.00 | 9.44 |
| ATOM | 1521 ND1 | HIS | A | 409 | −6.606 | 38.454 | 38.114 | 1.00 | 10.06 |
| ATOM | 1522 CE1 | HIS | A | 409 | −6.833 | 38.237 | 39.402 | 1.00 | 12.63 |
| ATOM | 1523 NE2 | HIS | A | 409 | −5.961 | 38.972 | 40.132 | 1.00 | 12.50 |
| ATOM | 1524 C | HIS | A | 409 | −4.918 | 39.414 | 34.381 | 1.00 | 12.04 |
| ATOM | 1525 O | HIS | A | 409 | −5.853 | 39.223 | 33.615 | 1.00 | 12.02 |
| ATOM | 1526 N | ASN | A | 410 | −3.910 | 40.235 | 34.085 | 1.00 | 11.36 |
| ATOM | 1527 CA | ASN | A | 410 | −3.859 | 40.925 | 32.820 | 1.00 | 10.24 |
| ATOM | 1528 CB | ASN | A | 410 | −2.594 | 41.750 | 32.616 | 1.00 | 10.71 |
| ATOM | 1529 CG | ASN | A | 410 | −2.499 | 43.027 | 33.424 | 1.00 | 12.40 |
| ATOM | 1530 OD1 | ASN | A | 410 | −1.369 | 43.394 | 33.748 | 1.00 | 9.72 |
| ATOM | 1531 ND2 | ASN | A | 410 | −3.598 | 43.762 | 33.714 | 1.00 | 9.17 |
| ATOM | 1532 C | ASN | A | 410 | −3.953 | 39.918 | 31.675 | 1.00 | 12.78 |
| ATOM | 1533 O | ASN | A | 410 | −4.538 | 40.276 | 30.652 | 1.00 | 9.40 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 1534 N | PHE | A | 411 | −3.292 | 38.782 | 31.796 | 1.00 | 9.09 |
| ATOM | 1535 CA | PHE | A | 411 | −3.280 | 37.693 | 30.872 | 1.00 | 10.91 |
| ATOM | 1536 CB | PHE | A | 411 | −2.105 | 36.703 | 31.101 | 1.00 | 10.93 |
| ATOM | 1537 CG | PHE | A | 411 | −0.840 | 37.086 | 30.375 | 1.00 | 13.69 |
| ATOM | 1538 CD1 | PHE | A | 411 | −0.102 | 38.216 | 30.730 | 1.00 | 15.12 |
| ATOM | 1539 CD2 | PHE | A | 411 | −0.309 | −36.297 | 29.389 | 1.00 | 15.69 |
| ATOM | 1540 CE1 | PHE | A | 411 | 1.076 | 38.546 | 30.052 | 1.00 | 13.51 |
| ATOM | 1541 CE2 | PHE | A | 411 | 0.862 | 36.617 | 28.723 | 1.00 | 15.64 |
| ATOM | 1542 CZ | PHE | A | 411 | 1.556 | 37.782 | 29.051 | 1.00 | 14.12 |
| ATOM | 1543 C | PHE | A | 411 | −4.606 | 36.903 | 30.849 | 1.00 | 10.27 |
| ATOM | 1544 O | PHE | A | 411 | −4.684 | 36.100 | 29.931 | 1.00 | 9.02 |
| ATOM | 1545 N | GLY | A | 412 | −5.578 | 37.150 | 31.701 | 1.00 | 11.88 |
| ATOM | 1546 CA | GLY | A | 412 | −6.912 | 36.517 | 31.563 | 1.00 | 11.02 |
| ATOM | 1547 C | GLY | A | 412 | −7.360 | 35.734 | 32.748 | 1.00 | 12.85 |
| ATOM | 1548 O | GLY | A | 412 | −8.496 | 35.256 | 32.898 | 1.00 | 11.80 |
| ATOM | 1549 N | ALA | A | 413 | −6.418 | 35.577 | 33.737 | 1.00 | 9.39 |
| ATOM | 1550 CA | ALA | A | 413 | −6.759 | 34.738 | 34.860 | 1.00 | 8.60 |
| ATOM | 1551 CB | ALA | A | 413 | −5.523 | 34.078 | 35.504 | 1.00 | 6.06 |
| ATOM | 1552 C | ALA | A | 413 | −7.520 | 35.451 | 35.966 | 1.00 | 9.94 |
| ATOM | 1553 O | ALA | A | 413 | −7.216 | 36.584 | 36.300 | 1.00 | 9.19 |
| ATOM | 1554 N | GLU | A | 414 | −8.476 | 34.694 | 36.530 | 1.00 | 9.61 |
| ATOM | 1555 CA | GLU | A | 414 | −9.172 | 35.158 | 37.731 | 1.00 | 12.27 |
| ATOM | 1556 CB | GLU | A | 414 | −10.666 | 34.812 | 37.677 | 1.00 | 14.74 |
| ATOM | 1557 CG | GLU | A | 414 | −11.293 | 35.591 | 36.517 | 1.00 | 16.17 |
| ATOM | 1558 CD | GLU | A | 414 | −11.696 | 36.987 | 36.834 | 1.00 | 20.61 |
| ATOM | 1559 OE1 | GLU | A | 414 | −11.520 | 37.544 | 37.933 | 1.00 | 21.11 |
| ATOM | 1560 OE2 | GLU | A | 414 | −12.266 | 37.646 | 35.920 | 1.00 | 24.06 |
| ATOM | 1561 C | GLU | A | 414 | −8.509 | 34.457 | 38.920 | 1.00 | 12.40 |
| ATOM | 1562 O | GLU | A | 414 | −7.455 | 33.841 | 38.757 | 1.00 | 12.29 |
| ATOM | 1563 N | HIS | A | 415 | −9.108 | 34.478 | 40.104 | 1.00 | 11.96 |
| ATOM | 1564 CA | HIS | A | 415 | −8.512 | 33.849 | 41.259 | 1.00 | 13.28 |
| ATOM | 1565 CB | HIS | A | 415 | −9.093 | 34.484 | 43.514 | 1.00 | 12.84 |
| ATOM | 1566 CG | HIS | A | 415 | −8.513 | 35.841 | 42.716 | 1.00 | 11.55 |
| ATOM | 1567 CD2 | HIS | A | 415 | −7.240 | 36.265 | 42.433 | 1.00 | 11.21 |
| ATOM | 1568 ND1 | HIS | A | 415 | −9.180 | 36.899 | 43.276 | 1.00 | 10.77 |
| ATOM | 1569 CE1 | HIS | A | 415 | −8.380 | 37.944 | 43.314 | 1.00 | 9.60 |
| ATOM | 1570 NE2 | HIS | A | 415 | −7.174 | 37.576 | 42.791 | 1.00 | 11.71 |
| ATOM | 1571 C | HIS | A | 415 | −8.789 | 32.362 | 41.293 | 1.00 | 14.34 |
| ATOM | 1572 O | HIS | A | 415 | −9.851 | 32.007 | 40.751 | 1.00 | 10.53 |
| ATOM | 1573 N | ASP | A | 416 | −7.855 | 31.567 | 41.826 | 1.00 | 10.07 |
| ATOM | 1574 CA | ASP | A | 416 | −8.239 | 30.158 | 41.962 | 1.00 | 11.05 |
| ATOM | 1575 CB | ASP | A | 416 | −6.978 | 29.338 | 42.310 | 1.00 | 13.78 |
| ATOM | 1576 CG | ASP | A | 416 | −5.913 | 29.387 | 41.229 | 1.00 | 14.67 |
| ATOM | 1577 OD1 | ASP | A | 416 | −6.267 | 29.373 | 40.039 | 1.00 | 13.81 |
| ATOM | 1578 OD2 | ASP | A | 416 | −4.717 | 29.403 | 41.608 | 1.00 | 16.01 |
| ATOM | 1579 C | ASP | A | 416 | −9.254 | 29.930 | 43.052 | 1.00 | 10.40 |
| ATOM | 1580 O | ASP | A | 416 | −9.169 | 30.468 | 44.159 | 1.00 | 11.17 |
| ATOM | 1581 N | PRO | A | 417 | −10.296 | 29.111 | 42.805 | 1.00 | 10.30 |
| ATOM | 1582 CD | PRO | A | 417 | −10.544 | 28.473 | 41.502 | 1.00 | 12.83 |
| ATOM | 1583 CA | PRO | A | 417 | −11.275 | 28.774 | 43.805 | 1.00 | 12.54 |
| ATOM | 1584 CB | PRO | A | 417 | −12.495 | 28.328 | 42.975 | 1.00 | 13.91 |
| ATOM | 1585 CG | PRO | A | 417 | −11.940 | 27.894 | 41.674 | 1.00 | 15.31 |
| ATOM | 1586 C | PRO | A | 417 | −10.837 | 27.603 | 44.689 | 1.00 | 13.42 |
| ATOM | 1587 O | PRO | A | 417 | −10.002 | 26.839 | 44.276 | 1.00 | 14.77 |
| ATOM | 1588 N | ASP | A | 418 | −11.346 | 27.376 | 45.860 | 1.00 | 14.02 |
| ATOM | 1589 CA | ASP | A | 418 | −11.086 | 26.217 | 46.694 | 1.00 | 20.43 |
| ATOM | 1590 CB | ASP | A | 418 | −11.375 | 26.531 | 48.172 | 1.00 | 22.42 |
| ATOM | 1591 CG | ASP | A | 418 | −10.416 | 27.595 | 48.658 | 1.00 | 25.60 |
| ATOM | 1592 OD1 | ASP | A | 418 | −9.221 | 27.416 | 48.429 | 1.00 | 27.33 |
| ATOM | 1593 OD2 | ASP | A | 418 | −10.724 | 28.666 | 49.204 | 1.00 | 29.81 |
| ATOM | 1594 C | ASP | A | 418 | −11.917 | 25.061 | 46.257 | 1.00 | 23.39 |
| ATOM | 1595 O | ASP | A | 418 | −13.034 | 25.354 | 45.640 | 1.00 | 23.78 |
| ATOM | 1596 N | GLY | A | 419 | −11.533 | 23.829 | 46.307 | 1.00 | 24.01 |
| ATOM | 1597 CA | GLY | A | 419 | −12.290 | 22.650 | 46.050 | 1.00 | 28.51 |
| ATOM | 1598 C | GLY | A | 419 | −12.000 | 21.714 | 44.916 | 1.00 | 31.09 |
| ATOM | 1599 O | GLY | A | 419 | −11.000 | 21.726 | 44.169 | 1.00 | 31.19 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 1600 N | LEU | A | 420 | −12.976 | 20.849 | 44.625 | 1.00 | 32.09 |
| ATOM | 1601 CD2 | LEU | A | 420 | −14.406 | 17.142 | 44.111 | 1.00 | 38.06 |
| ATOM | 1602 CD1 | LEU | A | 420 | −16.571 | 18.444 | 44.050 | 1.00 | 37.27 |
| ATOM | 1603 CG | LEU | A | 420 | −15.061 | 18.507 | 44.238 | 1.00 | 36.91 |
| ATOM | 1604 CB | LEU | A | 420 | −14.424 | 19.470 | 43.224 | 1.00 | 36.82 |
| ATOM | 1605 CA | LEU | A | 420 | −12.969 | 19.843 | 43.591 | 1.00 | 35.26 |
| ATOM | 1606 C | LEU | A | 420 | −12.193 | 20.130 | 42.331 | 1.00 | 36.08 |
| ATOM | 1607 O | LEU | A | 420 | −11.638 | 19.221 | 41.701 | 1.00 | 37.02 |
| ATOM | 1608 N | ALA | A | 421 | −12.053 | 21.380 | 41.907 | 1.00 | 36.27 |
| ATOM | 1609 CB | ALA | A | 421 | −11.478 | 23.254 | 40.472 | 1.00 | 37.17 |
| ATOM | 1610 CA | ALA | A | 421 | −11.309 | 21.755 | 40.742 | 1.00 | 36.49 |
| ATOM | 1611 C | ALA | A | 421 | −9.841 | 21.381 | 40.794 | 1.00 | 35.18 |
| ATOM | 1612 O | ALA | A | 421 | −9.253 | 21.402 | 39.702 | 1.00 | 36.10 |
| ATOM | 1613 N | GLU | A | 422 | −9.183 | 21.102 | 41.907 | 1.00 | 32.65 |
| ATOM | 1614 OE2 | GLU | A | 422 | −8.104 | 20.106 | 37.709 | 1.00 | 41.16 |
| ATOM | 1615 CE1 | GLU | A | 422 | −6.137 | 19.284 | 37.500 | 1.00 | 39.97 |
| ATOM | 1616 CD | GLU | A | 422 | −6.983 | 19.889 | 38.198 | 1.00 | 38.24 |
| ATOM | 1617 CG | GLU | A | 422 | −6.628 | 20.311 | 39.582 | 1.00 | 35.89 |
| ATOM | 1618 CB | GLU | A | 422 | −7.426 | 19.813 | 40.760 | 1.00 | 31.03 |
| ATOM | 1619 CA | GLU | A | 422 | −7.761 | 20.769 | 41.914 | 1.00 | 29.38 |
| ATOM | 1620 C | GLU | A | 422 | −6.901 | 22.028 | 41.779 | 1.00 | 24.25 |
| ATOM | 1621 O | GLU | A | 422 | −5.677 | 21.951 | 42.645 | 1.00 | 21.69 |
| ATOM | 1622 N | CYS | A | 423 | −7.530 | 23.185 | 41.837 | 1.00 | 19.59 |
| ATOM | 1623 CA | CYS | A | 423 | −6.862 | 24.457 | 41.613 | 1.00 | 18.31 |
| ATOM | 1624 CB | CYS | A | 423 | −7.819 | 25.319 | 40.797 | 1.00 | 21.54 |
| ATOM | 1625 SG | CYS | A | 423 | −8.112 | 24.725 | 39.090 | 1.00 | 22.74 |
| ATOM | 1626 C | CYS | A | 423 | −6.367 | 25.102 | 42.893 | 1.00 | 16.82 |
| ATOM | 1627 O | CYS | A | 423 | −5.884 | 26.233 | 42.855 | 1.00 | 14.86 |
| ATOM | 1628 N | ALA | A | 424 | −6.516 | 24.451 | 44.029 | 1.00 | 15.16 |
| ATOM | 1629 CA | ALA | A | 424 | −5.974 | 24.991 | 45.288 | 1.00 | 16.52 |
| ATOM | 1630 CB | ALA | A | 424 | −6.940 | 25.972 | 45.924 | 1.00 | 15.07 |
| ATOM | 1631 C | ALA | A | 424 | −5.603 | 23.812 | 46.165 | 1.00 | 15.42 |
| ATOM | 1632 O | ALA | A | 424 | −6.206 | 23.507 | 47.182 | 1.00 | 16.31 |
| ATOM | 1633 N | PRO | A | 425 | −4.545 | 23.118 | 45.774 | 1.00 | 16.63 |
| ATOM | 1634 CD | PRO | A | 425 | −3.694 | 23.394 | 44.593 | 1.00 | 14.62 |
| ATOM | 1635 CA | PRO | A | 425 | −4.096 | 21.935 | 46.484 | 1.00 | 18.01 |
| ATOM | 1636 CB | PRO | A | 425 | −2.965 | 21.392 | 45.635 | 1.00 | 17.36 |
| ATOM | 1637 CG | PRO | A | 425 | −3.064 | 22.047 | 44.301 | 1.00 | 16.07 |
| ATOM | 1638 C | PRO | A | 425 | −3.655 | 22.217 | 47.908 | 1.00 | 19.52 |
| ATOM | 1639 O | PRO | A | 425 | −3.304 | 23.325 | 48.294 | 1.00 | 16.80 |
| ATOM | 1640 N | ASN | A | 426 | −3.670 | 21.143 | 48.707 | 1.00 | 21.90 |
| ATOM | 1641 ND2 | ASN | A | 426 | −6.177 | 19.346 | 50.674 | 1.00 | 32.22 |
| ATOM | 1642 OD1 | ASN | A | 426 | −5.934 | 21.437 | 51.378 | 1.00 | 30.53 |
| ATOM | 1643 CG | ASN | A | 426 | −5.407 | 20.380 | 51.018 | 1.00 | 30.42 |
| ATOM | 1644 CB | ASN | A | 426 | −3.898 | 20.167 | 50.928 | 1.00 | 27.25 |
| ATOM | 1645 CA | ASN | A | 426 | −3.224 | 21.249 | 50.088 | 1.00 | 24.17 |
| ATOM | 1646 C | ASN | A | 426 | −1.695 | 21.270 | 50.121 | 1.00 | 22.87 |
| ATOM | 1647 O | ASN | A | 426 | −1.014 | 21.025 | 49.127 | 1.00 | 19.72 |
| ATOM | 1648 N | GLU | A | 427 | −1.148 | 21.695 | 51.247 | 1.00 | 24.03 |
| ATOM | 1649 OE2 | GLU | A | 427 | 3.209 | 21.859 | 55.259 | 1.00 | 39.86 |
| ATOM | 1650 OE1 | GLU | A | 427 | 2.503 | 23.818 | 54.605 | 1.00 | 37.70 |
| ATOM | 1651 CD | GLU | A | 427 | 2.640 | 22.595 | 54.427 | 1.00 | 37.41 |
| ATOM | 1652 CG | GLU | A | 427 | 2.167 | 21.979 | 53.132 | 1.00 | 36.42 |
| ATOM | 1653 CB | GLU | A | 427 | 0.679 | 22.110 | 52.857 | 1.00 | 32.16 |
| ATOM | 1654 CA | GLU | A | 427 | 0.305 | 21.775 | 51.409 | 1.00 | 29.42 |
| ATOM | 1655 C | GLU | A | 427 | 0.998 | 20.507 | 50.975 | 1.00 | 29.51 |
| ATOM | 1656 O | GLU | A | 427 | 1.971 | 20.497 | 50.213 | 1.00 | 29.26 |
| ATOM | 1657 N | ASP | A | 428 | 0.488 | 19.358 | 51.414 | 1.00 | 31.72 |
| ATOM | 1658 OD2 | ASP | A | 428 | −1.918 | 16.341 | 52.011 | 1.00 | 41.88 |
| ATOM | 1659 OD1 | ASP | A | 428 | −1.452 | 18.328 | 52.816 | 1.00 | 37.31 |
| ATOM | 1660 CG | ASP | A | 428 | −1.103 | 17.267 | 52.267 | 1.00 | 38.88 |
| ATOM | 1661 CB | ASP | A | 428 | 0.320 | 16.958 | 51.853 | 1.00 | 36.50 |
| ATOM | 1662 CA | ASP | A | 428 | 1.042 | 19.054 | 51.077 | 1.00 | 32.85 |
| ATOM | 1663 C | ASP | A | 428 | 1.081 | 17.735 | 49.610 | 1.00 | 32.15 |
| ATOM | 1664 O | ASP | A | 428 | 1.827 | 16.851 | 49.173 | 1.00 | 32.63 |
| ATOM | 1665 N | GLN | A | 429 | 0.302 | 18.414 | 48.772 | 1.00 | 29.90 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 1666 NE2 | GLN | A | 429 | −0.844 | 15.151 | 46.445 | 1.00 | 35.05 |
| ATOM | 1667 OE1 | GLN | A | 429 | −0.895 | 15.061 | 48.694 | 1.00 | 36.32 |
| ATOM | 1668 CD | GLN | A | 429 | −1.190 | 15.629 | 47.636 | 1.00 | 35.53 |
| ATOM | 1669 CG | GLN | A | 429 | −1.923 | 16.955 | 47.621 | 1.00 | 32.82 |
| ATOM | 1670 CB | GLN | A | 429 | −1.138 | 18.032 | 46.865 | 1.00 | 30.20 |
| ATOM | 1671 CA | GLN | A | 429 | 0.307 | 18.190 | 47.347 | 1.00 | 26.44 |
| ATOM | 1672 C | GLN | A | 429 | 1.041 | 19.302 | 46.621 | 1.00 | 22.82 |
| ATOM | 1673 O | GLN | A | 429 | 0.832 | 19.463 | 45.426 | 1.00 | 21.67 |
| ATOM | 1674 N | GLY | A | 430 | 1.812 | 20.142 | 47.320 | 1.00 | 18.52 |
| ATOM | 1675 CA | GLY | A | 430 | 2.534 | 21.185 | 46.583 | 1.00 | 15.09 |
| ATOM | 1676 C | GLY | A | 430 | 1.982 | 22.581 | 46.889 | 1.00 | 14.53 |
| ATOM | 1677 O | GLY | A | 430 | 2.582 | 23.559 | 46.432 | 1.00 | 16.43 |
| ATOM | 1678 N | GLY | A | 431 | 0.898 | 22.745 | 47.615 | 1.00 | 11.39 |
| ATOM | 1679 CA | GLY | A | 431 | 0.314 | 24.011 | 47.958 | 1.00 | 12.94 |
| ATOM | 1680 C | GLY | A | 431 | −0.505 | 24.702 | 46.871 | 1.00 | 10.35 |
| ATOM | 1681 O | GLY | A | 431 | −0.764 | 24.181 | 45.795 | 1.00 | 11.85 |
| ATOM | 1682 N | LYS | A | 432 | −0.845 | 25.936 | 47.147 | 1.00 | 11.65 |
| ATOM | 1683 CA | LYS | A | 432 | −1.637 | 26.762 | 46.245 | 1.00 | 13.87 |
| ATOM | 1684 CB | LYS | A | 432 | −2.343 | 27.862 | 47.049 | 1.00 | 16.54 |
| ATOM | 1685 CG | LYS | A | 432 | −3.250 | 27.146 | 48.043 | 1.00 | 20.67 |
| ATOM | 1686 CD | LYS | A | 432 | −4.058 | 28.036 | 48.933 | 1.00 | 24.37 |
| ATOM | 1687 CE | LYS | A | 432 | −5.090 | 27.228 | 49.718 | 1.00 | 25.86 |
| ATOM | 1688 NZ | LYS | A | 432 | −4.539 | 25.962 | 50.296 | 1.00 | 25.58 |
| ATOM | 1689 C | LYS | A | 432 | −0.810 | 27.312 | 45.112 | 1.00 | 12.71 |
| ATOM | 1690 O | LYS | A | 432 | 0.414 | 27.398 | 45.187 | 1.00 | 11.37 |
| ATOM | 1691 N | TYR | A | 433 | −1.533 | 27.713 | 44.072 | 1.00 | 8.62 |
| ATOM | 1692 CA | TYR | A | 433 | −0.997 | 28.243 | 42.844 | 1.00 | 8.63 |
| ATOM | 1693 CB | TYR | A | 433 | −1.677 | 27.746 | 41.591 | 1.00 | 0.94 |
| ATOM | 1694 CG | TYR | A | 433 | −1.507 | 26.270 | 41.276 | 1.00 | 12.81 |
| ATOM | 1695 CD1 | TYR | A | 433 | −2.460 | 25.350 | 41.653 | 1.00 | 12.02 |
| ATOM | 1696 CE1 | TYR | A | 433 | −2.310 | 23.995 | 41.361 | 1.00 | 14.63 |
| ATOM | 1697 CD2 | TYR | A | 433 | −0.360 | 25.813 | 40.637 | 1.00 | 13.00 |
| ATOM | 1698 CE2 | TYR | A | 433 | −0.202 | 24.469 | 40.333 | 1.00 | 14.04 |
| ATOM | 1699 CZ | TYR | A | 433 | −1.180 | 23.579 | 40.713 | 1.00 | 15.76 |
| ATOM | 1700 OH | TYR | A | 433 | −1.018 | 22.241 | 40.429 | 1.00 | 18.68 |
| ATOM | 1701 C | TYR | A | 433 | −0.990 | 29.769 | 42.955 | 1.00 | 6.12 |
| ATOM | 1702 O | TYR | A | 433 | −1.576 | 30.319 | 43.866 | 1.00 | 7.36 |
| ATOM | 1703 N | VAL | A | 434 | −0.279 | 30.385 | 42.031 | 1.00 | 8.06 |
| ATOM | 1704 CA | VAL | A | 434 | −0.023 | 33.820 | 42.080 | 1.00 | 9.13 |
| ATOM | 1705 CB | VAL | A | 434 | 1.026 | 32.189 | 41.035 | 1.00 | 9.24 |
| ATOM | 1706 CG1 | VAL | A | 434 | 0.473 | 32.255 | 39.614 | 1.00 | 9.78 |
| ATOM | 1707 CG2 | VAL | A | 434 | 1.656 | 33.531 | 41.432 | 1.00 | 9.67 |
| ATOM | 1708 C | VAL | A | 434 | −1.247 | 32.724 | 41.971 | 1.00 | 9.44 |
| ATOM | 1709 O | VAL | A | 434 | −1.224 | 33.807 | 42.521 | 1.00 | 8.77 |
| ATOM | 1710 N | MET | A | 435 | −2.348 | 32.242 | 41.373 | 1.00 | 9.61 |
| ATOM | 1711 CA | MET | A | 435 | −3.580 | 33.044 | 41.377 | 1.00 | 10.35 |
| ATOM | 1712 CB | MET | A | 435 | −4.313 | 32.866 | 40.054 | 1.00 | 9.92 |
| ATOM | 1713 CG | MET | A | 435 | −3.514 | 33.300 | 38.848 | 1.00 | 10.91 |
| ATOM | 1714 SD | MET | A | 435 | −2.789 | 34.945 | 38.866 | 1.00 | 11.06 |
| ATOM | 1715 CE | MET | A | 435 | −4.229 | 35.954 | 39.266 | 1.00 | 11.66 |
| ATOM | 1716 C | MET | A | 435 | −4.479 | 32.835 | 42.569 | 1.00 | 11.89 |
| ATOM | 1717 O | MET | A | 435 | −5.625 | 33.382 | 42.578 | 1.00 | 10.19 |
| ATOM | 1718 N | TYR | A | 436 | −4.004 | 32.200 | 43.636 | 1.00 | 9.70 |
| ATOM | 1719 CA | TYR | A | 436 | −4.776 | 32.133 | 44.873 | 1.00 | 10.59 |
| ATOM | 1720 CB | TYR | A | 436 | −4.154 | 31.274 | 45.974 | 1.00 | 12.19 |
| ATOM | 1721 CG | TYR | A | 436 | −5.187 | 30.700 | 46.929 | 1.00 | 12.41 |
| ATOM | 1722 CD1 | TYR | A | 436 | −6.086 | 29.710 | 46.528 | 1.00 | 13.54 |
| ATOM | 1723 CE1 | TYR | A | 436 | −7.026 | 29.190 | 47.405 | 1.00 | 10.84 |
| ATOM | 1724 CD2 | TYR | A | 436 | −5.275 | 31.200 | 48.218 | 1.00 | 12.72 |
| ATOM | 1725 CE2 | TYR | A | 436 | −6.216 | 30.710 | 49.104 | 1.00 | 15.95 |
| ATOM | 1726 CZ | TYR | A | 436 | −7.105 | 29.725 | 48.659 | 1.00 | 14.43 |
| ATOM | 1727 OH | TYR | A | 436 | −8.012 | 29.268 | 49.572 | 1.00 | 17.14 |
| ATOM | 1728 C | TYR | A | 436 | −4.977 | 33.571 | 45.304 | 1.00 | 10.80 |
| ATOM | 1729 O | TYR | A | 436 | −4.106 | 34.412 | 45.121 | 1.00 | 7.79 |
| ATOM | 1730 N | PRO | A | 437 | −6.178 | 33.938 | 45.778 | 1.00 | 11.93 |
| ATOM | 1731 CD | PRO | A | 437 | −7.340 | 33.037 | 45.939 | 1.00 | 11.26 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 1732 CA | PRO | A | 437 | −6.467 | 35.326 | 46.139 | 1.00 | 10.62 |
| ATOM | 1733 CB | PRO | A | 437 | −7.962 | 35.319 | 46.495 | 1.00 | 12.25 |
| ATOM | 1734 CG | PRO | A | 437 | −8.320 | 33.884 | 46.714 | 1.00 | 12.44 |
| ATOM | 1735 C | PRO | A | 437 | −5.713 | 35.775 | 47.385 | 1.00 | 10.79 |
| ATOM | 1736 O | PRO | A | 437 | −5.577 | 36.995 | 47.602 | 1.00 | 11.50 |
| ATOM | 1737 N | ILE | A | 438 | −5.411 | 34.802 | 48.243 | 1.00 | 11.06 |
| ATOM | 1738 CA | ILE | A | 438 | −4.645 | 35.046 | 49.464 | 1.00 | 14.21 |
| ATOM | 1739 CB | ILE | A | 438 | −5.154 | 34.201 | 50.625 | 1.00 | 16.10 |
| ATOM | 1740 CG2 | ILE | A | 438 | −4.290 | 34.449 | 51.876 | 1.00 | 19.74 |
| ATOM | 1741 CG1 | ILE | A | 438 | −6.619 | 34.470 | 50.967 | 1.00 | 19.29 |
| ATOM | 1742 CD1 | ILE | A | 438 | −7.175 | 33.545 | 52.055 | 1.00 | 20.13 |
| ATOM | 1743 C | ILE | A | 438 | −3.173 | 34.778 | 49.119 | 1.00 | 14.66 |
| ATOM | 1744 O | ILE | A | 438 | −2.796 | 33.666 | 48.710 | 1.00 | 10.76 |
| ATOM | 1745 N | ALA | A | 439 | −2.342 | 35.803 | 49.202 | 1.00 | 12.90 |
| ATOM | 1746 CB | ALA | A | 439 | −0.137 | 36.968 | 49.129 | 1.00 | 13.51 |
| ATOM | 1747 CA | ALA | A | 439 | −0.946 | 35.702 | 48.748 | 1.00 | 12.56 |
| ATOM | 1748 C | ALA | A | 439 | −0.219 | 34.450 | 49.179 | 1.00 | 11.82 |
| ATOM | 1749 O | ALA | A | 439 | −0.053 | 34.221 | 50.350 | 1.00 | 12.72 |
| ATOM | 1750 N | VAL | A | 440 | 0.244 | 33.624 | 48.232 | 1.00 | 12.54 |
| ATOM | 1751 CA | VAL | A | 440 | 1.038 | 32.460 | 48.610 | 1.00 | 13.18 |
| ATOM | 1752 CB | VAL | A | 440 | 1.194 | 31.545 | 47.405 | 1.00 | 13.89 |
| ATOM | 1753 CG1 | VAL | A | 440 | −0.203 | 30.964 | 47.060 | 1.00 | 14.71 |
| ATOM | 1754 CG2 | VAL | A | 440 | 1.748 | 32.335 | 46.225 | 1.00 | 14.29 |
| ATOM | 1755 C | VAL | A | 440 | 2.422 | 32.915 | 49.105 | 1.00 | 13.24 |
| ATOM | 1756 O | VAL | A | 440 | 2.951 | 33.937 | 48.665 | 1.00 | 10.97 |
| ATOM | 1757 N | SER | A | 441 | 3.009 | 32.117 | 49.958 | 1.00 | 13.77 |
| ATOM | 1758 CA | SER | A | 441 | 4.320 | 32.449 | 50.541 | 1.00 | 15.67 |
| ATOM | 1759 CB | SER | A | 441 | 4.602 | 31.531 | 51.741 | 1.00 | 14.54 |
| ATOM | 1760 OG | SER | A | 441 | 4.895 | 30.230 | 51.251 | 1.00 | 12.13 |
| ATOM | 1761 C | SER | A | 441 | 5.443 | 32.298 | 49.543 | 1.00 | 14.86 |
| ATOM | 1762 O | SER | A | 441 | 6.333 | 33.042 | 49.627 | 1.00 | 16.15 |
| ATOM | 1763 N | GLY | A | 442 | 5.365 | 31.340 | 48.626 | 1.00 | 15.69 |
| ATOM | 1764 CA | GLY | A | 442 | 6.458 | 31.086 | 47.680 | 1.00 | 15.78 |
| ATOM | 1765 C | GLY | A | 442 | 7.329 | 29.955 | 48.292 | 1.00 | 17.87 |
| ATOM | 1766 O | GLY | A | 442 | 8.313 | 29.533 | 47.700 | 1.00 | 17.88 |
| ATOM | 1767 N | ASP | A | 443 | 6.933 | 29.420 | 49.433 | 1.00 | 16.97 |
| ATOM | 1768 CA | ASP | A | 443 | 7.639 | 28.297 | 50.053 | 1.00 | 19.48 |
| ATOM | 1769 CB | ASP | A | 443 | 7.315 | 28.159 | 51.522 | 1.00 | 20.17 |
| ATOM | 1770 CG | ASP | A | 443 | 7.613 | 29.371 | 52.357 | 1.00 | 23.62 |
| ATOM | 1771 OD1 | ASP | A | 443 | 8.296 | 30.306 | 51.896 | 1.00 | 23.81 |
| ATOM | 1772 OD2 | ASP | A | 443 | 7.119 | 29.399 | 53.505 | 1.00 | 25.54 |
| ATOM | 1773 C | ASP | A | 443 | 7.308 | 26.945 | 41.435 | 1.00 | 21.78 |
| ATOM | 1774 O | ASP | A | 443 | 8.052 | 25.962 | 49.619 | 1.00 | 20.22 |
| ATOM | 1775 N | HIS | A | 444 | 6.163 | 26.878 | 48.737 | 1.00 | 18.42 |
| ATOM | 1776 CA | HIS | A | 444 | 5.734 | 25.593 | 48.195 | 1.00 | 18.25 |
| ATOM | 1777 CB | HIS | A | 444 | 4.263 | 25.329 | 48.628 | 1.00 | 19.33 |
| ATOM | 1778 CG | HIS | A | 444 | 4.010 | 25.631 | 50.066 | 1.00 | 21.40 |
| ATOM | 1779 CD2 | HIS | A | 444 | 3.475 | 26.703 | 50.697 | 1.00 | 21.56 |
| ATOM | 1780 ND1 | HIS | A | 444 | 4.407 | 24.766 | 51.066 | 1.00 | 22.82 |
| ATOM | 1781 CE1 | HIS | A | 444 | 4.098 | 25.274 | 52.242 | 1.00 | 22.65 |
| ATOM | 1782 NE2 | HIS | A | 444 | 3.540 | 26.457 | 52.047 | 1.00 | 23.53 |
| ATOM | 1783 C | HIS | A | 444 | 5.869 | 25.478 | 46.699 | 1.00 | 18.20 |
| ATOM | 1784 O | HIS | A | 444 | 5.869 | 26.430 | 45.924 | 1.00 | 16.89 |
| ATOM | 1785 N | GLU | A | 445 | 5.967 | 24.246 | 46.228 | 1.00 | 18.90 |
| ATOM | 1786 OE2 | GLU | A | 445 | 7.287 | 19.466 | 44.909 | 1.00 | 37.32 |
| ATOM | 1787 OE1 | GLU | A | 445 | 5.382 | 19.436 | 43.805 | 1.00 | 36.75 |
| ATOM | 1788 CD | GLU | A | 445 | 6.406 | 20.025 | 44.213 | 1.00 | 34.73 |
| ATOM | 1789 CG | GLU | A | 445 | 6.551 | 21.509 | 43.912 | 1.00 | 31.48 |
| ATOM | 1790 CB | GLU | A | 445 | 5.641 | 22.370 | 44.753 | 1.00 | 24.36 |
| ATOM | 1791 CA | GLU | A | 445 | 6.094 | 23.856 | 44.844 | 1.00 | 21.30 |
| ATOM | 1792 C | GLU | A | 445 | 5.192 | 24.573 | 43.856 | 1.00 | 19.12 |
| ATOM | 1793 O | GLU | A | 445 | 5.654 | 25.106 | 42.852 | 1.00 | 18.41 |
| ATOM | 1794 N | ASN | A | 446 | 3.886 | 24.568 | 44.155 | 1.00 | 14.02 |
| ATOM | 1795 CA | ASN | A | 446 | 2.931 | 25.161 | 43.217 | 1.00 | 12.89 |
| ATOM | 1796 CB | ASN | A | 446 | 1.558 | 24.575 | 43.616 | 1.00 | 13.52 |
| ATOM | 1797 CG | ASN | A | 446 | 1.492 | 23.081 | 43.416 | 1.00 | 11.57 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 1798 OD1 | ASN | A | 446 | 2.288 | 22.530 | 42.688 | 1.00 | 14.69 |
| ATOM | 1799 ND2 | ASN | A | 446 | 0.580 | 22.359 | 44.016 | 1.00 | 14.47 |
| ATOM | 1800 C | ASN | A | 446 | 2.880 | 26.669 | 43.236 | 1.00 | 12.30 |
| ATOM | 1801 O | ASN | A | 446 | 2.299 | 27.295 | 42.349 | 1.00 | 11.18 |
| ATOM | 1802 N | ASN | A | 447 | 3.432 | 27.299 | 44.274 | 1.00 | 12.22 |
| ATOM | 1803 CA | ASN | A | 447 | 3.261 | 28.692 | 44.560 | 1.00 | 12.81 |
| ATOM | 1804 CB | ASN | A | 447 | 3.943 | 29.244 | 45.794 | 1.00 | 13.02 |
| ATOM | 1805 CG | ASN | A | 447 | 3.432 | 28.721 | 47.094 | 1.00 | 14.61 |
| ATOM | 1806 OD1 | ASN | A | 447 | 4.151 | 28.922 | 48.031 | 1.00 | 15.02 |
| ATOM | 1807 ND2 | ASN | A | 447 | 2.276 | 28.070 | 47.103 | 1.00 | 13.05 |
| ATOM | 1808 C | ASN | A | 447 | 3.662 | 29.596 | 43.403 | 1.00 | 14.50 |
| ATOM | 1809 O | ASN | A | 447 | 2.990 | 30.597 | 43.173 | 1.00 | 14.90 |
| ATOM | 1810 N | LYS | A | 448 | 4.698 | 29.182 | 42.678 | 1.00 | 15.41 |
| ATOM | 1811 CA | LYS | A | 448 | 5.123 | 30.032 | 41.582 | 1.00 | 19.44 |
| ATOM | 1812 CB | LYS | A | 448 | 6.678 | 30.007 | 41.496 | 1.00 | 20.29 |
| ATOM | 1813 CG | LYS | A | 448 | 7.319 | 30.599 | 42.725 | 1.00 | 22.70 |
| ATOM | 1814 CD | LYS | A | 448 | 8.503 | 31.527 | 42.408 | 1.00 | 25.96 |
| ATOM | 1815 CE | LYS | A | 448 | 8.285 | 32.968 | 42.835 | 1.00 | 24.34 |
| ATOM | 1816 NZ | LYS | A | 448 | 8.963 | 33.438 | 44.090 | 1.00 | 16.70 |
| ATOM | 1817 C | LYS | A | 448 | 4.568 | 29.566 | 40.271 | 1.00 | 19.62 |
| ATOM | 1818 O | LYS | A | 448 | 5.136 | 29.990 | 39.263 | 1.00 | 25.92 |
| ATOM | 1819 N | MET | A | 449 | 3.632 | 28.647 | 40.230 | 1.00 | 13.54 |
| ATOM | 1820 CA | MET | A | 449 | 3.122 | 28.149 | 38.956 | 1.00 | 14.78 |
| ATOM | 1821 CB | MET | A | 449 | 3.181 | 26.610 | 39.000 | 1.00 | 17.23 |
| ATOM | 1822 CG | MET | A | 449 | 4.638 | 26.182 | 39.231 | 1.00 | 23.71 |
| ATOM | 1823 SD | MET | A | 449 | 5.557 | 26.266 | 37.701 | 1.00 | 35.18 |
| ATOM | 1824 CE | MET | A | 449 | 6.512 | 27.753 | 37.876 | 1.00 | 29.45 |
| ATOM | 1825 C | MET | A | 449 | 1.660 | 28.558 | 38.779 | 1.00 | 10.74 |
| ATOM | 1826 O | MET | A | 449 | 1.051 | 28.898 | 39.776 | 1.00 | 7.03 |
| ATOM | 1827 N | PHE | A | 450 | 1.104 | 28.330 | 37.629 | 1.00 | 9.72 |
| ATOM | 1828 CA | PHE | A | 450 | −0.319 | 28.583 | 37.393 | 1.00 | 11.38 |
| ATOM | 1829 CB | PHE | A | 450 | −0.503 | 29.170 | 35.975 | 1.00 | 11.13 |
| ATOM | 1830 CG | PHE | A | 450 | −0.071 | 30.631 | 35.959 | 1.00 | 12.52 |
| ATOM | 1831 CD1 | PHE | A | 450 | −0.930 | 31.655 | 36.320 | 1.00 | 12.19 |
| ATOM | 1832 CD2 | PHE | A | 450 | 1.207 | 30.955 | 35.549 | 1.00 | 10.84 |
| ATOM | 1833 CE1 | PHE | A | 450 | −0.508 | 32.973 | 36.265 | 1.00 | 11.08 |
| ATOM | 1834 CE2 | PHE | A | 450 | 1.624 | 32.264 | 35.490 | 1.00 | 10.58 |
| ATOM | 1835 CZ | PHE | A | 450 | 0.770 | 33.283 | 35.856 | 1.00 | 10.00 |
| ATOM | 1836 C | PHE | A | 450 | −1.150 | 27.312 | 37.490 | 1.00 | 11.07 |
| ATOM | 1837 O | PHE | A | 450 | −0.799 | 26.260 | 36.954 | 1.00 | 9.07 |
| ATOM | 1838 N | SER | A | 451 | −2.323 | 27.410 | 38.138 | 1.00 | 11.36 |
| ATOM | 1839 CA | SER | A | 451 | −3.268 | 26.315 | 38.270 | 1.00 | 10.14 |
| ATOM | 1840 CB | SER | A | 451 | −4.487 | 26.735 | 39.155 | 1.00 | 10.95 |
| ATOM | 1841 CG | SER | A | 451 | −5.179 | 27.782 | 38.420 | 1.00 | 9.02 |
| ATOM | 1842 C | SER | A | 451 | −3.844 | 25.958 | 36.901 | 1.00 | 9.35 |
| ATOM | 1843 O | SER | A | 451 | −3.770 | 26.735 | 35.963 | 1.00 | 9.40 |
| ATOM | 1844 N | GLN | A | 452 | −4.577 | 24.855 | 36.824 | 1.00 | 12.16 |
| ATOM | 1845 CA | GLN | A | 452 | −5.351 | 24.521 | 35.618 | 1.00 | 13.47 |
| ATOM | 1846 CB | GLN | A | 452 | −5.964 | 23.125 | 35.803 | 1.00 | 16.94 |
| ATOM | 1847 CG | GLN | A | 452 | −6.700 | 22.595 | 34.601 | 1.00 | 21.50 |
| ATOM | 1848 CD | GLN | A | 452 | −5.827 | 22.669 | 33.361 | 1.00 | 23.04 |
| ATOM | 1849 OE1 | GLN | A | 452 | −4.673 | 22.244 | 33.400 | 1.00 | 21.47 |
| ATOM | 1850 NE2 | GLN | A | 452 | −6.377 | 23.285 | 32.307 | 1.00 | 23.25 |
| ATOM | 1851 C | GLN | A | 452 | −6.430 | 25.554 | 35.338 | 1.00 | 33.65 |
| ATOM | 1852 O | GLN | A | 452 | −6.638 | 25.907 | 34.165 | 1.00 | 14.17 |
| ATOM | 1853 N | CYS | A | 453 | −7.045 | 26.104 | 36.363 | 1.00 | 14.02 |
| ATOM | 1854 CA | CYS | A | 453 | −8.092 | 27.127 | 36.197 | 1.00 | 17.31 |
| ATOM | 1855 CB | CYS | A | 453 | −8.719 | 27.417 | 37.560 | 1.00 | 21.49 |
| ATOM | 1856 SG | CYS | A | 453 | −9.533 | 26.093 | 38.447 | 1.00 | 29.58 |
| ATOM | 1857 C | CYS | A | 453 | −7.500 | 28.361 | 35.535 | 1.00 | 15.91 |
| ATOM | 1858 O | CYS | A | 453 | −7.993 | 28.886 | 34.524 | 1.00 | 12.98 |
| ATOM | 1859 N | SER | A | 454 | −6.301 | 28.786 | 36.002 | 1.00 | 10.78 |
| ATOM | 1860 CA | SER | A | 454 | −5.584 | 29.258 | 35.390 | 1.00 | 9.42 |
| ATOM | 1861 CB | SER | A | 454 | −4.341 | 30.410 | 36.146 | 1.00 | 8.01 |
| ATOM | 1862 OG | SER | A | 454 | −4.692 | 30.709 | 37.471 | 1.00 | 8.77 |
| ATOM | 1863 C | SER | A | 454 | −5.186 | 29.538 | 33.979 | 1.00 | 9.67 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | | 0.000000 | | 0.00000 |
| CRIGX2 | | 0.000000 | | 1.000000 | | | 0.000000 | | 0.00000 |
| CRIGX3 | | 0.000000 | | 0.000000 | | | 1.000000 | | 0.00000 |
| SCALE1 | | 0.016290 | | 0.000000 | | | 0.005111 | | 0.00000 |
| SCALE2 | | 0.000000 | | 0.007919 | | | 0.000000 | | 0.00000 |
| SCALE3 | | 0.000000 | | 0.000000 | | | 0.012896 | | 0.00000 |

| | Atom Type | Residue | ! | # | X | Y | Z | OCC | B |
|---|---|---|---|---|---|---|---|---|---|
| ATOM | 1864 O | SER | A | 454 | −5.237 | 30.413 | 33.113 | 1.00 | 9.80 |
| ATOM | 1865 N | LYS | A | 455 | −4.691 | 28.304 | 33.763 | 1.00 | 13.07 |
| ATOM | 1866 CA | LYS | A | 455 | −4.240 | 27.987 | 32.421 | 1.00 | 12.98 |
| ATOM | 1867 CB | LYS | A | 455 | −3.599 | 26.587 | 32.376 | 1.00 | 13.14 |
| ATOM | 1868 CG | LYS | A | 455 | −2.146 | 26.611 | 32.855 | 1.00 | 17.01 |
| ATOM | 1869 CD | LYS | A | 455 | −1.656 | 25.166 | 32.882 | 1.00 | 19.15 |
| ATOM | 1870 CE | LYS | A | 455 | −0.242 | 25.104 | 33.451 | 1.00 | 20.39 |
| ATOM | 1871 NZ | LYS | A | 455 | 0.195 | 23.673 | 33.295 | 1.00 | 23.90 |
| ATOM | 1872 C | LYS | A | 455 | −5.367 | 28.049 | 31.401 | 1.00 | 12.31 |
| ATOM | 1873 O | LYS | A | 455 | −5.180 | 28.539 | 30.315 | 1.00 | 12.74 |
| ATOM | 1874 N | GLN | A | 456 | −6.529 | 27.527 | 31.755 | 1.00 | 14.47 |
| ATOM | 1875 NE2 | GLN | A | 456 | −10.676 | 25.407 | 33.099 | 1.00 | 30.34 |
| ATOM | 1876 OE1 | GLN | A | 456 | −9.503 | 23.500 | 32.899 | 1.00 | 29.79 |
| ATOM | 1877 CD | GLN | A | 456 | −9.664 | 24.686 | 32.606 | 1.00 | 28.31 |
| ATOM | 1878 CG | GLN | A | 456 | −8.670 | 25.342 | 31.686 | 1.00 | 25.00 |
| ATOM | 1879 CB | GLN | A | 456 | −8.814 | 26.832 | 31.511 | 1.00 | 19.95 |
| ATOM | 1880 CA | GLN | A | 456 | −7.661 | 27.516 | 30.804 | 1.00 | 16.41 |
| ATOM | 1881 C | GLN | A | 456 | −7.967 | 28.542 | 30.401 | 1.00 | 15.24 |
| ATOM | 1882 O | GLN | A | 456 | −7.936 | 29.330 | 29.244 | 1.00 | 15.99 |
| ATOM | 1883 N | SER | A | 457 | −8.038 | 29.821 | 31.393 | 1.00 | 14.14 |
| ATOM | 1884 CA | SER | A | 457 | −8.377 | 31.231 | 33.194 | 1.00 | 14.81 |
| ATOM | 1885 CB | SER | A | 457 | −8.518 | 31.976 | 32.530 | 1.00 | 15.12 |
| ATOM | 1886 OG | SER | A | 457 | −9.565 | 31.464 | 33.315 | 1.00 | 16.45 |
| ATOM | 1887 C | SER | A | 457 | −7.354 | 31.967 | 30.377 | 1.00 | 12.94 |
| ATOM | 1888 O | SER | A | 457 | −7.697 | 32.696 | 29.467 | 1.00 | 12.19 |
| ATOM | 1889 N | ILE | A | 458 | −6.051 | 31.825 | 30.722 | 1.00 | 12.21 |
| ATOM | 1890 CA | ILE | A | 458 | −5.038 | 32.567 | 29.982 | 1.00 | 9.86 |
| ATOM | 1891 CB | ILE | A | 458 | −3.699 | 32.500 | 30.795 | 1.00 | 11.36 |
| ATOM | 1892 CG2 | ILE | A | 548 | −2.555 | 32.898 | 29.890 | 1.00 | 6.36 |
| ATOM | 1893 CG1 | ILE | A | 458 | −3.853 | 33.384 | 32.036 | 1.00 | 9.88 |
| ATOM | 1894 CD1 | ILE | A | 458 | −2.730 | 33.281 | 33.059 | 1.00 | 11.89 |
| ATOM | 1895 C | ILE | A | 458 | −4.854 | 32.048 | 28.573 | 1.00 | 9.53 |
| ATOM | 1896 O | ILE | A | 458 | −4.640 | 32.816 | 27.634 | 1.00 | 9.61 |
| ATOM | 1897 N | TYR | A | 459 | −4.939 | 30.731 | 28.423 | 1.00 | 9.48 |
| ATOM | 1898 CA | TYR | A | 459 | −4.767 | 30.100 | 27.112 | 1.00 | 11.60 |
| ATOM | 1899 CB | TYR | A | 459 | −5.038 | 28.600 | 27.250 | 1.00 | 11.22 |
| ATOM | 1900 CG | TYR | A | 459 | −5.045 | 27.843 | 25.943 | 1.00 | 16.31 |
| ATOM | 1901 CD1 | TYR | A | 459 | −4.013 | 27.976 | 25.041 | 1.00 | 16.99 |
| ATOM | 1902 CE1 | TYR | A | 459 | −4.028 | 27.303 | 23.827 | 1.00 | 19.40 |
| ATOM | 1903 CD2 | TYR | A | 459 | −6.103 | 26.999 | 25.626 | 1.00 | 18.93 |
| ATOM | 1904 CE2 | TYR | A | 459 | −6.108 | 26.299 | 24.422 | 1.00 | 21.51 |
| ATOM | 1905 CZ | TYR | A | 459 | −5.075 | 26.458 | 23.532 | 1.00 | 20.71 |
| ATOM | 1906 OH | TYR | A | 459 | −5.095 | 25.772 | 22.341 | 1.00 | 21.74 |
| ATOM | 1907 C | TYR | A | 459 | −5.720 | 30.750 | 26.110 | 1.00 | 12.72 |
| ATOM | 1908 O | TYR | A | 459 | −5.334 | 31.252 | 25.073 | 1.00 | 14.82 |
| ATOM | 1909 N | LYS | A | 460 | −6.974 | 30.779 | 26.528 | 1.00 | 14.14 |
| ATOM | 1910 NZ | LYS | A | 460 | −10.468 | 26.961 | 25.743 | 1.00 | 30.41 |
| ATOM | 1911 CE | LYS | A | 460 | −9.733 | 27.718 | 24.702 | 1.00 | 27.82 |
| ATOM | 1912 CD | LYS | A | 460 | −9.809 | 29.219 | 24.921 | 1.00 | 26.35 |
| ATOM | 1913 CG | LYS | A | 460 | −9.794 | 29.689 | 26.345 | 1.00 | 23.26 |
| ATOM | 1914 CB | LYS | A | 460 | −9.375 | 31.156 | 26.477 | 1.00 | 19.80 |
| ATOM | 1915 CA | LYS | A | 460 | −8.043 | 31.371 | 25.721 | 1.00 | 18.07 |
| ATOM | 1916 C | LYS | A | 460 | −7.739 | 32.806 | 25.384 | 1.00 | 16.65 |
| ATOM | 1917 O | LYS | A | 460 | −7.735 | 33.206 | 24.228 | 1.00 | 16.84 |
| ATOM | 1918 N | THR | A | 461 | −7.225 | 33.546 | 26.348 | 1.00 | 14.44 |
| ATOM | 1919 CA | THR | A | 461 | −6.847 | 34.932 | 26.139 | 1.00 | 14.79 |
| ATOM | 1920 CB | THR | A | 461 | −6.597 | 35.590 | 27.509 | 1.00 | 13.79 |
| ATOM | 1921 OG1 | THR | A | 461 | −7.813 | 35.528 | 28.254 | 1.00 | 13.87 |
| ATOM | 1922 CG2 | THR | A | 461 | −6.192 | 37.054 | 27.345 | 1.00 | 16.01 |
| ATOM | 1923 C | THR | A | 461 | −5.709 | 35.061 | 25.159 | 1.00 | 14.88 |
| ATOM | 1924 O | THR | A | 461 | −5.830 | 35.765 | 24.142 | 1.00 | 14.86 |
| ATOM | 1925 N | ILE | A | 462 | −4.569 | 34.417 | 25.419 | 1.00 | 14.52 |
| ATOM | 1926 CA | ILE | A | 462 | −3.422 | 34.528 | 24.542 | 1.00 | 17.34 |
| ATOM | 1927 CB | ILE | A | 462 | −2.223 | 33.642 | 24.975 | 1.00 | 18.43 |
| ATOM | 1928 CG2 | ILE | A | 462 | −1.130 | 33.699 | 23.904 | 1.00 | 20.28 |
| ATOM | 1929 CG1 | ILE | A | 462 | −1.643 | 34.018 | 26.316 | 1.00 | 18.70 |

TABLE 1-continued

REMARK Created by MOLEMAN V. 961218/7.2.5 at Fri Sep 19 20:05:05 1997 for user carlos
REMARK Moleman FDS file

| | | | | | | | | | |
|---|---|---|---|---|---|---|---|---|---|
| CRYST1 | 61.387 | 126.278 | 81.273 | 90.00 | 107.42 | 90.00 | P 21 | 4 | |
| CRIGX1 | | 1.000000 | | 0.000000 | | 0.000000 | | 0.00000 | |
| CRIGX2 | | 0.000000 | | 1.000000 | | 0.000000 | | 0.00000 | |
| CRIGX3 | | 0.000000 | | 0.000000 | | 1.000000 | | 0.00000 | |
| SCALE1 | | 0.016290 | | 0.000000 | | 0.005111 | | 0.00000 | |
| SCALE2 | | 0.000000 | | 0.007919 | | 0.000000 | | 0.00000 | |
| SCALE3 | | 0.000000 | | 0.000000 | | 0.012896 | | 0.00000 | |

| | Atom Type | Residue | ! | # | X | Y | Z | OCC | B |
|---|---|---|---|---|---|---|---|---|---|
| ATOM | 1930 CD1 | ILE | A | 462 | −0.726 | 32.967 | 26.946 | 1.00 | 19.10 |
| ATOM | 1931 C | ILE | A | 462 | −3.757 | 34.102 | 23.124 | 1.00 | 18.59 |
| ATOM | 1932 O | ILE | A | 462 | −3.420 | 34.813 | 22.189 | 1.00 | 17.11 |
| ATOM | 1933 N | GLU | A | 463 | −4.473 | 32.979 | 22.968 | 1.00 | 22.82 |
| ATOM | 1934 OE2 | GLU | A | 463 | −8.026 | 23.422 | 22.532 | 1.00 | 41.03 |
| ATOM | 1935 OE1 | GLU | A | 463 | −7.006 | 28.787 | 20.674 | 1.00 | 39.73 |
| ATOM | 1936 CD | GLU | A | 463 | −7.293 | 29.635 | 21.536 | 1.00 | 39.22 |
| ATOM | 1937 CG | GLU | A | 463 | −6.723 | 31.032 | 21.405 | 1.00 | 36.15 |
| ATOM | 1938 CB | GLU | A | 463 | −5.228 | 31.095 | 21.624 | 1.00 | 30.56 |
| ATOM | 1939 CA | GLU | A | 463 | −4.692 | 32.520 | 21.587 | 1.00 | 26.30 |
| ATOM | 1940 C | GLU | A | 463 | −5.492 | 33.530 | 20.800 | 1.00 | 27.72 |
| ATOM | 1941 O | GLU | A | 463 | −5.233 | 33.704 | 19.607 | 1.00 | 29.03 |
| ATOM | 1942 N | SER | A | 464 | −6.399 | 34.283 | 23.418 | 1.00 | 26.79 |
| ATOM | 1943 CA | SER | A | 464 | −7.190 | 35.312 | 20.764 | 1.00 | 26.80 |
| ATOM | 1944 CB | SER | A | 464 | −8.395 | 35.611 | 21.666 | 1.00 | 25.15 |
| ATOM | 1945 OG | SER | A | 464 | −9.060 | 36.806 | 21.404 | 1.00 | 25.60 |
| ATOM | 1946 C | SER | A | 464 | −6.434 | 36.623 | 20.582 | 1.00 | 27.79 |
| ATOM | 1947 O | SER | A | 464 | −6.686 | 37.340 | 19.612 | 1.00 | 27.52 |
| ATOM | 1948 N | LYS | A | 465 | −5.598 | 36.959 | 21.560 | 1.00 | 25.83 |
| ATOM | 1949 CA | LYS | A | 465 | −4.956 | 38.267 | 21.585 | 1.00 | 28.04 |
| ATOM | 1950 CB | LYS | A | 465 | −5.065 | 38.846 | 22.993 | 1.00 | 28.65 |
| ATOM | 1951 CG | LYS | A | 465 | −6.217 | 39.766 | 23.316 | 1.00 | 30.43 |
| ATOM | 1952 CD | LYS | A | 465 | −7.570 | 39.136 | 23.099 | 1.00 | 31.72 |
| ATOM | 1953 CE | LYS | A | 465 | −8.699 | 40.165 | 23.068 | 1.00 | 32.17 |
| ATOM | 1954 NZ | LYS | A | 465 | −8.593 | 41.165 | 24.149 | 1.00 | 32.20 |
| ATOM | 1955 C | LYS | A | 465 | −3.505 | 38.293 | 21.145 | 1.00 | 27.28 |
| ATOM | 1956 O | LYS | A | 465 | −3.053 | 39.353 | 20.704 | 1.00 | 27.45 |
| ATOM | 1957 N | ALA | A | 466 | −2.767 | 37.193 | 21.184 | 1.00 | 28.49 |
| ATOM | 1958 CA | ALA | A | 466 | −1.373 | 37.191 | 20.753 | 1.00 | 28.95 |
| ATOM | 1959 CB | ALA | A | 466 | −0.788 | 35.788 | 20.750 | 1.00 | 27.44 |
| ATOM | 1960 C | ALA | A | 466 | −1.152 | 37.821 | 19.385 | 1.00 | 30.12 |
| ATOM | 1961 O | ALA | A | 466 | −0.295 | 38.708 | 19.256 | 1.00 | 28.37 |
| ATOM | 1962 N | GLN | A | 467 | −1.922 | 37.440 | 18.373 | 1.00 | 30.63 |
| ATOM | 1963 NE2 | GLN | A | 467 | 0.360 | 36.582 | 14.061 | 1.00 | 41.77 |
| ATOM | 1964 OE1 | GLN | A | 467 | −0.196 | 35.394 | 15.846 | 1.00 | 42.22 |
| ATOM | 1965 CD | GLN | A | 467 | −0.524 | 36.191 | 14.967 | 1.00 | 40.84 |
| ATOM | 1966 CG | GLN | A | 467 | −1.903 | 36.768 | 14.813 | 1.00 | 40.14 |
| ATOM | 1967 CB | GLN | A | 467 | −2.609 | 37.306 | 16.027 | 1.00 | 36.55 |
| ATOM | 1968 CA | GLN | A | 467 | −1.712 | 38.007 | 17.038 | 1.00 | 33.94 |
| ATOM | 1969 C | GLN | A | 467 | −1.891 | 39.519 | 16.994 | 1.00 | 33.19 |
| ATOM | 1970 O | GLN | A | 467 | −1.208 | 40.231 | 16.271 | 1.00 | 33.32 |
| ATOM | 1971 N | GLU | A | 468 | −2.797 | 40.063 | 17.768 | 1.00 | 33.44 |
| ATOM | 1972 OE2 | GLU | A | 468 | −7.657 | 40.802 | 18.969 | 1.00 | 44.61 |
| ATOM | 1973 OE1 | GLU | A | 468 | −6.465 | 41.900 | 20.497 | 1.00 | 44.24 |
| ATOM | 1974 CD | GLU | A | 468 | −6.664 | 41.480 | 19.332 | 1.00 | 44.10 |
| ATOM | 1975 CG | GLU | A | 468 | −5.602 | 41.832 | 18.305 | 1.00 | 41.64 |
| ATOM | 1976 CB | GLU | A | 468 | −4.238 | 41.582 | 18.934 | 1.00 | 38.28 |
| ATOM | 1977 CA | GLU | A | 468 | −3.092 | 41.457 | 17.917 | 1.00 | 35.15 |
| ATOM | 1978 C | GLU | A | 468 | −1.956 | 42.299 | 18.485 | 1.00 | 33.88 |
| ATOM | 1979 O | GLU | A | 468 | −1.706 | 43.397 | 17.980 | 1.00 | 32.88 |
| ATOM | 1980 N | CYS | A | 469 | −1.382 | 41.873 | 19.618 | 1.00 | 32.54 |
| ATOM | 1981 CA | CYS | A | 469 | −0.374 | 42.738 | 20.230 | 1.00 | 32.43 |
| ATOM | 1982 CB | CYS | A | 469 | −1.019 | 43.591 | 21.320 | 1.00 | 34.38 |
| ATOM | 1983 SG | CYS | A | 469 | −1.294 | 42.874 | 22.918 | 1.00 | 36.46 |
| ATOM | 1984 C | CYS | A | 469 | 0.888 | 42.055 | 20.713 | 1.00 | 29.85 |
| ATOM | 1985 O | CYS | A | 469 | 1.786 | 42.811 | 21.105 | 1.00 | 30.62 |
| ATOM | 1986 N | PHE | A | 470 | 1.027 | 40.739 | 20.624 | 1.00 | 26.22 |
| ATOM | 1987 CA | PHE | A | 470 | 2.314 | 40.147 | 21.073 | 1.00 | 25.07 |
| ATOM | 1988 CB | PHE | A | 470 | 2.163 | 38.694 | 21.471 | 1.00 | 21.88 |
| ATOM | 1989 CG | PHE | A | 470 | 1.492 | 38.480 | 22.808 | 1.00 | 21.60 |
| ATOM | 1990 CD1 | PHE | A | 470 | 0.810 | 39.497 | 23.450 | 1.00 | 19.78 |
| ATOM | 1991 CD2 | PHE | A | 470 | 1.556 | 37.251 | 23.414 | 1.00 | 19.41 |
| ATOM | 1992 CE1 | PHE | A | 470 | 0.182 | 39.309 | 24.658 | 1.00 | 20.26 |
| ATOM | 1993 CE2 | PHE | A | 470 | 0.932 | 37.046 | 24.634 | 1.00 | 20.13 |
| ATOM | 1994 CZ | PHE | A | 470 | 0.257 | 38.065 | 25.257 | 1.00 | 20.62 |
| ATOM | 1995 C | PHE | A | 470 | 3.351 | 40.383 | 19.999 | 1.00 | 24.85 |

TABLE 1-continued

REMARK Created by MOLEMAN V. 961218/7.2.5 at Fri Sep 19 20:05:05 1997 for user carlos
REMARK Moleman FDS file

| CRYST1 | 61.387 | 126.278 | 81.273 | 90.00 | 107.42 | 90.00 | P 21 | 4 | |
|---|---|---|---|---|---|---|---|---|---|
| CRIGX1 | | 1.000000 | | 0.000000 | | | 0.000000 | | 0.00000 |
| CRIGX2 | | 0.000000 | | 1.000000 | | | 0.000000 | | 0.00000 |
| CRIGX3 | | 0.000000 | | 0.000000 | | | 1.000000 | | 0.00000 |
| SCALE1 | | 0.016290 | | 0.000000 | | | 0.005111 | | 0.00000 |
| SCALE2 | | 0.000000 | | 0.007919 | | | 0.000000 | | 0.00000 |
| SCALE3 | | 0.000000 | | 0.000000 | | | 0.012896 | | 0.00000 |

| | Atom Type | Residue | ! | # | X | Y | Z | OCC | B |
|---|---|---|---|---|---|---|---|---|---|
| ATOM | 1996 O | PHE | A | 470 | 2.994 | 40.592 | 18.836 | 1.00 | 23.37 |
| ATOM | 1997 N | GLN | A | 471 | 4.610 | 40.404 | 20.389 | 1.00 | 23.76 |
| ATOM | 1998 CA | GLN | A | 471 | 5.714 | 40.672 | 19.491 | 1.00 | 25.96 |
| ATOM | 1999 CB | GLN | A | 471 | 6.350 | 42.028 | 19.794 | 1.00 | 27.26 |
| ATOM | 2000 CG | GLN | A | 471 | 5.453 | 43.201 | 19.442 | 1.00 | 31.81 |
| ATOM | 2001 CD | GLN | A | 471 | 6.014 | 44.575 | 19.678 | 1.00 | 33.37 |
| ATOM | 2002 OE1 | GLN | A | 471 | 5.258 | 45.547 | 19.668 | 1.00 | 35.13 |
| ATOM | 2003 NE2 | GLN | A | 471 | 7.323 | 44.723 | 19.885 | 1.00 | 35.41 |
| ATOM | 2004 C | GLN | A | 471 | 6.772 | 39.578 | 19.615 | 1.00 | 25.85 |
| ATOM | 2005 O | GLN | A | 471 | 6.668 | 38.670 | 20.433 | 1.00 | 23.32 |
| ATOM | 2006 N | GLU | A | 472 | 7.771 | 39.683 | 18.760 | 1.00 | 27.21 |
| ATOM | 2007 OE2 | GLU | A | 472 | 8.898 | 41.817 | 17.307 | 1.00 | 43.27 |
| ATOM | 2008 OE1 | GLU | A | 472 | 9.685 | 41.624 | 15.282 | 1.00 | 44.72 |
| ATOM | 2009 CD | GLU | A | 472 | 9.267 | 41.115 | 16.344 | 1.00 | 42.17 |
| ATOM | 2010 CG | GLU | A | 472 | 9.207 | 39.605 | 16.387 | 1.00 | 39.41 |
| ATOM | 2011 CB | GLU | A | 472 | 9.836 | 38.975 | 17.600 | 1.00 | 34.14 |
| ATOM | 2012 CA | GLU | A | 472 | 8.867 | 38.730 | 18.759 | 1.00 | 30.87 |
| ATOM | 2013 C | GLU | A | 472 | 9.656 | 38.993 | 20.037 | 1.00 | 30.26 |
| ATOM | 2014 O | GLU | A | 472 | 9.773 | 40.161 | 20.396 | 1.00 | 29.23 |
| ATOM | 2015 N | ARG | A | 473 | 10.256 | 37.970 | 20.584 | 1.00 | 31.97 |
| ATOM | 2016 CA | ARG | A | 473 | 11.073 | 38.106 | 21.778 | 1.00 | 34.21 |
| ATOM | 2017 CB | ARG | A | 473 | 11.230 | 36.691 | 22.340 | 1.00 | 34.97 |
| ATOM | 2018 CG | ARG | A | 473 | 12.230 | 36.454 | 23.443 | 1.00 | 37.52 |
| ATOM | 2019 CD | ARG | A | 473 | 11.661 | 35.449 | 24.436 | 1.00 | 39.68 |
| ATOM | 2020 NE | ARG | A | 473 | 12.564 | 35.155 | 25.532 | 1.00 | 41.06 |
| ATOM | 2021 CZ | ARG | A | 473 | 12.469 | 35.726 | 26.729 | 1.00 | 42.18 |
| ATOM | 2022 NH1 | ARG | A | 473 | 13.327 | 35.423 | 27.693 | 1.00 | 42.83 |
| ATOM | 2023 NH2 | ARG | A | 473 | 11.559 | 36.660 | 26.960 | 1.00 | 42.33 |
| ATOM | 2024 C | ARG | A | 473 | 12.451 | 38.665 | 21.456 | 1.00 | 36.39 |
| ATOM | 2025 O | ARG | A | 473 | 13.092 | 38.294 | 20.489 | 1.00 | 36.44 |
| ATOM | 2026 N | SER | A | 474 | 12.918 | 39.567 | 22.276 | 1.00 | 37.92 |
| ATOM | 2027 OG | SER | A | 474 | 15.308 | 38.413 | 23.524 | 1.00 | 36.38 |
| ATOM | 2028 CB | SER | A | 474 | 15.293 | 39.122 | 22.290 | 1.00 | 37.61 |
| ATOM | 2029 CA | SER | A | 474 | 14.200 | 40.202 | 22.359 | 1.00 | 37.96 |
| ATOM | 2030 C | SER | A | 474 | 14.436 | 41.341 | 21.403 | 1.00 | 39.67 |
| ATOM | 2031 O | SER | A | 474 | 13.589 | 42.259 | 21.336 | 1.00 | 40.16 |

END

EXAMPLE 5
TACE Inhibitor Design

The TACE x-ray diffraction coordinates were read into a Sybyl v.6.3 (Tripos Associates) software package and the x-ray structure analyzed graphically. The regions within the original x-ray coordinates were corrected for chirality and atom type. The modified x-ray model of TACE was energy minimized until all the TACE structural parameters were at their equilibrium or optimal values. The energy minimized structure was then compared to the original structure to confirm the absence of anomalies.

Sites of specific interaction(s) between TACE and the co-crystallized inhibitor were identified. The inhibitor was then removed from the X-ray complex model, leaving only the TACE structural model.

Candidate inhibitors were chosen based upon the sites of interaction with TACE and the candidate inhibitor in light of the sites of interaction identified previously for the co-crystallized inhibitor. Once specific candidate inhibitor-TACE interactions were determined, docking studies were performed to provide preliminary "modeled" complexes of selected candidate inhibitors with TACE.

Constrained conformational analysis was performed using molecular dynamics (MD) to check the integrity of the modeled TACE-inhibitor complex. Once the complex reached its most favorable conformational state, the structure as proposed by the MD study was analyzed visually to insure that the modeled complex complied with known experimental SAR/QSAR based on measured binding affinities.

The modeled candidate inhibitor-TACE complex was analyzed. The region of the complex associated with the S1' regions of TACE containing a small solvent exposed channel was chosen as a target region for modification. A single modification, a benzyl group which becomes embedded within the target region, was selected based upon computational and synthetic chemical principles. The benzyl group was oriented on an appropriate zinc chelator core so as to be projected into the S1'S3' pocket. This modification converts an inhibitor which was generally MMP selective to one which is TACE selective. IC50 data for the inhibitor with a benzyl modification confirm this selectivity.

Structure-based analoging for optimization of inhibitor potency, selectivity and physical drug-like properties was performed in an iterative manner.

EXAMPLE 6

Measuring TACE Inhibition

250 μM peptide substrate (Ac-SPLAQAVRSSSR-NH$_2$) was incubate with 3.7 U/μL TACE in a buffer containing 10 mM TRIS HCl, pH 7.4, 10% glycerol at 25 degrees C. The reaction was quenched with 1% TFA (final concentration) after two hours. The reaction mixture was separated by HPLC on a Hewlett-Packard 1150. The product formation was monitored by absorbance at 220 nm.

The linearity of the reaction was confirmed ($r^2>0.85$). The mean (x±sem) of the control rate was calculated and compared for statistical significance (p<0.05) with drug-tested rates using Dunnett's multiple comparison test. Dose-response relationships were generated using multiple doses of drug and IC$_{50}$ values with 95% CI were estimated using linear regression.

From the foregoing description and examples, one skilled in the art can ascertain the essential characteristics of the invention and, without departing from the spirit and scope of the invention, can make changes, modifications, and variations of the invention to adapt it to various uses and conditions. Additionally, the disclosure of all publications and patent applications cited above, including U.S. provisional patent application serial No. 60/073,709 and U.S. provisional patent application serial No. 60/135,499, are expressly incorporated herein by reference in their entireties to the same extent as if each were incorporated by reference individually.

What we claim is:

1. A method of identifying a compound that associates with tumor necrosis factor-α-converting enzyme (TACE), comprising (A) using atomic coordinates that comprise the coordinates of Table 1 to design an associating compound that forms a bond with a catalytic domain of a TACE polypeptide, (B) synthesizing said compound, and (C) determining in vitro whether said compound associates with said catalytic domain and whether said compound inhibits, meditates, or otherwise regulates TNF-α-converting enzyme activity.

2. The method according to claim 1, wherein said associating compound is an inhibitor, mediator, or other compound that regulates TNF-α-converting enzyme activity.

3. The method of claim 1, wherein said associating compound is a competitive inhibitor, un-competitive inhibitor, or non-competitive inhibitor.

4. The method according to claim 1, wherein the associating compound is designed to incorporate a moiety that chelates zinc.

5. The method according to claim 1, wherein the associating compound is designed to associate with the S1' region of TNF-α-converting enzyme.

6. The method according to claim 1, wherein the associating compound is designed to associate with the S1'S3' pocket of TNF-α-converting enzyme.

7. The method according to claim 1, wherein the associating compound is designed to introduce a non-polar group which occupies the S1' pocket of TNF-α-converting enzyme.

8. The method according to claim 1, wherein the associating compound is designed to introduce a group which lies within the channel joining S1'–S3' pockets of TNF-α-converting enzyme and which makes appropriate van der Waal contact with the channel.

9. The method according to claim 1, wherein the associating compound is designed to form a hydrogen bond with Leu348 or Gly349 of TNF-α-converting enzyme.

10. The method according to claim 1, wherein the associating compound is designed to form a hydrogen bond with Leu348 or Gly349 on the backbone amide groups of TNF-α-converting enzyme.

* * * * *

```
                     SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 1:

Pro Leu Ala Gln Ala Val Arg Ser Ser Ser
1               5                   10

(2) INFORMATION FOR SEQ ID NO: 2:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Gly Ser His His His His His His
1               5

(2) INFORMATION FOR SEQ ID NO: 3:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

His Glu Xaa Xaa His Xaa Xaa Gly Xaa Xaa His
1               5                   10

(2) INFORMATION FOR SEQ ID NO: 4:

(i) SEQUENCE CHARACTERISTICS:
        (A) LENGTH: 203 amino acids
```

```
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 4:

Glu Gln Asn Leu Pro Gln Arg Tyr Ile Glu Leu Val Val Ala Asp
1               5                  10                  15

Arg Arg Val Phe Met Lys Tyr Asn Ser Asp Leu Asn Ile Ile Arg Thr
            20                  25                  30

Arg Val His Glu Ile Val Asn Ile Ile Asn Glu Phe Tyr Arg Ser Leu
            35                  40                  45

Asn Ile Arg Val Ser Leu Thr Asp Leu Glu Ile Trp Ser Gly Gln Asp
50                  55                  60

Phe Ile Thr Ile Gln Ser Ser Ser Asn Thr Leu Asn Ser Phe Gly
65                  70                  75                  80

Glu Trp Arg Glu Arg Val Leu Leu Thr Arg Lys Arg His Asp Asn Ala
            85                  90                  95

Gln Leu Leu Thr Ala Ile Asn Phe Glu Gly Lys Ile Ile Gly Lys Ala
            100                 105                 110

Tyr Thr Ser Ser Met Cys Asn Pro Arg Ser Ser Val Gly Ile Val Lys
        115                 120                 125

Asp His Ser Pro Ile Asn Leu Leu Val Ala Val Thr Met Ala His Glu
    130                 135                 140

Leu Gly His Asn Leu Gly Met Glu His Asp Gly Lys Asp Cys Leu Arg
145                 150                 155                 160

Gly Ala Ser Leu Cys Ile Met Arg Pro Gly Leu Thr Pro Gly Arg Ser
            165                 170                 175

Tyr Glu Phe Ser Asp Asp Ser Met Gly Tyr Tyr Gln Lys Phe Leu Asn
            180                 185                 190

Gln Tyr Lys Pro Gln Cys Ile Leu Asn Lys Pro
        195                 200

(2) INFORMATION FOR SEQ ID NO: 5:

(i) SEQUENCE CHARACTERISTICS:
            (A) LENGTH: 287 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 5:

Pro Glu Glu Leu Val His Arg Val Lys Arg Arg Ala Asp Pro Asp Pro
1               5                  10                  15

Met Lys Asn Thr Cys Lys Leu Leu Val Val Ala Asp His Arg Phe Tyr
            20                  25                  30

Arg Tyr Met Gly Arg Gly Glu Glu Ser Thr Thr Thr Asn Tyr Leu Ile
            35                  40                  45

Glu Leu Ile Asp Arg Val Asp Asp Ile Tyr Arg Asn Thr Ser Trp Asp
50                  55                  60

Asn Ala Gly Phe Lys Gly Tyr Gly Ile Gln Ile Glu Gln Ile Arg Ile
65                  70                  75                  80

Leu Lys Ser Pro Gln Glu Val Lys Pro Gly Glu Lys His Tyr Asn Met
            85                  90                  95

Ala Lys Ser Tyr Pro Asn Glu Glu Lys Asp Ala Trp Asp Val Lys Met
```

```
                100             105             110
Leu Leu Glu Gln Phe Ser Phe Asp Ile Ala Glu Ala Ser Lys Val
            115                 120             125
Cys Leu Ala His Leu Phe Thr Tyr Gln Asp Phe Asp Met Gly Thr Leu
    130                 135                 140
Gly Leu Ala Tyr Val Gly Ser Pro Arg Ala Asn Ser His Gly Gly Val
145                 150                 155                 160
Cys Pro Lys Ser Gly Ser Gly Gly Ile Cys Glu Lys Ala Tyr Tyr
                165                 170             175
Ser Pro Val Gly Lys Lys Asn Ser Lys Leu Tyr Ser Asp Gly Lys Lys
            180                 185                 190
Lys Glu Ala Asp Leu Val Thr Thr His Glu Leu Gly His Asn Phe Gly
            195                 200                 205
Ala Glu His Asp Pro Asp Gly Leu Ala Glu Cys Ala Pro Asn Glu Asp
            210                 215                 220
Gln Gly Gly Lys Tyr Val Met Tyr Pro Ile Ala Val Ser Gly Asp His
225                 230                 235                 240
Glu Asn Asn Lys Met Phe Ser Asn Cys Ser Lys Gln Ser Ile Tyr Lys
                245                 250                 255
Thr Ile Glu Ser Lys Ala Gln Glu Cys Phe Gln Glu Arg Ser Asn Lys
            260                 265                 270
Val Cys Gly Asn Ser Arg Val Asp Glu Gly Glu Glu Cys Asp Pro
                275                 280                 285

(2) INFORMATION FOR SEQ ID NO: 6:

(i) SEQUENCE CHARACTERISTICS:
        (A) LENGTH: 276 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Gln Glu Lys His Ala Ile Asn Gly Pro Glu Leu Leu Arg Lys Arg Arg
1               5                   10                  15
Thr Thr Ser Ala Glu Lys Asn Thr Cys Gln Leu Tyr Ile Gln Thr Asp
            20                  25                  30
His Leu Phe Phe Lys Tyr Tyr Gly Thr Arg Glu Ala Val Ile Ala Gln
            35                  40                  45
Ile Ser Ser His Val Lys Ala Ile Asp Thr Ile Tyr Gln Thr Thr Asp
50                  55                  60
Phe Ser Gly Ile Arg Asn Ile Ser Phe Met Val Lys Arg Ile Arg Ile
65                  70                  75                  80
Asn Thr Thr Ala Asp Glu Lys Asp Pro Thr Asn Pro Phe Arg Phe Pro
                85                  90                  95
Asn Ile Ser Val Glu Lys Phe Leu Glu Leu Asn Ser Glu Gln Asn His
                100                 105                 110
Asp Asp Tyr Cys Leu Ala Tyr Val Phe Thr Asp Arg Asp Phe Asp Asp
            115                 120                 125
Gly Val Leu Gly Leu Ala Trp Val Gly Ala Pro Ile Tyr Leu Asn Ser
            130                 135                 140
Gly Leu Thr Ser Thr Ser Leu Asn Thr Gly Ile Ile Thr Val Lys Asn
145                 150                 155                 160
Tyr Gly Lys Thr Ile Leu Thr Lys Gln Asn Tyr Gly Ser His Val Pro
```

-continued

|   |   |   |   |   | 165 |   |   |   |   | 170 |   |   |   |   | 175 |   |   |
|---|---|---|---|---|---|---|---|---|---|---|---|---|---|---|---|---|---|
| Pro | Lys | Val | Ser | His | Ile | Thr | Phe | Ala | His | Glu | Val | Gly | His | Asn | Phe | | |
| | | | 180 | | | | | 185 | | | | | 190 | | | | |
| Gly | Ser | Pro | His | Asp | Ser | Gly | Thr | Glu | Cys | Thr | Pro | Gly | Glu | Ser | Lys | | |
| | | 195 | | | | | 200 | | | | | 205 | | | | | |
| Asn | Leu | Gly | Gln | Lys | Glu | Asn | Gly | Asn | Tyr | Ile | Met | Tyr | Ala | Arg | Ala | | |
| | 210 | | | | | 215 | | | | | 220 | | | | | | |
| Thr | Ser | Gly | Asp | Lys | Leu | Asn | Asn | Asn | Lys | Phe | Ser | Leu | Cys | Ser | Ile | | |
| 225 | | | | | 230 | | | | | 235 | | | | | 240 | | |
| Arg | Asn | Ile | Ser | Gln | Val | Leu | Glu | Lys | Lys | Arg | Asn | Asn | Cys | Phe | Val | | |
| | | | 245 | | | | | 250 | | | | | 255 | | | | |
| Glu | Ser | Gly | Gln | Pro | Ile | Cys | Gly | Asn | Gly | Met | Val | Glu | Gln | Gly | Glu | | |
| | | | 260 | | | | | 265 | | | | | 270 | | | | |
| Glu | Cys | Asp | Cys | | | | | | | | | | | | | | |
| | | 275 | | | | | | | | | | | | | | | |